United States Patent
Dedhiya et al.

(10) Patent No.: US 8,471,025 B2
(45) Date of Patent: Jun. 25, 2013

(54) CRYSTALLINE FORMS OF TRANS-7-OXO-6-(SULPHOOXY)-1,6-DIAZABICYCLO[3,2,1] OCTANE-2-CARBOXAMIDE SODIUM SALT

(76) Inventors: Mahendra G. Dedhiya, Pomona, NY (US); Sisir Bhattacharya, Hauppauge, NY (US); Véronique Ducandas, Vitry sur Seine (FR); Alexandre Giuliani, Villecresnes (FR); Valérie Ravaux, Reyrieux (FR); Alain Bonnet, Chateau-Thierry (FR); Alain Priour, Paris (FR); Peter Lionel Spargo, Deal (GB)

( * ) Notice: Subject to any disclaimer, the term of this patent is extended or adjusted under 35 U.S.C. 154(b) by 308 days.

(21) Appl. No.: 12/900,567

(22) Filed: Oct. 8, 2010

(65) Prior Publication Data

US 2011/0152311 A1 Jun. 23, 2011

Related U.S. Application Data

(60) Provisional application No. 61/263,663, filed on Nov. 23, 2009.

(51) Int. Cl.
*C07D 491/02* (2006.01)
*C07D 498/02* (2006.01)
*A01N 43/42* (2006.01)
*A61K 31/44* (2006.01)

(52) U.S. Cl.
USPC .......................................... 546/121; 514/300

(58) Field of Classification Search
USPC .......................................... 514/300; 546/121
See application file for complete search history.

(56) References Cited

U.S. PATENT DOCUMENTS

| | | | |
|---|---|---|---|
| 6,417,175 | B1 | 7/2002 | Ishikawa et al. |
| 6,906,055 | B2 | 6/2005 | Ishikawa et al. |
| 7,419,973 | B2 | 9/2008 | Ishikawa et al. |
| 2005/0020572 | A1 | 1/2005 | Aszodi et al. |

FOREIGN PATENT DOCUMENTS

| | | |
|---|---|---|
| WO | 0210172 | 2/2002 |
| WO | 03063864 | 8/2003 |

OTHER PUBLICATIONS

International Search Report for corresponding International App. No. PCT/EP2010/065147 mailed Mar. 23, 2011.
Written Opinion for corresponding International App. No. PCT/EP2010/065147 mailed Apr. 9, 2012.
Bonnefoy, Alain et al., "In vitro activity of AVE1330A, an innovative broad-spectrum non-.beta.-lactam.beta.-lactamase inhibitor", Journal of Antimicrobial Chemotehrapy, 2004, vol. 54, No. 2, pp. 410-417.
Livermore, David M. et al., "NXL-104 combinations versus Enterobacteriaceae with CTX-M extended-spectrum . beta.-lactamases and carbapenemases" Journal of Antimicrobial Chemotherapy, 2008, vol. 62, No. 5, pp. 1053-1056.
Stachyra, Therese et al., "In vitro activity of the .beta.-lactamase inhibitor NXL104 against KPC-2 carbapenemase and Enterobacteriaceae expressing KPC carbapenemases", Journal of Antimicrobial Chemotherapy, Jun. 2, 2009, vol. 64, No. 2, pp. 326-329.
Endimiani, Andrea et al, "In vitro activity of NXL104 in combination with .beta.-lactams against *Klebsiella pneumoniae* isolates producing KPC carbapenemases", Aug. 2009, vol. 53, No. 8, pp. 3599-3561.
Miossec C et al., "In vitro activity of the new beta-lactamase inhibitor NXL104: restoration of ceftazidine (CAZ) efficacy against carbapenem-resistant *Enterobacteriaceae* strains", Sep. 17, 2007, 47th IACCA Meeting, Chicago.

*Primary Examiner* — Niloofar Rahmani

(57) ABSTRACT

The present invention relates to novel crystalline forms of sodium salt of trans-7-oxo-6-(sulphooxy)-1,6-diazabicyclo [3,2,1]octane-2-carboxamide (e.g., NXL-104) thereof. The present invention relates to compositions comprising a crystalline form of sodium salt of trans-7-oxo-6-(sulphooxy)-1, 6-diazabicyclo[3,2,1]octane-2-carboxamide (e.g., NXL-104) alone or in combination with an antibacterial agent (e.g., ceftaroline fosamil). Processes for the preparation of the crystalline forms and methods of treating bacterial infections by administering the crystalline forms alone or in combination with an antibacterial agent (e.g., ceftaroline fosamil) are also described.

34 Claims, 6 Drawing Sheets

CRYSTALLINE FORMS OF TRANS-7-OXO-6-(SULPHOOXY)-1,6-DIAZABICYCLO[3,2,1] OCTANE-2-CARBOXAMIDE SODIUM SALT

CROSS-REFERENCE TO RELATED APPLICATIONS

This application claims priority under 35 U.S.C. §119, based on French Application No. 0904864 filed on Oct. 9, 2009 and U.S. Provisional Application Ser. No. 61/263,663 filed on Nov. 23, 2009, both of which are hereby incorporated by reference in their entirety.

FIELD OF THE INVENTION

The present invention relates to novel crystalline forms of trans-7-oxo-6-(sulphooxy)-1,6-diazabicyclo[3,2,1]octane-2-carboxamide sodium salt (e.g., NXL-104) and compositions comprising the crystalline forms alone or in combination with an antibacterial agent (e.g., ceftaroline fosamil). Processes for the preparation of the crystalline forms and methods of treating bacterial infections by administering the crystalline forms alone or in combination with an antibacterial agent (e.g., ceftaroline fosamil) are also described.

BACKGROUND OF THE INVENTION

U.S. Pat. No. 7,112,592 discloses novel heterocyclic compounds and their salts, processes for making the compounds and methods of using the compounds as antibacterial agents. One such compound is sodium salt of trans-7-oxo-6-(sulphooxy)-1,6-diazabicyclo[3,2,1]octane-2-carboxamide. Application WO 02/10172 describes the production of azabicyclic compounds and salts thereof with acids and bases, and in particular, trans-7-oxo-6-sulphoxy-1,6-diazabicyclo[3.2.1]octane-2-carboxamide and its pyridinium, tetrabutylammonium and sodium salts. Application WO 03/063864 and U.S. Patent Publication No. 2005/0020572 describe the use of compounds including trans-7-oxo-6-(sulphooxy)-1,6-diazabicyclo[3,2,1]octane-2-carboxamide sodium salt, as β-lactamase inhibitors that can be administered alone or in, combination with β-lactamine antibacterial agents. These references are incorporated herein by reference, in their entirety.

Ceftaroline is a novel parenteral cephalosporin with a broad spectrum of activity against clinically important community-acquired and hospital-acquired Gram-negative and Gram-positive pathogens including methicillin-resistant *Staphylococcus aureus* and multidrug-resistant *Streptococcus pneumoniae*.

U.S. Pat. No. 6,417,175 discloses compounds having excellent antibacterial activities for a broad range of Gram-positive and Gram-negative bacteria. These compounds are represented by the general formula:

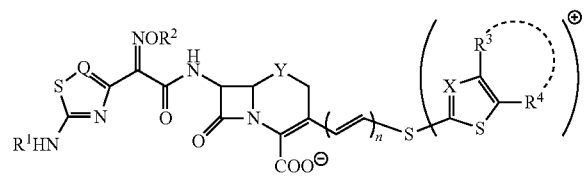

wherein $R^1$-$R^4$, Q, X, Y and n are as defined therein.

U.S. Pat. No. 6,417,175 discloses methods for preparing the compounds, and generically discloses formulations of the compounds, such as aqueous and saline solutions for injection. One such compound is 7β-[2(Z)-ethoxyimino-2-(5-phosphonoamino-1,2,4-thiadiazole-3-yl)acetamido]-3-[4-(1-methyl-4-pyridinio)-2-thiazolylthio]-3-cephem-4-carboxylate.

U.S. Pat. No. 6,906,055 discloses a chemical genus which includes compounds of formula:

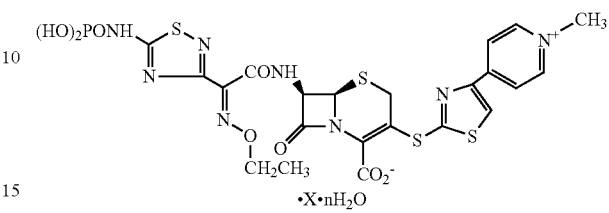

Ceftaroline fosamil is a sterile, synthetic, parenteral pro-drug cephalosporin antibiotic. The N-phosphonoamino water-soluble prodrug is rapidly converted into the bioactive ceftaroline, which has been demonstrated to exhibit antibacterial activity. Ceftaroline fosamil is known as (6R,7R)-7-{(2Z)-2-(ethoxyimino)-2-[5-(phosphonoamino)-1,2,4-thiadiazol-3-yl]acetamido}-3-{[4-(1-methylpyridin-1-ium-4-yl)-1,3-thiazol-2-yl]sulfanyl}-8-oxo-5-thia-1-azabicyclo[4.2.0]oct-2-ene-2-carboxylate. Ceftaroline fosamil may be an acetic acid hydrous form.

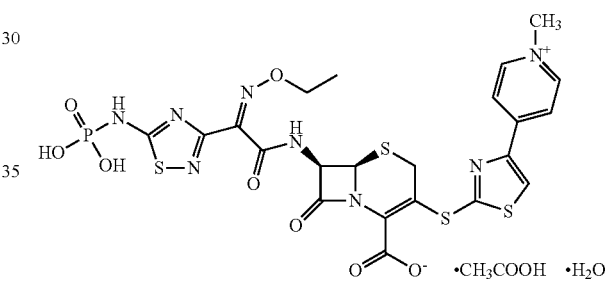

U.S. Pat. No. 7,419,973 discloses compositions comprising ceftaroline fosamil and a pH adjuster, such as, L-arginine.

U.S. Pat. Nos. 6,417,175 and 6,906,055 and 7,419,973 are incorporated herein by reference, in their entirety.

The present invention relates to the solid state physical properties of trans-7-oxo-6-(sulphooxy)-1,6-diazabicyclo[3,2,1]octane-2-carboxamide sodium salt (e.g., NXL-104). These properties may be influenced by controlling the conditions under which trans-7-oxo-6-(sulphooxy)-1,6-diazabicyclo[3,2,1]octane-2-carboxamide sodium salt (e.g., NXL-104) is obtained in solid form.

Solid state physical properties include, for example, the flowability of the milled solid, rate of dissolution and stability. The physical characteristics are influenced by the conformation and orientation of molecules in the unit cell, which defines a particular crystalline form of a substance. A crystalline form may give rise to thermal behavior different from that of the amorphous material or another crystalline form. Thermal behavior is measured in the laboratory using techniques such as capillary melting point, thermogravimetric analysis (TGA) and differential scanning calorimetry (DSC). These techniques may be used to distinguish between different crystalline forms. A particular crystalline form may show distinct spectroscopic properties that can be detected using powder X-ray diffractometry (XRPD), nuclear magnetic resonance (NMR) spectrometry, Raman spectroscopy and infrared (IR) spectrometry.

In deciding which crystalline form is preferable, the numerous properties of the crystalline forms must be compared and the preferred crystalline form chosen based on the many physical property variables. A particular crystalline form may be preferable in certain circumstances in which certain aspects, such as ease of preparation, stability, etc., are deemed to be critical. In other situations, a different crystalline form may be preferred for greater solubility and/or superior pharmacokinetics.

The discovery of new crystalline forms of a pharmaceutically useful compound provides a new opportunity to improve the performance characteristics of a pharmaceutical product. New crystalline forms of trans-7-oxo-6-(sulphooxy)-1,6-diazabicyclo[3,2,1]octane-2-carboxamide sodium salt have now been discovered.

There is an existing and continual need in the art for new and improved compositions and methods for treating bacterial infections by administering antibacterial agents. Surprisingly and unexpectedly, compositions comprising a crystalline form of trans-7-oxo-6-(sulphooxy)-1,6-diazabicyclo[3,2,1]octane-2-carboxamide sodium salt and ceftaroline fosamil have been found to stable. Such formulations may be used for the treatment of bacterial infections, such as, complicated skin and structure infection and community acquired pneumonia.

SUMMARY OF THE INVENTION

The present invention relates to novel crystalline forms of trans-7-oxo-6-(sulphooxy)-1,6-diazabicyclo[3,2,1]octane-2-carboxamide sodium salt (e.g., NXL-104).

The present invention provides compositions comprising a crystalline form of trans-7-oxo-6-(sulphooxy)-1,6-diazabicyclo[3,2,1]octane-2-carboxamide sodium salt (e.g., NXL-104) alone or in combination with an antibacterial agent (e.g., ceftaroline fosamil). Methods of treating bacterial infections by administering the crystalline forms alone or in combination with an antibacterial agent (e.g., ceftaroline fosamil) are also described.

DETAILED DESCRIPTION OF THE INVENTION

Figure 1:
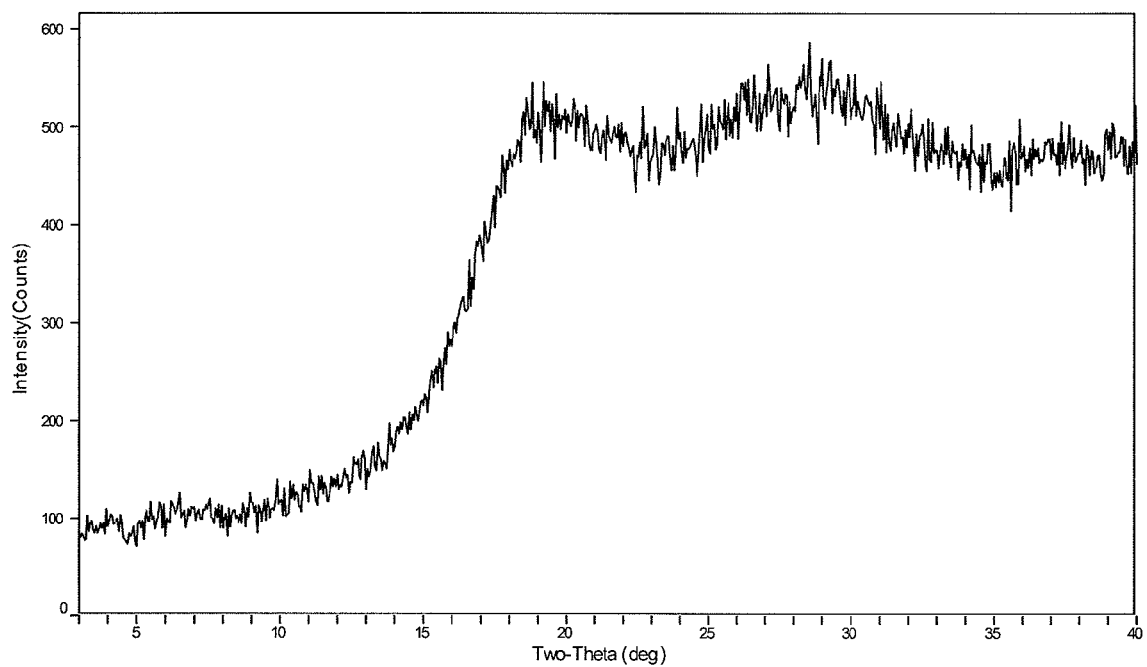
FIG. 1 shows the powder X-Ray diffraction pattern of amorphous trans-7-oxo-6-(sulphooxy)-1,6-diazabicyclo[3,2,1]octane-2-carboxamide sodium salt (NXL-104).

The present invention provides novel crystalline forms of trans-7-oxo-6-(sulphooxy)-1,6-diazabicyclo[3,2,1]octane-2-carboxamide sodium salt (e.g., NXL-104). NXL-104 may also be referred to as monosodium salt of (1R,2S,5R)-7-oxo-6-sulphoxy-1,6-diazabicyclo[3.2.1]octane-2-carboxamide.

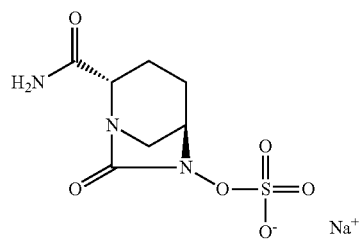

The crystalline forms may be hydrated (e.g., a monohydrate or a dihydrate) or anhydrous.

The present invention also provides compositions comprising the crystalline forms alone or in combination with an antibacterial agent (e.g., ceftaroline fosamil), processes for making the crystalline forms and methods of treating bacterial infections by administering the crystalline forms alone or in combination with an antibacterial agent (e.g., ceftaroline fosamil).

Form I

In one aspect, the present invention provides a crystalline form of trans-7-oxo-6-(sulphooxy)-1,6-diazabicyclo[3,2,1]octane-2-carboxamide sodium salt called Form I.

In specific examples, the present invention provides a crystalline form of sodium salt of (1R,2S,5R)-7-oxo-6-sulphooxy-1,6-diazabicyclo[3.2.1]octane-2-carboxamide called Form I.

The sodium salt of trans-7-oxo-6-(sulphooxy)-1,6-diazabicyclo[3,2,1]octane-2-carboxamide, in particular, (1R,2S,5R)-7-oxo-6-sulphoxy-1,6-diazabicyclo[3.2.1]octane-2-carboxamide, is a beta-lactamase inhibitor, which reacts with a protein, forming a covalent bond. This reactive inhibitor, a consequence of the internal strain of the N-oxosulphoxyurea ring, is intrinsically sensitive to moisture and to heat, just like the β-lactams, although it is not one. The main manner of degradation of the sodium salt of (1R,2S,5R)-7-oxo-6-sulphoxy-1,6-diazabicyclo[3.2.1]octane-2-carboxamide is by hydrolysis of the N-oxosulphoxyurea ring. To minimize degradation, it is advantageous to isolate this molecule at room temperature or at low temperature and minimize the duration of exposure in aqueous solution. These conditions are fulfilled during crystallization or lyophilisation but are difficult to fulfil during concentration of an aqueous solution to dryness, as described in Application WO 02/10172. In practice, the aqueous solution containing the sodium salt of (1R,2S,5R)-7-oxo-6-sulphoxy-1,6-diazabicyclo[3.2.1]octane-2-carboxamide can only be concentrated by lyophilisation, in order to obtain the product in the amorphous form.

In exemplary embodiments, the Form I is characterized by an X-Ray powder diffraction pattern comprising a characteristic peak, such as, at about 13.0+/−0.5 degrees 2θ. In other embodiments, the Form I is characterized by an X-Ray powder diffraction pattern comprising a characteristic peak at about 16.5+/−0.5 degrees 2θ. In still other embodiments, the Form I is characterized by an X-Ray powder diffraction pattern comprising a characteristic peak at about 17.5+/−0.5 degrees 2θ.

In exemplary embodiments, the Form I is characterized by an X-Ray powder diffraction pattern comprising a characteristic peak at about 13.0; about 16.5, about 17.5+/−0.5 degrees 2θ or a combination thereof. In further embodiments, the Form I is characterized by an X-Ray powder diffraction pattern comprising a characteristic peak at about 17.3; about 22.3+/−0.5 degrees 2θ or a combination thereof. In other embodiments, the Form I is further characterized by an X-Ray powder diffraction pattern comprising a characteristic peak at about 19.2 or about 19.5+/−0.5 degrees 2θ or a combination thereof. In further embodiments, the Form I is characterized by an X-Ray powder diffraction pattern comprising a characteristic peak at about 19.9; about 22.0; about 25.2; about 28.2+/−0.5 degrees 2θ or a combination thereof.

In specific embodiments, the Form I is characterized by an X-Ray powder diffraction pattern comprising a characteristic peak at about 13.0; about 16.5; about 17.3; about 17.5; about 19.2; about 19.5; about 19.9; about 22.0; about 22.3; about 25.2; or about 28.2+/−0.5 degrees 2θ or a combination thereof. In further embodiments, the Form I is characterized by an X-Ray powder diffraction pattern comprising a characteristic peak at about 23.2; about 30.2; about 30.9; about 36.1+/−0.5 degrees 2θ or a combination thereof. In exemplary embodiments, the Form I is characterized by an X-Ray powder diffraction pattern comprising one or more characteristic peaks at 2θ (±0.1°) 12.97, 16.45, 17.24, 17.45, 22.29.

In exemplary embodiments, the Form I of trans-7-oxo-6-(sulphooxy)-1,6-diazabicyclo[3,2,1]octane-2-carboxamide sodium salt (e.g., NXL-104) is characterized by an X-Ray powder diffraction pattern comprising characteristic peaks at about 13.0; about 16.5; about 17.3; about 17.5; about 19.2; about 19.5; about 19.9; about 22.0; about 22.3; about 23.2; about 25.2; about 28.2; about 30.2; about 30.9 and about 36.1+/−0.5 degrees 2θ.

In some embodiments, the Form I is characterized by an X-Ray powder diffraction pattern comprising a d-spacing value, such as, at about 6.8+/−2 nm. In other embodiments, the Form I is characterized by an X-Ray powder diffraction pattern comprising a d-spacing value at about 5.1+/−2 nm. In still other embodiments, the Form I is characterized by an X-Ray powder diffraction pattern comprising a d-spacing value at about 5.4+/−2 nm.

In exemplary embodiments, the Form I is characterized by an X-Ray powder diffraction pattern comprising a d-spacing value at about 5.1; about 5.4; about 6.8+/−2 nm or a combination thereof. In further embodiments, the Form I is characterized by an X-Ray powder diffraction pattern comprising a d-spacing value at about 4.0+/−2 nm. In other embodiments, the Form I characterized by an X-Ray powder diffraction pattern comprising a d-spacing value at about 4.6+/−2 nm. In further embodiments, the Form I is characterized by an X-Ray powder diffraction pattern comprising a d-spacing value at about 3.2; about 3.5; about 4.0; about 4.5+/−2 nm or a combination thereof.

In certain embodiments, the Form I of trans-7-oxo-6-(sulphooxy)-1,6-diazabicyclo[3,2,1]octane-2-carboxamide sodium salt (e.g., NXL-104) is characterized by an X-Ray powder diffraction pattern comprising d-spacing values at about 2.5; about 2.9; about 3.0; about 3.2; about 3.5; about 3.8; about 4.0; about 4.5; about 4.6; about 5.1; about 5.4 or about 6.8+/−2 nm or a combination thereof.

In exemplary embodiments, the Form I of trans-7-oxo-6-(sulphooxy)-1,6-diazabicyclo[3,2,1]octane-2-carboxamide sodium salt (e.g., NXL-104) is characterized by an X-Ray powder diffraction pattern comprising d-spacing values at about 2.5; about 2.9; about 3.0; about 3.2; about 3.5; about 3.8; about 4.0; about 4.5; about 4.6; about 5.1; about 5.4; and about 6.8+/−2 nm.

Form II

In another aspect, the present invention provides a crystalline form of trans-7-oxo-6-(sulphooxy)-1,6-diazabicyclo[3,2,1]octane-2-carboxamide sodium salt (e.g., NXL-104) called Form II.

For example, the present invention provides a crystalline form of sodium salt of (1R,2S,5R)-7-oxo-6-sulphooxy-1,6-diazabicyclo[3.2.1]octane-2-carboxamide called Form II.

In some embodiments, the Form II is characterized by an X-Ray powder diffraction pattern comprising a characteristic peak at about 8.5; about 15.4; about 16.4; about 17.1; about 23.5 or about 24.3+/−0.5 degrees 2θ or a combination thereof.

In exemplary embodiments, the Form II is characterized by an X-Ray powder diffraction pattern comprising a characteristic peak at about 17.1+/−0.5 degrees 2θ. In other embodiments, the Form II is characterized by an X-Ray powder diffraction pattern comprising a characteristic peak at about 16.4+/−0.5 degrees 2θ. In still other embodiments, the Form II is characterized by an X-Ray powder diffraction pattern comprising a characteristic peak at about 8.5+/−0.5 degrees 2θ.

In further embodiments, the Form II characterized by an X-Ray powder diffraction pattern comprising a characteristic peak at about 15.4; about 23.5+/−0.5 degrees 2θ or a combination thereof. In other embodiments, the Form II is further characterized by an X-Ray powder diffraction pattern comprising a characteristic peak at about 24.3+/−0.5 degrees 2θ. In exemplary embodiments, the Form II of trans-7-oxo-6-(sulphooxy)-1,6-diazabicyclo[3,2,1]octane-2-carboxamide sodium salt is characterized by an X-Ray powder diffraction pattern comprising characteristic peaks at about 8.5; about 15.4; about 16.4; about 17.1; about 23.5 and about 24.3+/−0.5 degrees 2θ. In further specific embodiments, the Form II of trans-7-oxo-6-(sulphooxy)-1,6-diazabicyclo[3,2,1]octane-2-carboxamide sodium salt is characterized by one or more peaks at 2θ (±0.1°) 8.48, 15.34, 16.38, 17.04, 24.28.

In specific embodiments, the Form II is characterized by an X-Ray powder diffraction pattern comprising a d-spacing value at about 3.7; about 3.8; about 5.2; about 5.4; about 5.8 or about 10.4+/−2 nm or a combination thereof.

In some embodiments, the Form II is characterized by an X-Ray powder diffraction pattern comprising a d-spacing value, such as, at about 5.2+/−2 nm.

In other embodiments, the Form II is characterized by an X-Ray powder diffraction pattern comprising a d-spacing value at about 5.4+/−2 nm. In still other embodiments, the Form II is characterized by an X-Ray powder diffraction pattern comprising a d-spacing value at about 10.4+/−2 nm. In further embodiments, the Form II characterized by an X-Ray powder diffraction pattern comprising a d-spacing value at about 3.8 or about 5.8+/−2 nm or a combination thereof.

In exemplary embodiments, the Form II of trans-7-oxo-6-(sulphooxy)-1,6-diazabicyclo[3,2,1]octane-2-carboxamide sodium salt (e.g., NXL-104) is characterized by an X-Ray powder diffraction pattern comprising d-spacing values at about 3.7; about 3.8; about 5.2; about 5.4; about 5.8 and about 10.4+/−2 nm.

Form III

In another aspect, the present invention relates to a crystalline form of trans-7-oxo-6-(sulphooxy)-1,6-diazabicyclo[3,2,1]octane-2-carboxamide sodium salt (e.g., NXL-104) called Form III.

For example, the present invention provides a crystalline form of sodium salt of (1R,2S,5R)-7-oxo-6-sulphooxy-1,6-diazabicyclo[3.2.1]octane-2-carboxamide called Form III.

In exemplary embodiments, the Form III is characterized by an X-Ray powder diffraction pattern comprising characteristic peaks at about 9.8; about 13.6; about 15.0; about 15.8; about 19.5; about 19.7; about 22.5; about 22.8; about 23.5; about 24.3; about 24.6; about 27.6; about 27.9; about 29.8 or about 31.7+/−0.5 degrees 2θ or a combination thereof.

In exemplary embodiments, the Form III is characterized by an X-Ray powder diffraction pattern comprising a characteristic peak at about 9.8+/−0.5 degrees 2θ. In other embodiments, the Form III is characterized by an X-Ray powder diffraction pattern comprising a characteristic peak at about 19.5+/−0.5 degrees 2θ. In still other embodiments, the Form III is characterized by an X-Ray powder diffraction pattern comprising a characteristic peak at about 15.0; about 15.8 or about 22.5+/−0.5 degrees 2θ or a combination thereof.

In some embodiments, the Form III is characterized by an X-Ray powder diffraction pattern comprising a characteristic peak at about 13.6; about 19.7; about 23.5; about 24.6 or about 29.8+/−0.5 degrees 2θ or a combination thereof. In further embodiments, the Form III is characterized by an X-Ray powder diffraction pattern comprising a characteristic peak at about 22.8; about 24.3; about 27.6; about 27.9 or about 31.7+/−0.5 degrees 2θ or a combination thereof.

In exemplary embodiments, the Form III is characterized by an X-Ray powder diffraction pattern comprising characteristic peaks at about 9.8; about 13.6; about 15.0; about 15.8; about 19.5; about 19.7; about 22.5; about 22.8; about 23.5; about 24.3; about 24.6; about 27.6; about 27.9; about 29.8; about 31.7 and +/−0.5 degrees 2θ. In exemplary embodiments, the Form III is characterized by an X-Ray powder diffraction pattern comprising one or more characteristic peaks at 2θ (±0.1°) 13.65, 15.01, 15.38, 15.72, 19.42.

In some embodiments, the Form III is characterized by an X-Ray powder diffraction pattern comprising d-spacing values at about 2.8; about 3.0; about 3.2; about 3.6; about 3.7; about 3.8; about 3.9; about 4.0; about 4.5; about 4.6; about 5.6; about 5.9; about 6.5 or about 9.0+/−2 nm or a combination thereof.

In exemplary embodiments, the Form III is characterized by an X-Ray powder diffraction pattern comprising a d-spacing value, such as, at about 9.0+/−2 nm. In other embodiments, the Form III is characterized by an X-Ray powder diffraction pattern comprising a d-spacing value at about 4.6+/−2 nm. In still other embodiments, the Form III is characterized by an X-Ray powder diffraction pattern comprising a d-spacing value at about 4.0; about 4.5; about 5.6; about 5.9 or about 6.5+/−2 nm or a combination thereof.

In further embodiments, the Form III is characterized by an X-Ray powder diffraction pattern comprising a d-spacing value at about 2.8; about 3.0; about 3.2; about 3.6; about 3.7; about 3.8 or about 3.9+/−2 nm or a combination thereof.

In exemplary embodiments, the Form III is characterized by an X-Ray powder diffraction pattern comprising d-spacing values at about 2.8; about 3.0; about 3.2; about 3.6; about 3.7; about 3.8; about 3.9; about 4.0; about 4.5; about 4.6; about 5.6; about 5.9; about 6.5 and about 9.0+/−2 nm.

Form IV

In another aspect, the present invention provides the present invention provides a crystalline form of trans-7-oxo-6-(sulphooxy)-1,6-diazabicyclo[3,2,1]octane-2-carboxamide sodium salt (e.g., NXL-104) called Form IV.

For example, the present invention provides a crystalline form of sodium salt of (1R,2S,5R)-7-oxo-6-sulphooxy-1,6-diazabicyclo[3.2.1]octane-2-carboxamide called Form IV.

In some embodiments, the Form IV is characterized by an X-Ray powder diffraction pattern comprising a characteristic peak, such as, at about 8.7; about 11.3; about 12.5; about 16.3; about 17.5; about 17.8; about 18.6; about 21.0; about 22.3; about 26.2; about 26.6; about 26.9; about 27.6; about 28.7; about 29.8; about 30.4; about 31.2; about 32.9; about 33.4; about 34.4; about 37.1; about 37.3; about 37.6 or about 38.5+/−0.5 degrees 2θ or a combination thereof.

In exemplary embodiments, the Form IV is characterized by an X-Ray powder diffraction pattern comprising a characteristic peak at about 18.6+/−0.5 degrees 2θ. In other embodiments, the Form IV is characterized by an X-Ray powder diffraction pattern comprising a characteristic peak at about 17.5+/−0.5 degrees 2θ. In still other embodiments, the Form IV is characterized by an X-Ray powder diffraction pattern comprising a characteristic peak at about 17.8+/−0.5 degrees 2θ. In certain embodiments, the Form IV is characterized by an X-Ray powder diffraction pattern comprising a characteristic peak at about 16.3+/−0.5 degrees 2θ.

In some embodiments, the Form IV is characterized by an X-Ray powder diffraction pattern comprising a characteristic peak, such as, at about 8.7 or about 22.3+/−0.5 degrees 2θ.

The Form IV may be further characterized by an X-Ray powder diffraction pattern comprising a characteristic peak at about 12.5; about 21.0; about 26.6 or about 26.9; +/−0.5 degrees 2θ or a combination thereof. In other embodiments, the Form IV may be further characterized by an X-Ray powder diffraction pattern comprising a characteristic peak at about 11.3; about 26.2; about 27.6; about 28.7; about 29.8; about 30.4; about 31.2; about 32.9; about 33.4; about 34.4; about 37.1; about 37.3; about 37.6 or about 38.5+/−0.5 degrees 2θ or a combination thereof.

In exemplary embodiments, the Form IV is characterized by an X-Ray powder diffraction pattern comprising a characteristic peak, such as, at about 8.7; about 11.3; about 12.5; about 16.3; about 17.5; about 17.8; about 18.6; about 21.0; about 22.3; about 26.2; about 26.6; about 26.9; about 27.6; about 28.7; about 29.8; about 30.4; about 31.2; about 32.9; about 33.4; about 34.4; about 37.1; about 37.3; about 37.6 and about 38.5+/−0.5 degrees 2θ or a combination thereof.

In specific embodiments, the Form IV is characterized by an X-Ray powder diffraction pattern comprising d-spacing values at about 2.3; about 2.4; about 2.6; about 2.7; about 2.9; about 3.0; about 3.1; about 3.2; about 3.3; about 3.4; about 4.0; about 4.2; about 4.8; about 5.0; about 5.1; about 5.4; about 7.1; about 7.8 or about 10.1+/−2 nm or a combination thereof.

In exemplary embodiments, the Form IV is characterized by an X-Ray powder diffraction pattern comprising a d-spacing value, such as, at about 4.8+/−2 nm. In other embodiments, the Form IV is characterized by an X-Ray powder diffraction pattern comprising a d-spacing value at about 5.1+/−2 nm. In still other embodiments, the Form IV is characterized by an X-Ray powder diffraction pattern comprising a d-spacing value at about 4.0; about 5.0; about 5.4 or about 10.1+/−2 nm or a combination thereof.

In some embodiments, the Form IV is further characterized by an X-Ray powder diffraction pattern comprising a d-spacing value at about 3.3; about 4.2 or about 7.1+/−2 nm or a combination thereof. In other embodiments, the Form IV is further characterized by an X-Ray powder diffraction pattern comprising a d-spacing value at about 2.3; about 2.4; about 2.6; about 2.7; about 2.9; about 3.0; about 3.1; about 3.2; about 3.4 or about 7.8+/−2 nm or a combination thereof.

For example, the Form IV is characterized by an X-Ray powder diffraction pattern comprising d-spacing values at about 2.3; about 2.4; about 2.6; about 2.7; about 2.9; about 3.0; about 3.1; about 3.2; about 3.3; about 3.4; about 4.0; about 4.2; about 4.8; about 5.0; about 5.1; about 5.4; about 7.1; about 7.8 and about 10.1+/−2 nm.

Form V

In another aspect, the present invention provides a crystalline form of trans-7-oxo-6-(sulphooxy)-1,6-diazabicyclo[3,2,1]octane-2-carboxamide sodium salt (e.g., NXL-104) called Form V.

For example, the present invention provides a crystalline form of sodium salt of (1R,2S,5R)-7-oxo-6-sulphooxy-1,6-diazabicyclo[3.2.1]octane-2-carboxamide called Form V.

In exemplary embodiments, the Form V is characterized by an X-Ray powder diffraction pattern comprising a characteristic peak, such as, at about 6.5; about 8.5; about 13.4; about 14.4; about 15.4; about 15.5; about 16.4; about 17.1; about 18.0; about 19.3; about 19.5; about 21.0; about 22.9; about 24.3; about 27.3 or about 31.9+/−0.5 degrees 2θ or a combination thereof.

In some embodiments, the Form V is characterized by an X-Ray powder diffraction pattern comprising a characteristic peak at about 6.5+/−0.5 degrees 2θ. In other embodiments, the Form V is characterized by an X-Ray powder diffraction pattern comprising a characteristic peak at about 18.0+/−0.5 degrees 2θ. In still other embodiments, the Form V is characterized by an X-Ray powder diffraction pattern comprising a characteristic peak at about 19.3+/−0.5 degrees 2θ. The Form V may be further characterized by an X-Ray powder diffraction pattern comprising a characteristic peak at about 14.4; about 15.5; about 16.4; about 17.1 or about 19.5+/−0.5 degrees 2θ or a combination thereof. In still other embodiments, the Form V may be further characterized by an X-Ray powder diffraction pattern comprising a characteristic peak at about 8.5; about 13.4; about 15.4; about 21.0; about 22.9; about 24.3; about 27.3 or about 31.9+/−0.5 degrees 2θ or a combination thereof.

In exemplary embodiments, the Form V is characterized by an X-Ray powder diffraction pattern comprising characteristic peaks at about 6.5; about 8.5; about 13.4; about 14.4; about 15.4; about 15.5; about 16.4; about 17.1; about 18.0; about 19.3; about 19.5; about 21.0; about 22.9; about 24.3; about 27.3 and about 31.9+/−0.5 degrees 2θ.

In some embodiments, the Form V is characterized by an X-Ray powder diffraction pattern comprising a d spacing value at about 2.8; about 3.3; about 3.7; about 3.9; about 4.2; about 4.5; about 4.6; about 4.9; about 5.2; about 5.4; about 5.7; about 5.8; about 6.1; about 6.6; about 10.4 or about 13.6+/−2 nm or a combination thereof.

In some embodiments, the Form V is characterized by an X-Ray powder diffraction pattern comprising a d spacing value at about 13.6+/−2 nm. In other embodiments, the Form V is characterized by an X-Ray powder diffraction pattern comprising a d spacing value at about 4.6+/−2 nm. In still other embodiments, the Form V is characterized by an X-Ray powder diffraction pattern comprising a d spacing value at about 4.9+/−2 nm. In certain embodiments, the Form V is characterized by an X-Ray powder diffraction pattern comprising a d spacing value at about 6.1+/−2 nm. The X-Ray powder diffraction pattern may further comprise a d spacing value at about 2.8; about 3.3; about 3.7; about 3.9; about 4.2; about 4.5; about 5.2; about 5.4; about 5.7; about 5.8; about 6.6 or about 10.4+/−2 nm or a combination thereof.

In exemplary embodiments, the Form V is characterized by an X-Ray powder diffraction pattern comprising a d spacing value at about 2.8; about 3.3; about 3.7; about 3.9; about 4.2; about 4.5; about 4.6; about 4.9; about 5.2; about 5.4; about 5.7; about 5.8; about 6.1; about 6.6; about 10.4 and about 13.6+/−2 nm.

In exemplary embodiments, the Form II is a monohydrate containing 5.90% water (weight/weight) and the Form III is a dihydrate. By coupling thermogravimetric analysis (TGA) with differential thermal analysis (SDTA) at 10° C./min, the Form II displays a weight loss of 5.7% at approximately 110° C., corresponding to the dehydration of the salt, followed by a decomposition exotherm with weight loss between 220 and 240° C. By the same technique, the Form III displays a first weight loss of 5% at approximately 60° C. and then a second weight loss of 5% at approximately 100° C. before decomposition between 220 and 240° C. This loss of water in 2 stages corresponds to a dihydrated form with two non-equivalent molecules of water in the crystal lattice.

In exemplary embodiments, the Forms I, IV or V are anhydrous. A maximum amount of water from 0 to 0.6% is detected by Karl Fischer analysis in a product of Form I prepared as described later in the application. The polymorphic forms I and IV display an exothermic decomposition peak between 220 and 240° C. measured by DSC (Differential Scanning calorimetry).

In some embodiments, the experimental powder diffraction patterns are obtained by diffraction of X-rays on powder in a Rigaku Miniflex X-ray diffractometer with the Kα radiation of copper ($\lambda$=1.541 Å). The samples, without grinding, are put on a glass plate and are analyzed at ambient temperature and humidity. Data are collected at 0.05° interval, 2°/minute from 3°-40° 2θ. In some examples, the peaks with a relative intensity of more than about 10% are considered as characteristic peaks.

In other embodiments, the experimental powder diffraction patterns are obtained by diffraction of X-rays on powder in an X'pert Pro Philips instrument with the Kα radiation of copper ($\lambda$=1.5406 Å). The samples, without grinding, are put on a glass plate and are analyzed at ambient temperature and humidity with an angle 2θ from 5 to 50°. In some examples, the characteristic peaks of each form are determined using five lines that are generally the most intense. The mean value of each peak and its standard deviation are calculated from the experimental values of representative samples of each form.

In some embodiments, the crystal structures of the monocrystals of the dihydrate forms are obtained at 296K on a Rigaku Rapid R axis diffractometer equipped with a rotating copper anode (l=1.5406 Å). The crystals structures of monocrystal of the monohydrate form are obtained at 233K on a Bruker Nonius diffractometer with the Kα radiation of molybdenum (l=0.7093 Å). Powder diffraction patterns are normally measured using copper Kα radiation. For comparison with the experimental powder patterns, the theoretical powder diffraction patterns for the hydrate forms are calculated from the corresponding crystal structure data using the appropriate I value for copper Kα radiation (1.5406 Å).

One skilled in the art will understand that the relative intensities and positions of the peaks obtained by X-Ray powder diffraction may vary depending upon factors such as, the sample preparation technique, the sample mounting procedure and the particular instrument employed. For example, in additional embodiments, the listed X-Ray powder diffraction pattern peaks for the crystalline form of trans-7-oxo-6-(sulphooxy)-1,6-diazabicyclo[3,2,1]octane-2-carboxamide sodium salt (e.g., NXL-104) may be about +/−0.2 degrees 2θ.

It is known that an X-ray powder diffraction pattern may be obtained which has one or more measurement errors depending on measurement conditions (such as equipment or machine used). Intensities in an X-ray powder diffraction pattern may fluctuate depending on measurement conditions. Therefore, it should be understood that the crystalline forms of the present invention are not limited to the crystals that provide X-ray powder diffraction patterns identical to the X-ray powder diffraction patterns described in this application, and any crystals providing X-ray powder diffraction patterns substantially the same as those described in the application fall within the scope of the present invention. For example, relative intensity of peaks can be affected by grains above 30 microns in size and non-unitary aspect ratios, which may affect analysis of samples. A person skilled in the art will recognize that the position of reflections can be affected by the precise height at which the sample sits in the diffractometer and the zero calibration of the diffractometer. The surface planarity of the sample may also have a small effect. Therefore, the diffraction pattern data described herein are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is about 5% or less, in particular plus or minus 0.5° 2-theta, and such degree of a measurement error should be taken into account when considering the X-ray powder diffraction patterns described in this application. Furthermore, it should be understood that intensities may fluctuate depending on experimental conditions and sample preparation (preferred orientation).

The standard deviation for d-spacing is calculated based on an angle of 5° 2-theta. In some embodiments, the standard deviation for d-spacing may be between +/−0.1 nm and +/−2 nm. For example, the d-spacing values for the crystalline forms described in the application may vary by +/−0.2 nm, +/−0.3 nm, +/−0.5 nm, +/−1 nm, +/−1.5 nm or about +/−2 nm.

In one aspect, substantially pure crystalline forms of the present invention are provided. For example, the present invention includes Forms I-V of trans-7-oxo-6-(sulphooxy)-1,6-diazabicyclo[3,2,1]octane-2-carboxamide sodium salt (e.g., NXL-104) as described in this application that are about ≧95% pure. For example, the forms may be about ≧95%, ≧96%, ≧97%, ≧98% or ≧99% pure.

In exemplary embodiments, the present invention provides Forms I-V of sodium salt of (1R,2S,5R)-7-oxo-6-sulphooxy-1,6-diazabicyclo[3.2.1]octane-2-carboxamide as described in this application that are ≧95% pure. For example, the forms may be ≧95%, ≧96%, ≧97%, ≧98% or ≧99% pure.

In some embodiments, the Form I of sodium salt of (1R,2S,5R)-7-oxo-6-sulphooxy-1,6-diazabicyclo[3.2.1]octane-2-carboxamide is isolated in a substantially pure form. In other embodiments, the Form II of sodium salt of (1R,2S,5R)-7-oxo-6-sulphooxy-1,6-diazabicyclo[3.2.1]octane-2-carboxamide is isolated in a substantially pure form. In still other embodiments, the Form III of sodium salt of (1R,2S,5R)-7-oxo-6-sulphooxy-1,6-diazabicyclo[3.2.1]octane-2-carboxamide is isolated in a substantially pure form. In other examples, the Form IV or Form V of sodium salt of (1R,2S,5R)-7-oxo-6-sulphooxy-1,6-diazabicyclo[3.2.1]octane-2-carboxamide is isolated in a substantially pure form. The Forms described herein may have purity of more than about 90%, about 91%, about 92%, about 93%, about 94%, about 95%, about 96%, about 97%, about 98%, or about 99% by weight. In specific embodiments, the forms may have a purity of more than about 95% by weight. For example, the forms may be ≧95%, ≧96%, ≧97%, ≧98% or ≧99% pure.

Processes

In another aspect, the present invention provides processes for preparing the crystalline forms of trans-7-oxo-6-(sulphooxy)-1,6-diazabicyclo[3,2,1]octane-2-carboxamide sodium salt (e.g., NXL-104) described in this application.

For example, the present invention relates to a method for the preparation of the sodium salt of the (1R,2S,5R)-7-oxo-6-sulphooxy-1,6-diazabicyclo[3.2.1]octane-2-carboxamide enantiomer shown below:

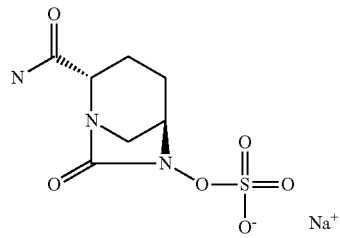 [SMILES: NC(=O)[C@@H]1CC[C@@H]2CN1C(=O)N2OS(=O)(=O)[O-] ; [Na+]]

In exemplary embodiments, tetrabutylammonium salt of (1R,2S,5R)-7-oxo-6-sulphooxy-1,6-diazabicyclo[3.2.1]octane-2-carboxamide is treated in a (1-6 C) alkanol containing between 0 and 50% water, with a sodium salt that is soluble in the reaction mixture, and then the crystals obtained are isolated. The sodium salt used may be an acetate, a butyrate, a hexanoate, an ethyl-hexanoate or a dodecylsulphate. In specific embodiments, the salt may be 2-ethyl-hexanoate. The process of the reaction is an equilibrium that is displaced by the crystallization of the expected sodium salt, which can be applied advantageously on an industrial scale, making the method particularly useful. Either the alcoholic solution of sodium 2-ethylhexanoate is added to the alcoholic solution of the tetrabutylammonium salt, or vice versa. The (1-6 C) alkanol may be ethanol, propanol or linear or branched butanol. In specific embodiments, the alkanol may be ethanol. The operation may be carried out in the presence of 0 to 10% water, at a temperature between 15 and 40° C.

The invention in particular relates to a method as defined above, for the preparation of the sodium salt of (1R,2S,5R)-7-oxo-6-sulphooxy-1,6-diazabicyclo[3.2.1]octane-2-carboxamide, in an anhydrous form called Form I as described herein. In exemplary embodiments, a solution of sodium 2-ethylhexanoate in pure ethanol is added to a solution of the tetrabutylammonium salt of (1R,2S,5R)-7-oxo-6-sulphooxy-1,6-diazabicyclo[3.2.1]octane-2-carboxamide in an ethanol/water mixture in such a way that the final proportion of water is from 0 to 5 wt. % of the solvent, operating at a temperature from 10 to 40° C., in the presence of seed crystals of Form I or Form II as described herein. The parameters, such as the proportion of water in the reaction mixture, the duration of addition, the temperature and the concentration are interdependent on the crystalline form. In order to obtain pure Form I, it is preferable to operate in the presence of seed crystals of Form I and of a final proportion of water less than 2%, introducing the solution of sodium 2-ethylhexanoate over a period of 1 to 7 hours and operating at a temperature from 10 to 40° C., and more preferably, 30 to 35° C. In other embodiments, an ethanolic solution of the tetrabutylammonium salt of (1R,2S,5R)-7-oxo-6-sulphooxy-1,6-diazabicyclo[3.2.1]octane-2-carboxamide is added to an ethanol/water mixture of sodium 2-ethylhexanoate, moreover operating under the same conditions of solvent and temperatures as those described above.

The invention also relates to a method as defined above, for the preparation of the sodium salt of (1R,2S,5R)-7-oxo-6-sulphooxy-1,6-diazabicyclo[3.2.1]octane-2-carboxamide, in a monohydrate Form called Form II, as described herein. In exemplary embodiments, a solution of sodium 2-ethylhexanoate in pure ethanol is added to a solution of the tetrabutylammonium salt of (1R,2S,5R)-7-oxo-6-sulphooxy-1,6-diazabicyclo[3.2.1]octane-2-carboxamide in an ethanol/water mixture in such a way that the final proportion of water is from 3 to 10 wt. % of the solvent, operating at a temperature from 10 to 40° C. Crystallization is carried out in the absence of seed crystals or by adding seed crystals of Form II. The parameters, such as the proportion of water in the reaction mixture, the duration of addition, the temperature and the concentration act interdependently on the crystalline form. In order to obtain the pure Form II, it is preferable to operate at a temperature from 20 to 35° C. and more preferably, at room temperature, in the presence of seed crystals of the Form II, a final proportion of water greater than 5 wt. % of the solvent, and introducing the solution of sodium 2-ethylhexanoate over a period of 30 minutes to 2 hours.

In other embodiments, an ethanolic solution of the tetrabutylammonium salt of (1R,2S,5R)-7-oxo-6-sulphooxy-1,6-diazabicyclo[3.2.1]octane-2-carboxamide is added to an ethanol/water mixture of sodium 2-ethylhexanoate, operating under the same conditions of solvent and temperatures as those described above.

The invention also relates to a method as defined above, for the preparation of the sodium salt of (1R,2S,5R)-7-oxo-6-sulphooxy-1,6-diazabicyclo[3.2.1]octane-2-carboxamide, in an anhydrous polymorphic called Form IV, as described herein. In exemplary embodiments, an ethanolic solution of sodium 2-ethylhexanoate is added to an ethanolic solution of the tetrabutylammonium salt of (1R,2S,5R)-7-oxo-6-sulphooxy-1,6-diazabicyclo[3.2.1]octane-2-carboxamide, operating at room temperature. Crystallization is carried out in the absence of seed crystals or by adding seed crystals of the polymorphic Form IV or optionally of the Form II. The parameters such as the proportion of water in the reaction mixture, the duration of addition, the temperature and the concentration act interdependently on the crystalline form. In order to obtain pure Form IV, it is preferable to operate in the absence of seed crystals, introducing the solution of sodium 2-ethylhexanoate over a period of 30 minutes or less, and operating at room temperature.

In other embodiments, an ethanolic solution of the tetrabutylammonium salt of (1R,2S,5R)-7-oxo-6-sulphooxy-1,6-diazabicyclo[3.2.1]octane-2-carboxamide is added to an ethanolic solution of sodium 2-ethylhexanoate, operating under the same conditions of solvent and temperature as those described above.

The invention also relates to processes for making a dihydrate form of the sodium salt of (1R,2S,5R)-7-oxo-6-sulphooxy-1,6-diazabicyclo[3.2.1]octane-2-carboxamide called Form III. In exemplary embodiments, crystals of Form II are suspended in water, and the suspension is then left to evaporate slowly in a humid atmosphere. Crystals can also been obtained by trituration of crystals of Form II in water or in an alkanol-water mixture, or by conversion, in a humid atmosphere, of the anhydrous Form I and Form IV to the monohydrated Form II and then to the dihydrated Form III. This Form III is particularly stable at higher humidities.

In exemplary embodiments, the methods comprise warming a filtered solution of the tetrabutylammonium salt of trans-7-oxo-6-(sulfooxy)-1,6-diazabicyclo[3,2,1]octane-2-carboxamide in ethanol and mixing with a filtered solution of sodium 2-ethylhexanoate in ethanol, cooling the mixture, isolating the crystals by filtration and drying the crystals under vacuum. For example, Form I may be prepared by this method.

In another example, 3.798 g of sodium 2-ethyl hexanoate (1.2 equivalent), 100 ml ethanol and 5 ml distilled ionized water are stirred until full dissolution at room temperature. 10 g sulfaturamide dissolved in 90 ml ethanol is added in 45 minutes and the addition funnel is rinsed with 5 ml ethanol. The suspension is stirred for 18 h at room temperature and cooled to 5° C. The suspension is stirred for 1-2 h at 5° C. and filtered by gravity. The solid is washed with 2.5% aqueous ethanol (3×30 ml) and dried at 20 mbar at 20° C. for 2-18 h until constant weight.

In other embodiments, the methods comprise mixing Form I seed crystals with a filtered and warmed solution of tetrabutylammonium salt of trans-7-oxo-6-(sulfooxy)-1,6-diazabicyclo[3,2,1]octane-2-carboxamide in ethanol in a reactor and adding a filtered solution of sodium 2-ethylhexanoate in ethanol, stirring the mixture, cooling the mixture, isolating the crystals by filtration, washing with ethanol and drying the crystals under vacuum.

In still other embodiments, the methods comprise mixing a warmed and filtered solution of tetrabutylammonium salt of trans-7-oxo-6-(sulfooxy)-1,6-diazabicyclo[3,2,1]octane-2-carboxamide in isobutanol with a filtered solution of sodium 2-ethylhexanoate in isobutanol, cooling the mixture, isolating the crystals by filtration; washing with an ice-cold mixture of isobutanol and water and drying the crystals under vacuum.

In exemplary embodiments, the methods comprise mixing a solution of sulfaturamide (SU) in ethanol with a solution of sodium 2-ethylhexanoate (SEH) in ethanol. The crystalline form may be obtained under anhydrous conditions using anhydrous SU and SEH. For example, Form IV may be prepared by this method.

In further embodiments, the Form I crystals may be vortexed in a salt solution, e.g., sodium chloride, to provide Form III.

In some embodiments, seed crystals of Form I may be obtained by dissolving the amorphous sodium salt of (1R,2S,5R)-7-oxo-6-sulphooxy-1,6-diazabicyclo[3.2.1]octane-2-carboxamide in 33 volumes of methanol, adding 10 volumes of ethanol at 60° C., concentration of the solution to about 10 volumes at room temperature and then distillation of the methanol to constant volume, still at room temperature, with ethanol (25 volumes are added). The Form I thus obtained is filtered and then dried.

In some embodiments, seed crystals of Form II may be obtained by adding, over forty-five minutes, 19 volumes of ethanol to a solution of the amorphous sodium salt of (1R,2S,5R)-7-oxo-6-sulphooxy-1,6-diazabicyclo[3.2.1]octane-2-carboxamide in one volume of water, cooling to 5° C. in one hour and then holding at this temperature, filtration and finally drying.

In some embodiments, sulphaturamide or tetrabutylammonium salt of (1R,2S,5R)-7-oxo-6-(sulphooxy)-1,6-diazabicyclo[3.2.1]octane-2-carboxamide may be prepared by chiral resolution of its racemic precursor trans-7-oxo-6-(phenylmethoxy)-1,6-diazabicyclo[3.2.1]octane-2-carboxamide, the preparation of which is described in Example 33a Stage A in Application WO 02/10172. In exemplary embodiments, injection of 20 µl of a sample of 0.4 mg/mL of trans-7-oxo-6-(sulphooxy)-1,6-diazabicyclo[3.2.1]octane-2-carboxamide, eluted on a Chiralpak ADH column (5 µm, 25 cm×4.6 mm) with heptane-ethanol-diethylamine mobile phase 650/350/0.05 vol at 1 mL/min makes it possible to separate the (1R,2S,5R) and (1S,2R,5S) enantiomers with retention times of 17.4 minutes and 10.8 minutes respectively. The sulphaturamide is then obtained by conversion according to the conditions described in Example 33a Stage B then Stage C and finally in Example 33b of Application WO 02/10172.

In other embodiments, the sulphaturamide can be prepared from the mixture of the oxalate salt of (2S)-5-benzyloxyamino-piperidine-2-carboxylic acid, benzyl ester (mixture (2S,5R)/(2S,5S)~50/50) described in application FR2921060.

For example, the preparation may proceed in the following stages:

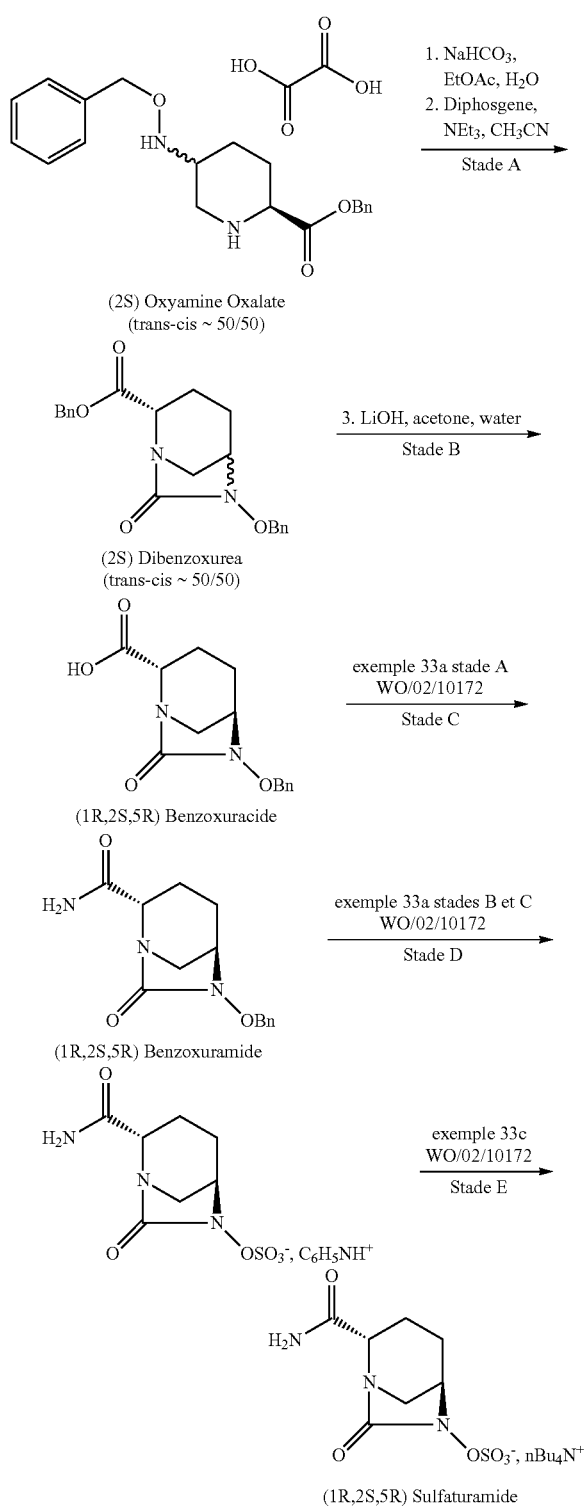

Stade = Stage; exemple = example; et = and; Benzoxuracide = Benzoxuracid

In stage A, dibenzoxurea or (2S)-7-oxo-6-(2-phenylmethoxy)-1,6-diaza-bicyclo[3.2.1]octane 2-benzyl 2-carboxylate is prepared. A 10% saturated aqueous solution of sodium bicarbonate (16 L) is added to a suspension of the oxalate salt of (2S)-5-benzyloxyamino-piperidine-2-carboxylic acid, benzyl ester (mixture (2S,5R)/(2S,5S) 50/50) described in application FR2921060 (2 kg, 4.65 mol) in water (12 L) and ethyl acetate (10 L). The aqueous phase is separated and then re-extracted with ethyl acetate (8 L). The organic phases are combined, washed with water (4 L) and then dried over sodium sulphate (2 kg). The solution is filtered and then concentrated in order to replace the ethyl acetate with acetonitrile (35 L). The solution is cooled to 0-5° C. before adding triethylamine (1.25 L) and then diphosgene (290 mL). The reaction mixture is stirred at 0-5° C. for one hour before adding N,N-dimethylaminopyridine (270 g). After stirring for two hours at room temperature, the reaction mixture is concentrated and then diluted with dichloromethane (15 L). The solution is added to a 20% aqueous solution of ammonium chloride (15 L). The organic phase is isolated. The aqueous phase is re-extracted with dichloromethane (4 L). The organic phases are combined, dried over sodium sulphate and concentrated to dryness to produce the expected compound (1645 g, yield 96% as is, weight/weight).

In stage B, benzoxuracid or (1R,2S,5R)-7-oxo-6-(phenylmethoxy)-1,6-diazabicyclo[3.2.1]octane-2-carboxylic acid and its cyclohexylamine salt is prepared. A solution of lithium hydroxide (79.2 g, 3.3 mol) in water (3.3 L) is added in 30 minutes to a stirred solution at 0-5° C. of the compound obtained in Stage A (1.028 kg, 2.80 mol) in water (10.3 L) and tetrahydrofuran (1.5 L). The reaction mixture is stirred for 1.5 h before adding a mixture of isopropyl ether-ethyl acetate (8/2 vol/vol, 9.25 L). The aqueous phase is isolated at room temperature. The organic phase is extracted with water (2×2.57 L). The aqueous phases are combined and then washed with a mixture of isopropyl ether-ethyl acetate (8/2 vol/vol, 2 L). The aqueous solution is stirred with ethyl acetate (10.3 L), acidified with 2N hydrochloric acid (1.9 L) to pH 2 and then saturated with sodium chloride (4.8 kg). The aqueous phase is isolated and re-extracted with ethyl acetate (5.14 L). The organic phases are combined and dried over sodium sulphate (1 kg). The solution is concentrated under vacuum at 40° C. to produce the expected compound (473 g, 61% yield as is, weight/weight).

The cyclohexylamine salt is prepared according to the method described in Example 32b of Application WO 02/10172.

In stage C, benzoxuramide or (1R,2S,5R)-7-oxo-6-(phenylmethoxy)-1,6-diazabicyclo[3.2.1]octane-2-carboxamide may be prepared. This operation is carried out under the conditions described in Example 33a Stage A of Application WO 02/10172 starting with the compound obtained in Stage B above to obtain the expected compound.

In stages D and E, sulphaturamide is prepared. This operation is carried out starting with the compound obtained in Stage C above, under the conditions described in Example 33a Stage B and then Stage C and finally in Example 33b of Application WO 02/10172. The expected compound is obtained in solid form.

In some embodiments, sodium salt of the amorphous (1R, 2S,5R)-7-oxo-6-(sulphooxy)-1,6-diazabicyclo[3.2.1]octane-2-carboxamide enantiomer may be prepared. For example, a solution of sulphaturamide (6.92 kg, 13.66 mol) in water (56 L) is eluted on a column of Dowex 50WX8 resin (83 kg, 100-200 mesh) preconditioned by elution of an aqueous solution of sodium hydroxide and then washing with water until a neutral pH is reached. The fractions containing the product are combined, filtered, weighed (76 kg net) and then lyophilized to produce the expected sodium salt in amorphous form (3.72 kg, yield 94.8%, HPLC purity >99%).

WO 02/10172 describes the preparation of the racemic sodium salt of trans-7-oxo-6-sulphooxy-1,6-diazabicyclo [3.2.1]octane-2-carboxamide, which is obtained indirectly from a compound described in Example 33b of WO 02/10172, by exchange of the tetrabutylammonium counterion with sodium, eluting an aqueous solution of the salt on ion exchange resin, treated beforehand with sodium hydroxide.

The sodium salt is obtained in solid form, after elimination of the water. The racemic product crystallizes as mentioned in Example 33c of WO 02/10172. Concentration to dryness is carried out in the laboratory by evaporation. In practice, the water is removed by lyophilisation to obtain a homogeneous solid form. This solid form is hygroscopic and of low density, which makes it difficult to handle and store, and consequently makes the method difficult to scale up to an industrial level. In itself, lyophilisation carried out in the laboratory is already a technique that is difficult to scale up to the industrial level. Moreover, the method of ion exchange on resin that precedes it is expensive and of low productivity on account of the large amounts of resin, the dilution with water that is necessary for quantitative ion exchange, the very long duration of the operation and the high energy costs required, and for these reasons as well, the method is difficult to apply industrially.

The present invention relates to a novel and improved method of preparation of the sodium salt of the (1R,2S,5R)-7-oxo-6-sulphooxy-1,6-diazabicyclo[3.2.1]octane-2-carboxamide enantiomer making it possible to obtain said salt in perfectly crystallized and stable form, without having recourse to the ion exchange technique nor to lyophilization under the conditions described above. The method according to the invention therefore offers the dual advantage of simplifying the technique and thus permitting its scaling up to the industrial level, while supplying a crystallized form that is stable, and is easy to isolate, handle, store and formulate.

Compositions

The crystalline forms of the present invention can be administered alone or in combination with an antibacterial agent, such as, for example, ceftaroline or a prodrug of ceftaroline. The present invention includes pharmaceutical compositions comprising the crystalline forms of the invention alone or in combination with an antibacterial agent, such as, for example, ceftaroline or a prodrug of ceftaroline. The compositions may further comprise one or more pharmaceutically acceptable carriers.

In one aspect, the present invention provides a composition comprising a crystalline form of trans-7-oxo-6-(sulphooxy)-1,6-diazabicyclo[3,2,1]octane-2-carboxamide sodium salt (e.g., NXL-104). The crystalline form may be Form I, Form II, Form III, Form IV or Form V of trans-7-oxo-6-(sulphooxy)-1,6-diazabicyclo[3,2,1]octane-2-carboxamide sodium salt (e.g., NXL-104) as described above. In exemplary embodiments, the compositions comprise Form I. In other embodiments, the composition comprises Form II. In still other embodiments, the compositions may comprise Form III, IV or V.

In specific embodiments, the compositions comprise a crystalline form of sodium salt of (1R,2S,5R)-7-oxo-6-sulphooxy-1,6-diazabicyclo[3.2.1]octane-2-carboxamide. For example, the compositions may comprise Form I. In other examples, the compositions may comprise Form II. In still other examples, the compositions may comprise Form III, Form IV or Form V.

The compositions comprising trans-7-oxo-6-(sulphooxy)-1,6-diazabicyclo[3,2,1]octane-2-carboxamide sodium salt (e.g., NXL-104) may comprise related substances that are process impurities or degradants of NXL-104. For example, the compositions may comprise a decarbonyl compound or a disulfate compound.

In some embodiments, the compositions may comprise a crystalline form of trans-7-oxo-6-(sulphooxy)-1,6-diazabicyclo[3,2,1]octane-2-carboxamide sodium salt (e.g., NXL-104) and less than about 2% of a decarbonyl compound of formula (I):

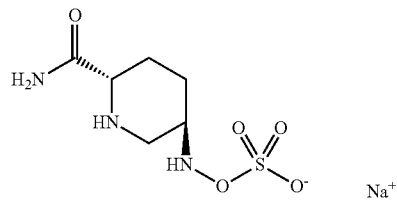

In some embodiments, the compositions comprise about 0.05% to about 1.5% of the decarbonyl compound. In exemplary embodiments, the compositions comprise about 0.05 to about 1.0% of the decarbonyl compound. In other exemplary embodiments, the compositions comprise between about 0.05 to about 0.5% of the decarbonyl compound. For example, the compositions may comprise about 0.1, about 0.2, about 0.3, about 0.4 or about 0.5% of the decarbonyl compound.

In some embodiments, the compositions may comprise the crystalline form and less than about 2% of a disulfate compound of the formula (II):

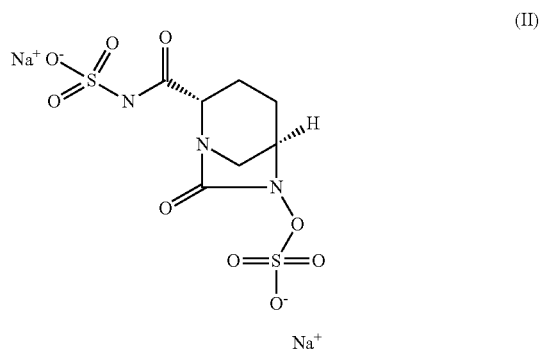

In some embodiments, the compositions may comprise a crystalline form of trans-7-oxo-6-(sulphooxy)-1,6-diazabicyclo[3,2,1]octane-2-carboxamide sodium salt (e.g., NXL-104) and ceftaroline or a prodrug of ceftaroline. The prodrug of ceftaroline may be a phosphono prodrug, such as, ceftaroline fosamil. The ceftaroline fosamil may be anhydrous. In other embodiments, the ceftaroline fosamil may be a monohydrate. In still other embodiments, the ceftaroline fosamil may be a solvate, such as, an acetic acid solvate or a propionic acid solvate.

In exemplary embodiments, the compositions may comprise Form I of trans-7-oxo-6-(sulphooxy)-1,6-diazabicyclo[3,2,1]octane-2-carboxamide sodium salt (e.g., NXL-104) and ceftaroline fosamil. In other exemplary embodiments, the compositions may comprise Form II of trans-7-oxo-6-(sulphooxy)-1,6-diazabicyclo[3,2,1]octane-2-carboxamide sodium salt (e.g., NXL-104) and ceftaroline fosamil. In still other exemplary embodiments, the compositions may comprise Form III, IV or V of trans-7-oxo-6-(sulphooxy)-1,6-diazabicyclo[3,2,1]octane-2-carboxamide sodium salt (e.g., NXL-104) and ceftaroline fosamil.

In some embodiments, the compositions may comprise a crystalline form of trans-7-oxo-6-(sulphooxy)-1,6-diazabicyclo[3,2,1]octane-2-carboxamide sodium salt (e.g., NXL- 104) and ceftaroline fosamil and less than about 10% of total impurities. The impurities may include, but are not limited, to process impurities and degradants of the crystalline form or ceftaroline fosamil. The impurities related to the crystalline form include decarbonyl compound of Formula (I) and disulfate compound of Formula (II).

The impurities related to ceftaroline fosamil include ceftaroline related substances that may be process impurities or degradants of ceftaroline fosamil. Examples of such ceftaroline fosamil related substances are listed below.

U1 refers to ring opened ceftaroline of Formula (III):

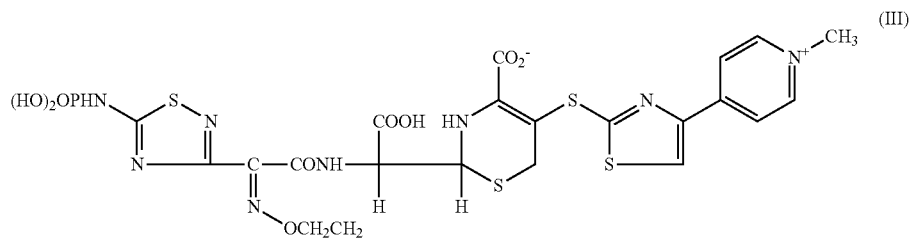

U2 refers to diphosphoric-type ceftaroline of Formula (IV):

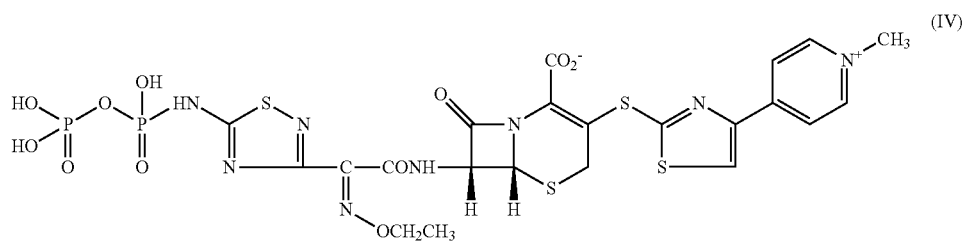

U3 refers to ceftaroline (active metabolite) of Formula (V):

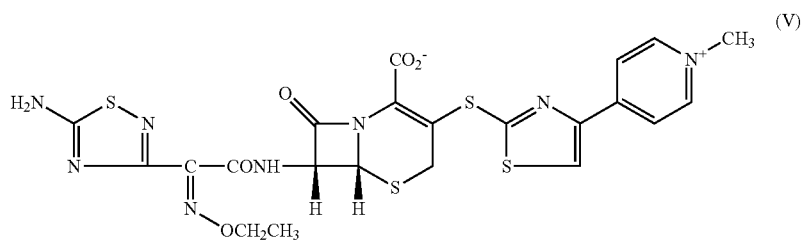

U4 refers to dimer of ceftaroline acetate of Formula (VI):

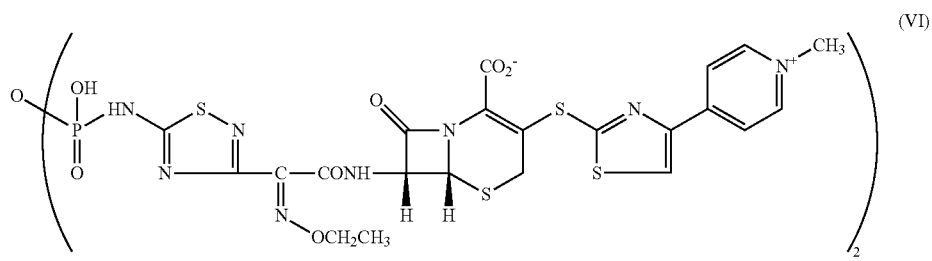

U5 refers to delta 2-type ceftaroline acetate of Formula (VII):
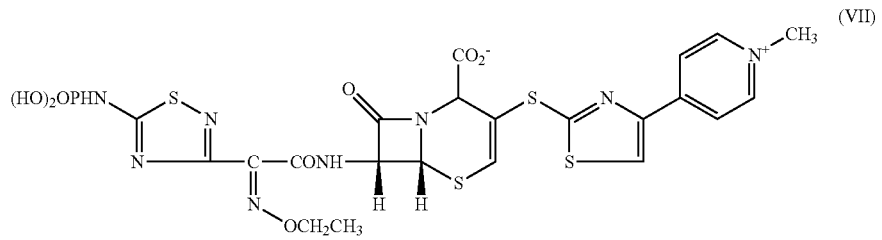
U6 refers to a ring-opened ceftaroline of Formula (VIII):
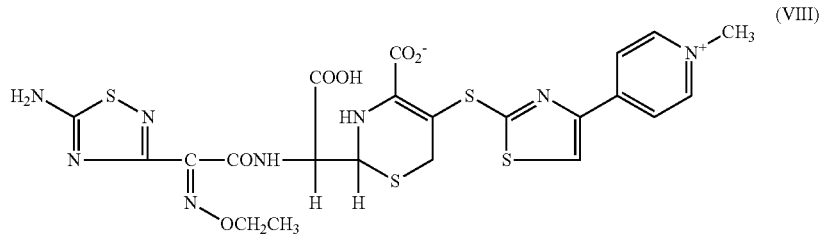
U7 refers to amide-type U-1 of Formula (IX):
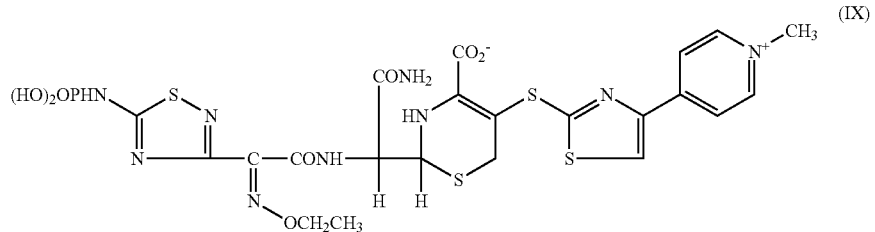
U8 refers to des-methyl-type ceftaroline acetate of Formula (X):
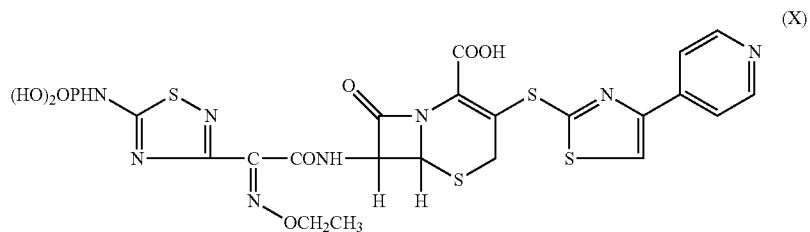

U9 refers to acetyl-type ceftaroline acetate of Formula (XI):

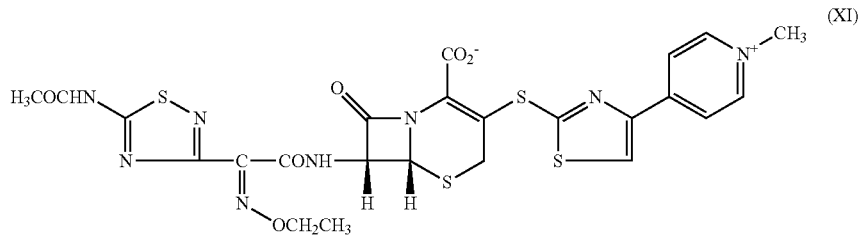

Adduct refers to an adduct of ceftaroline and L-arginine of Formula (XII)

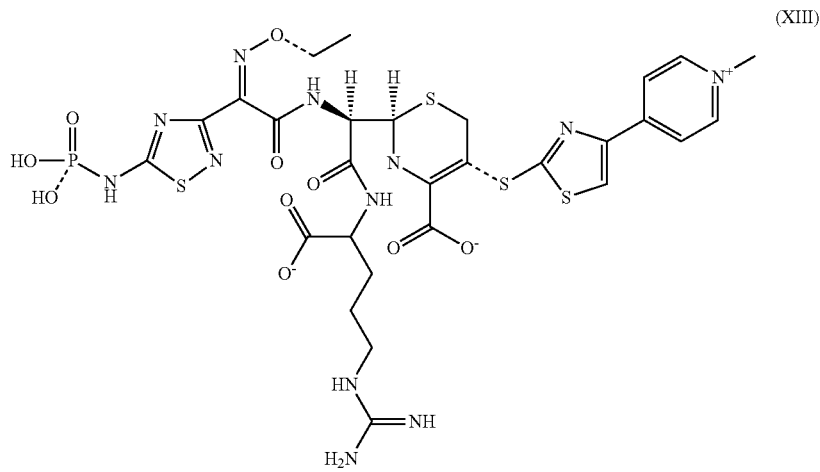

In some embodiments, the compositions comprise a crystalline form of trans-7-oxo-6-(sulphooxy)-1,6-diazabicyclo[3,2,1]octane-2-carboxamide sodium salt (e.g., NXL-104) and ceftaroline fosamil and less than about 1 to 10% of impurities. In specific embodiments, the compositions may comprise about 0.05 to about 10% of impurities.

In exemplary embodiments, the compositions may comprise less than 5% of impurities. For example, the compositions may comprise less than 0.6% U1; less than 0.6% U2, less than 5% U3, less than 0.2% U4, less than 0.2% U5, less than 0.6% U6, less than 0.2% U7, less than 0.2% U8, less than 1.0% U9, or less than 1.5% adducts.

In exemplary embodiments, the compositions comprise about 0.05 to about 0.2% of U4, U5, U7 or U8. In other exemplary embodiments, the compositions comprise about 0.05 to about 0.6% of U1, U2 or U6. In still other exemplary embodiments, the compositions comprise about 0.05 to about 1% of U9. In certain embodiments, the compositions comprise about 0.05 to about 5% of U9. In other embodiments, the compositions comprise about 0.05 to about 1.5% of adduct.

The present invention provides formulations comprising about 200 mg to 1200 mg of a crystalline form of trans-7-oxo-6-(sulphooxy)-1,6-diazabicyclo[3,2,1]octane-2-carboxamide or a salt thereof (e.g., NXL-104) that provide an in vivo plasma profile for the crystalline form comprising a mean Cmax of less than about 100 ug/ml. For example, the plasma profile comprises a mean Cmax of less than about 80 ug/ml; about 70 ug/ml; about 60 ug/ml; about 50 ug/ml; about 40 ug/ml or about 30 ug/ml. In exemplary embodiments, the plasma profile comprises a mean Cmax of about 10 to about 50 ug/ml. In other embodiments, the plasma profile comprises a mean Cmax of about 20 to about 40 ug/ml.

In further embodiments, the present invention provides compositions comprising about 200 mg to 1200 mg ceftaroline fosamil that provide an in vivo plasma profile for ceftaroline comprising a mean Cmax of less than about 100 ug/ml. For example, the plasma profile comprises a mean Cmax of less than about 80 ug/ml; about 70 ug/ml; about 60 ug/ml; about 50 ug/ml; about 40 ug/ml or about 30 ug/ml. In exemplary embodiments, the plasma profile comprises a mean Cmax of about 10 to about 50 ug/ml. In other embodiments, the plasma profile comprises a mean Cmax of about 10 to about 40 ug/ml.

The present invention provides formulations comprising about 200 mg to 1200 mg of a crystalline form of trans-7-oxo-6-(sulphooxy)-1,6-diazabicyclo[3,2,1]octane-2-carboxamide or a salt thereof (e.g., NXL-104) that provide an in vivo plasma profile for the crystalline form comprising a mean $AUC_{0-\infty}$ of more than about 10 ug h/ml. For example, the plasma profile comprises a mean $AUC_{0-\infty}$ of about 10 to 500 ug h/ml; about 10 to 400 ug h/ml ug h/ml; about 10 to 300 ug h/ml; about 10 to 200 ug h/ml or about 10 to 100 ug h/ml. In exemplary embodiments, the plasma profile comprises a mean $AUC_{0-\infty}$ of about 10 to 200 ug h/ml. In further embodiments, the present invention provides compositions comprising about 200 mg to 1200 mg ceftaroline fosamil that provide an in vivo plasma profile for ceftaroline comprising a mean $AUC_{0-\infty}$ of more than about 10 ug h/ml. For example, the plasma profile comprises a mean $AUC_{0-\infty}$ of about 10 to 500 ug h/ml; about 10 to 400 ug h/ml ug h/ml; about 10 to 300 ug h/ml; about 10 to 200 ug h/ml or about 10 to 100 ug h/ml. In exemplary embodiments, the plasma profile comprises a mean $AUC_{0-\infty}$ of about 10 to 200 ug h/ml.

The present invention provides formulations comprising about 200 mg to 1200 mg of a crystalline form of trans-7-oxo-6-(sulphooxy)-1,6-diazabicyclo[3,2,1]octane-2-carboxamide or a salt thereof (e.g., NXL-104) that provides an in vivo plasma profile for the crystalline form comprising a mean Tmax of more than about 10 min. For example, the plasma profile comprises a mean Tmax of more than about 15 minutes, 30 minutes, 45 minutes, 1 hour, 1.5 hours or about 2 hours. In exemplary embodiments, the plasma profile comprises a mean Tmax of about 30 minutes to about 2 hours. In further embodiments, the present invention provides compositions comprising about 200 mg to 1200 mg ceftaroline fosamil that provide an in vivo plasma profile for ceftaroline comprising a mean Tmax of more than about 10 min. For example, the plasma profile comprises a mean Tmax of more than about 15 minutes, 30 minutes, 45 minutes, 1 hour, 1.5 hours or about 2 hours. In exemplary embodiments, the plasma profile comprises a mean Tmax of about 30 minutes to about 2 hours.

The compositions may comprise the crystalline forms in combination with other antibacterial agents. Some examples of antibacterial agents that may be combined with the crystalline forms, include, but are not limited to, antibiotics of the β-lactamine type, for example, penams, penems, cephems, carbacephems, oxacephems, cephamycins, penicillins such as amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin or pivampicillin, cephalosporins such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, or cefditoren, pivoxil, cefuroxime, cefuroxime axetil, loracarbacef or latamoxef, carbapenems such as imipenem, meropenem, biapenem or panipenem and also monobactams such as aztreonam and carumonam, as well as their salts.

In exemplary embodiments, the compositions may comprise the crystalline form in combination with an antibacterial agent, such as, ceftazidime. For example, the compositions may comprise Form I and ceftazidime, Form II and ceftazidime, Form III and ceftazidime, Form IV and ceftazidime or Form V and ceftazidime.

Numerous standard references are available that describe procedures for preparing various compositions suitable for administering the compounds according to the invention. Examples of potential compositions and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The compositions may be solid or liquid and be presented in the pharmaceutical forms, such as for example, plain or sugar-coated tablets, gelatin capsules, granules, suppositories, injectable preparations, ointments, creams, gels, and prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

Various solid oral dosage forms can be used for administering the crystalline forms of the invention including such solid forms as tablets, gelcaps, capsules, caplets, granules, lozenges and bulk powders. The crystalline forms of the present invention can be administered alone or combined with various pharmaceutically acceptable carriers, diluents (such as sucrose, mannitol, lactose, starches) and excipients known in the art, including, but not limited to suspending agents, solubilizers, buffering agents, binders, disintegrants, preservatives, colorants, flavorants, lubricants and the like. Time release capsules, tablets and gels may also be used in administering the crystalline forms of the present invention.

Various liquid oral dosage forms can also be used for administering the crystalline forms of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The crystalline forms of the present invention may be injected, for example, intravenously, in the form of an isotonic sterile solution. Other preparations are also possible.

The compositions may also be presented in the form of a lyophilisate intended to be dissolved extemporaneously in an appropriate vehicle, e.g., apyrogenic sterile water.

Suppositories for rectal administration of the crystalline forms of the present invention can be prepared by mixing the compound with a suitable excipient such as cocoa butter, salicylates and polyethylene glycols.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

Methods of Treatment

In one aspect, the present invention provides methods of treating bacterial infections comprising administering a crystalline form of trans-7-oxo-6-(sulphooxy)-1,6-diazabicyclo[3,2,1]octane-2-carboxamide sodium salt alone (e.g., NXL-104) or in combination with an antibacterial agent, such as, ceftaroline or a prodrug of ceftaroline.

The bacterial infections include, but are not limited to, complicated skin and structure infection, community acquired pneumonia, complicated urinary tract infections and complicated intra-abdominal infections (cIAIs). Complicated intra-abdominal infections include infections requiring surgical intervention and infections that extend beyond the hollow viscus into the peritoneal space.

In some embodiments, the community acquired pneumonia may be due to a microorganism, such as, *Streptococcus*,

*Staphylococcus, Haemophilus, Klebsiella, Escherichia* and *Moraxella*. In further embodiments, the community acquired bacterial pneumonia may be due to a microorganism, including, but not limited to, *Streptococcus pneumoniae, Staphylococcus aureus, Haemophilus influenzae, Haemophilus parainfluenzae, Klebsiella pneumoniae, Escherichia coli* and *Moraxella catarrhalis*. In other embodiments, the community acquired pneumonia may be due to *Enterobacter, Proteus* or *Serratia*. In further embodiments, the community acquired bacterial pneumonia may be due to *Enterobacter aerogenes, Proteus mirabilis* or *Serratia marcescens*.

In exemplary embodiments, the microorganism may be *Streptococcus pneumoniae*. The strain of *Streptococcus pneumoniae* may be penicillin-susceptible, penicillin-resistant or multidrug resistant. In exemplary embodiments, the microorganism may be *Streptococcus pneumoniae* serotype 19A. In some embodiments, the community acquired pneumonia may be associated with concurrent bacteremia. In other exemplary embodiments, the microorganism may be *Staphylococcus aureus*. The strain or isolate of *Staphylococcus aureus* may be methicillin-susceptible or methicillin-resistant. In still other exemplary embodiments, the microorganism may be *Haemophilus influenzae, Klebsiella pneumoniae* or *Escherichia coli*. In exemplary embodiments, the microorganism may be a β-lactamase-nonproducing ampicillin-resistant (BLNAR) strain of *Haemophilus influenzae*.

In some embodiments, the methods comprise administering one or more of the crystalline forms of trans-7-oxo-6-(sulphooxy)-1,6-diazabicyclo[3,2,1]octane-2-carboxamide sodium salt (e.g., NXL-104), for example, Form I, II, III, IV or V as described above. In exemplary embodiments, the methods comprise administering Form I of trans-7-oxo-6-(sulphooxy)-1,6-diazabicyclo[3,2,1]octane-2-carboxamide sodium salt. In other exemplary embodiments, the methods comprise administering Form II of trans-7-oxo-6-(sulphooxy)-1,6-diazabicyclo[3,2,1]octane-2-carboxamide sodium salt. In still other exemplary embodiments, the methods comprise administering Form III, IV or V of trans-7-oxo-6-(sulphooxy)-1,6-diazabicyclo[3,2,1]octane-2-carboxamide sodium salt.

Some examples of antibacterial agents that may be administered in combination with the crystalline forms described in this application, include, but are not limited to, antibiotics of the β-lactamine type, for example, penams, penems, cephems, carbacephems, oxacephems, cephamycins, penicillins such as amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin or pivampicillin, cephalosporins such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftaroline or a prodrug thereof such as ceftaroline fosamil, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, or cefditoren, pivoxil, cefuroxime, cefuroxime axetil, loracarbacef or latamoxef, carbapenems such as imipenem, meropenem, biapenem or panipenem and also monobactams such as aztreonam and carumonam, as well as their salts.

In exemplary embodiments, the methods include administering the crystalline forms in combination with ceftazidime. In specific embodiments, Form I may be combined with ceftazidime. In other embodiments, Form II may be combined with ceftazidime. In still other embodiments, Form III may be combined with ceftazidime. In other examples, Form IV or V may be combined with ceftazidime.

In some embodiments, the methods comprise administering a composition comprising a crystalline form of trans-7-oxo-6-(sulphooxy)-1,6-diazabicyclo[3,2,1]octane-2-carboxamide sodium salt (e.g., NXL-104) as described above. The composition may further comprise an antibacterial agent, e.g., ceftaroline fosamil as described above.

In other embodiments, the methods comprise administering a crystalline form of trans-7-oxo-6-(sulphooxy)-1,6-diazabicyclo[3,2,1]octane-2-carboxamide sodium salt (e.g., NXL-104) and an antibacterial agent, such as, ceftaroline or a prodrug of ceftaroline. The prodrug of ceftaroline may be a phosphono prodrug, such as, ceftaroline fosamil. In exemplary embodiments, the methods comprise administering Form I of trans-7-oxo-6-(sulphooxy)-1,6-diazabicyclo[3,2,1]octane-2-carboxamide sodium salt and ceftaroline fosamil. In other exemplary embodiments, the methods comprise administering Form II of trans-7-oxo-6-(sulphooxy)-1,6-diazabicyclo[3,2,1]octane-2-carboxamide sodium salt and ceftaroline fosamil. In still other exemplary embodiments, the methods comprise administering Form III, IV or V and ceftaroline fosamil.

The crystalline forms of the present invention can be administered at the same time as the dose of an antibacterial agent, or separately. In exemplary embodiments, the crystalline form may be administered in combination with the antibacterial agent, e.g., ceftaroline fosamil in one composition. In other embodiments, a composition comprising the crystalline form may be administered concurrently with a composition comprising the antibacterial agent (e.g., ceftaroline fosamil).

The dose of the crystalline forms may vary according to several factors, including, but not limited to the type of bacterial infection and the microorganism causing the infection.

In some embodiments, the daily dose of the crystalline form may range from about 0.1 to approximately about 10 g. In specific embodiments, the daily dose of the crystalline form may be about 100 mg to 10 g. In other embodiments, the daily dose of the crystalline form may be about 200 mg to 5 g. In still other embodiments, the daily dose of the crystalline form may be about 200 mg to 2000 mg. In exemplary embodiments, the daily dose of the crystalline form may be about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg and about 2000 mg. In some exemplary embodiments, the daily dose is 500 mg. In other exemplary embodiments, the daily dose is 800 mg. In still other exemplary embodiments, the daily dose is 1200 mg.

In some embodiments, the methods comprise administering the crystalline form in combination with about 100 mg and about 2400 mg of ceftaroline or a prodrug thereof (e.g., ceftaroline fosamil). In further embodiments, ceftaroline or a prodrug thereof may be administered in an amount between about 100 mg and about 1200 mg. In some embodiments, ceftaroline or a prodrug thereof may be administered in an amount between about 200 mg and about 1000 mg. In exemplary embodiments, the amount may be about 100 mg, 200 mg, 300 mg, 400 mg, 500 mg, 600 mg, 700 mg, 800 mg, 900 mg, 1000 mg, 1100 mg or 1200 mg. In certain embodiments, the amount may be about 400 mg. In other embodiments, the amount may be about 600 mg. In still other embodiments, the amount may be about 800 mg. In certain embodiments, the amount may be about 1200 mg.

In some embodiments, the methods comprise administering the crystalline form in combination with between about 100 mg and about 2400 mg of ceftazidime. In further embodiments, ceftazidime may be administered in an amount between about 100 mg and about 1200 mg. In some embodiments, ceftazidime may be administered in an amount between about 200 mg and 1000 mg. In exemplary embodiments, the amount may be about 100 mg, 200 mg, 300 mg, 400 mg, 500 mg, 600 mg, 700 mg, 800 mg, 900 mg, 1000 mg, 1100 mg or 1200 mg. In certain embodiments, the amount may be about 500 mg. In other embodiments, the amount of ceftazidime may be between about 1 g and about 3 g. In some embodiments, the amount may be about 1 g. In other embodiments, the amount may be about 2 g. In still other embodiments, the amount may be about 3 g. In some embodiments, the amount may be between about 4 g and 6 g, for example, about 4 g, about 5 g or about 6 g.

The amount of the crystalline form and antibacterial agent may be administered in a single dose or multiple divided doses per day. For example, the amount may be administered as a single daily dose.

In exemplary embodiments, about 800 mg of Form I, II, III, IV or V of trans-7-oxo-6-(sulphooxy)-1,6-diazabicyclo[3,2,1]octane-2-carboxamide sodium salt may be administered daily with about 800 mg of ceftaroline or a prodrug thereof (e.g., ceftaroline fosamil). In other exemplary embodiments, about 1200 mg of Form I, II, III, IV or V of trans-7-oxo-6-(sulphooxy)-1,6-diazabicyclo[3,2,1]octane-2-carboxamide sodium salt may be administered daily with about 1200 mg of ceftaroline or a prodrug (e.g., ceftaroline fosamil) thereof. In some embodiments, the amount may be administered in two to eight doses per day. For example, about 400 mg of the crystalline form and about 400 mg of ceftaroline or a prodrug thereof (e.g., ceftaroline fosamil) may be administered every 12 hours (i.e. twice a day). In some examples, about 600 mg of the crystalline form and about 600 mg of ceftaroline or a prodrug thereof (e.g., ceftaroline fosamil) may be administered every 12 hours (i.e. twice a day).

In some embodiments, the ratio of the crystalline form to the antibacterial agent may range from about 1:20 to about 10:1. The ratio may vary according to the type of infection and the antibacterial agent. In exemplary embodiments, the ratio of crystalline form to antibacterial agent may be between about 1:10 to 5:1.

In specific embodiments, the methods comprise administering the crystalline form in combination with ceftaroline or a prodrug of ceftaroline, such as, ceftaroline fosamil. In exemplary embodiments, the methods include administering the crystalline form and ceftaroline fosamil in a ratio of about 1:1 to 5:1, such as, for example, 1:1, 2:1, 3:1, 4:1, 5:1. In exemplary embodiments, the methods comprise administering Form I, II, III, IV or V of trans-7-oxo-6-(sulphooxy)-1,6-diazabicyclo[3,2,1]octane-2-carboxamide sodium salt (e.g., NXL-104) and ceftaroline fosamil in a ratio of 1:1. For example, about 400 mg of Form I may be administered in combination with about 400 mg of ceftaroline fosamil. In some embodiments, about 600 mg of Form I may be administered with about 600 mg of ceftaroline fosamil.

The crystalline forms of the present invention may be administered according to patient needs, for example, orally, nasally, parenterally, by inhalation, rectally, vaginally, topically and by ocular administration. Parenteral administration may be intravenous, intra-arterial, intrathecal, intramuscular, subcutaneous, intramuscular, intrasternal or intra-abdominal (e.g., intraperitoneal) etc. In some embodiments, the parenteral administration may be effected by infusion pumps (external or implantable) or any other suitable means appropriate to the desired administration modality.

In exemplary embodiments, the crystalline form and ceftaroline or a prodrug thereof may be administered parenterally. Suitable methods for parenteral administration include, but are not limited to, administering a sterile aqueous preparation of the crystalline form alone or in combination with an antibacterial agent, which preferably is isotonic with the blood of the recipient (e.g., physiological saline solution). Such preparations may include suspending agents and thickening agents and liposomes or other microparticulate systems, which are designed to target the compound to blood components or one or more organs. The preparation may be presented in a unit-dose or multi-dose form.

Ceftaroline or a prodrug thereof (e.g., ceftaroline fosamil) may be administered as a solution or suspension in a solvent, such as water, physiological saline, about a 5% to about 10% sugar (e.g., glucose, dextrose) solution, and combinations thereof. In exemplary embodiments, ceftaroline or a prodrug thereof may be administered intravenously, such as, by infusion. In some embodiments, ceftaroline or a prodrug thereof may be administered by intravenous infusion over one hour. In other embodiments, ceftaroline or a prodrug thereof may be administered through continuous or prolonged intravenous infusion. In still other embodiments, ceftaroline or a prodrug thereof may be administered intramuscularly. For intramuscular administration of higher doses, the injection may occur at two or more intramuscular sites.

In some embodiments, methods of treating community acquired pneumonia may include administering ceftaroline or a prodrug thereof every 4 hours, 6 hours, 8 hours, 12 hours, 18 hours or every 24 hours. For example, ceftaroline or a prodrug thereof may be administered every 12 hours intravenously by infusion over one hour. In other embodiments, the methods may include administering ceftaroline or a prodrug thereof through continuous or prolonged infusion. For example, ceftaroline or a prodrug thereof may be administered by infusion over 2 hours, 3 hours, 4 hours, 5 hours, 6 hours, 7 hours, 8 hours, 9 hours, 10 hours, 11 hours or 12 hours. In other embodiments, the duration of infusion may be more than 12 hours, e.g., 13 hours, 14 hours, 15 hours, 16 hours, 17 hours, 18 hours, 19 hours, 20 hours, 21 hours or 22 hours, 23 hours or 24 hours. For example, about 400 mg of ceftaroline or a prodrug thereof may be administered by infusion over 12 hours. In another example, about 600 mg of ceftaroline or a prodrug thereof may be administered by infusion over 12 hours.

The duration of treatment may depend on the severity and site of infection and the subject's clinical and bacteriological progress. In some embodiments, the treatment may last between about 5 to 14 days. In other embodiments, the treatment may last between about 5 to 7 days. For example, about 400 mg of ceftaroline or a prodrug thereof may be administered every 24 hours for five to fourteen days. In further embodiments, about 400 mg of ceftaroline or a prodrug thereof may be administered every 24 hours for five to ten, days. In other embodiments, about 400 mg of ceftaroline or a prodrug thereof may be administered every 24 hours for five to seven days.

In other embodiments, about 400 mg of ceftaroline or a prodrug thereof may be administered every 12 hours for five to fourteen days. In other embodiments, about 400 mg of ceftaroline or a prodrug thereof may be administered every 12 hours for five to ten days. In still other embodiments, about 400 mg of ceftaroline or a prodrug thereof may be administered every 12 hours for five to seven days.

In other embodiments, about 400 mg of ceftaroline or a prodrug thereof may be administered every 8 hours for five to fourteen days. For example, about 400 mg of ceftaroline or a prodrug thereof may be administered every 8 hours for five to ten days. In further embodiments, about 400 mg of ceftaroline or a prodrug thereof may be administered every 8 hours for five to seven days.

In other embodiments, about 600 mg of ceftaroline or a prodrug thereof may be administered every 24 hours for five to fourteen days. For example, about 600 mg of ceftaroline or a prodrug thereof may be administered every 24 hours for five to ten days. In exemplary embodiments, about 600 mg of ceftaroline or a prodrug thereof may be administered every 24 hours for five to seven days. In some embodiments, about 600 mg of ceftaroline or a prodrug thereof may be administered every 12 hours for five to fourteen days. In other embodiments, about 600 mg of ceftaroline or a prodrug thereof may be administered every 12 hours for five to ten days. In still other embodiments, about 600 mg of ceftaroline or a prodrug thereof may be administered every 12 hours for five to seven days. In further embodiments, about 600 mg of ceftaroline or a prodrug thereof may be administered every 8 hours for five to fourteen days. In some embodiments, about 600 mg of ceftaroline or a prodrug thereof may be administered every 8 hours for five to ten days. In other embodiments, about 600 mg of ceftaroline or a prodrug thereof may be administered every 8 hours for five to seven days.

Unless defined otherwise, all technical and scientific terms used herein generally have the same meaning as commonly understood by one of ordinary skill in the art to which this invention belongs.

NXL-104 refers to the monosodium salt of (1R,2S,5R)-7-oxo-6-sulphooxy-1,6-diazabicyclo[3.2.1]octane-2-carboxamide. The structure of NXL-104 is as shown below:

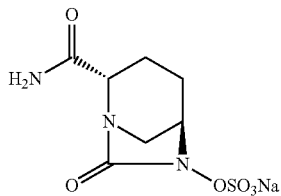

The term "prodrug" means a compound that is a drug precursor, which upon administration to a subject undergoes chemical conversion by metabolic or chemical processes to yield a compound, which is an active moiety. Suitable prodrugs of ceftaroline include, but are not limited to, phosphonocepehem derivatives, such as, e.g., 7β-[2(Z)-ethoxyimino-2-(5-phosphonoamino-1,2,4-thiadiazol-3-yl)acetamido]-3-[4-(1-methyl-4-pyridinio)-2-thiazolylhio]-3-cephem-4-carboxylate.

Solvates of a compound may form when a solvent molecule(s) is incorporated into the crystalline lattice structure of ceftaroline or a prodrug thereof molecule during, for example, a crystallization process. Suitable solvates include, e.g., hydrates (monohydrate, sesquihydrate, dihydrate), solvates with organic compounds (e.g., $CH_3CO_2H$, $CH_3CH_2CO_2H$, $CH_3CN$), and combinations thereof.

The term "substantially pure" means a compound having a purity greater then, e.g., about 90% by weight, for example, greater than about 91% by weight, greater than about 92% by weight, greater than about 93% by weight, greater than about 94% by weight, greater than about 95% by weight, greater than about 96% by weight, greater than about 97% by weight, greater than about 97.5% by weight, greater than about 98% by weight, greater than about 99% by weight, greater than about 99.5% by weight, or greater than about 99.9% by weight.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per practice in the art. Alternatively, "about" with respect to the compositions can mean plus or minus a range of up to 20%, preferably up to 10%, more preferably up to 5%. Alternatively, particularly with respect to biological systems or processes, the term can mean within an order of magnitude, preferably within 5-fold, and more preferably within 2-fold, of a value. Where particular values are described in the application and claims, unless otherwise stated the term "about" means within an acceptable error range for the particular value. For example, when referring to a period of time, e.g., hours, the present values (±20%) are more applicable. Thus, 6 hours can be, e.g., 4.8 hours, 5.5 hours, 6.5 hours, 7.2 hours, as well as the usual 6 hours.

The terms "treat," "treatment," and "treating" refer to one or more of the following: relieving or alleviating at least one symptom of a bacterial infection in a subject; relieving or alleviating the intensity and/or duration of a manifestation of bacterial infection experienced by a subject; and arresting, delaying the onset (i.e., the period prior to clinical manifestation of infection) and/or reducing the risk of developing or worsening a bacterial infection.

The term "community acquired pneumonia" as used herein is equivalent and has been used interchangeably with the term "community acquired bacterial pneumonia."

The term "therapeutically effective" applied to dose or amount refers to that quantity of a compound or pharmaceutical composition that is sufficient to result in a desired activity upon administration to a mammal in need thereof. An "effective amount" means the amount of a compound according to the invention that, when administered to a patient for treating an infection or disease is sufficient to effect such treatment. The "effective amount" will vary depending on the active ingredient, the state of infection, disease or condition to be treated and its severity, and the age, weight, physical condition and responsiveness of the mammal to be treated.

MPTT refers to 4-(1-methylpyridin-1-ium-4-yl)thiazole-2-thiol.

In the examples, ND refers to a not detectable (quantity) and UNK refers to an unknown impurity and w/o U3 refers to total impurities without U3.

In some embodiments, the compounds of the present invention are administered as a mono-therapy. In other embodiments, the compounds of the present invention are administered as part of a combination therapy. For example, a compound of the invention may be used in combination with other drugs or therapies that are used in the treatment/prevention/suppression or amelioration of the diseases or conditions for which compounds of the invention are useful.

Such other drug(s) may be administered, by a route and in an amount commonly used therefore, contemporaneously or sequentially with a compound of the invention. When a compound of the present invention is used contemporaneously with one or more other drugs, a pharmaceutical unit dosage form containing such other drugs in addition to the compound of the invention may be employed. Accordingly, the pharmaceutical compositions of the present invention include those that also contain one or more other active ingredients, in addition to a compound of invention.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Example 1

Preparation and characterization of amorphous trans-7-oxo-6-(sulphooxy)-1,6-diazabicyclo[3,2,1]octane-2-carboxamide sodium salt Amorphous trans-7-oxo-6-(sulphooxy)-1,6-diazabicyclo[3,2,1]octane-2-carboxamide can be prepared as described in U.S. Pat. No. 7,112,592. The XRD pattern was obtained by mounting samples on a sample holder of Rigaku Miniflex X-ray diffractometer with the Kα radiation of copper (λ=1.541 Å). The samples, without grinding, were put on a glass plate and were analyzed at ambient temperature and humidity. Data were collected at 0.05° interval, 2°/minute from 3°-40° 2θ. FIG. 1 shows the X-ray diffraction (XRD) pattern for amorphous trans-7-oxo-6-(sulphooxy)-1,6-diazabicyclo[3,2,1]octane-2-carboxamide sodium salt.

A solution, in a water-acetone mixture (1-1), of the sodium salt of the racemic trans-7-oxo-6-(sulphoxy)-1,6-diazabicyclo[3.2.1]octane-2-carboxamide described in Example 33c of Application WO 02/10172 is evaporated under reduced pressure, under the conditions of concentration described in said example. The salt is obtained in crystallized form. The X-ray spectra ("XRPD diffraction patterns") of the polymorphic Forms were compared. The diffraction pattern of the racemic form obtained according to the prior art is different from each of those of the polymorphic Forms.

Example 2

Preparation and characterization of Form I of trans-7-oxo-6-(sulphooxy)-1,6-diazabicyclo[3,2,1]octane-2-carboxamide sodium salt Method I
A solution of the 5.067 g (10 mmoles) of the tetrabutylammonium salt of trans-7-oxo-6-(sulfooxy)-1,6-diazabicyclo[3,2,1]octane-2-carboxamide in 12.5 ml of 200 proof ethanol and 12.5 ml of 190 proof ethanol was filtered through a 1.6 μm filter and added to a 100 ml jacketed-reactor equipped with magnetic stirrer. The solution was warmed to an internal temperature of 35° C. Separately, a solution of 3.3 g (20 mmoles) of sodium 2-ethylhexanoate in 25 ml 200 proof ethanol was filtered through a 1.6 μm filter. 2.5 ml of this solution was added to the reactor and the mixture was stirred for 1 h at 35° C. Crystallization occurred during this time. The remainder of the sodium 2-ethylhexanoate solution was added over 20 min. The mixture was stirred for an additional 1 h at 35° C., followed by 12 h at 25° C. The mixture was cooled to 0° C. for 2 h. The crystals were isolated by filtration and washed with 10 ml ethanol. The crystals were dried under vacuum at 35° C. for 16 h. 2.72 g of the sodium salt of trans-7-oxo-6-(sulfooxy)-1,6-diazabicyclo[3,2,1]octane-2-carboxamide (Form I) was obtained, corresponding to a yield of 95%.

Method II
A solution of the 50.67 g (100 mmoles) of the tetrabutylammonium salt of trans-7-oxo-6-(sulfooxy)-1,6-diazabicyclo[3,2,1]octane-2-carboxamide in 338 ml of ethanol and 8.33 ml of water was filtered through a 0.45 μm filter and added to a 1 liter jacketed-reactor equipped with overhead stirrer and internal temperature probe. The solution was warmed to an internal temperature of 30° C. 287 mg (1 mmole) of Form I seed crystals were added. A solution of 35.125 g (205 mmoles) of sodium 2-ethylhexanoate in 338 ml ethanol was filtered through a 0.45 μm filter and added to the reactor over 4 h. The mixture was stirred an additional 12 h at 30° C., then cooled to 5° C. for 4 h. The crystals were isolated by filtration and washed with 40 ml ethanol three times. The crystals were dried under vacuum at 20° C. for 4 h. 27.14 g of the sodium salt of trans-7-oxo-6-(sulfooxy)-1,6-diazabicyclo[3,2,1]octane-2-carboxamide (Form I) was obtained, corresponding to a yield of 93.5%.

Method III
A solution of sodium 2-ethylhexanoate (13.12 g, 79 mmol) in ethanol (126 mL) is added over five hours to a solution of sulphaturamide (20 g, 39.5 mmol) in ethanol (126 mL) stirred at 30° C. and seeded with a few crystals of polymorphic Form I. The suspension is stirred overnight. The suspension is cooled to 0-5° C. for 1 to 2 hours, filtered and then washed with ethanol at 5° C. (3×40 mL). The crystals are dried under reduced pressure of 20 mbar at 20° C. The expected polymorphic Form I is obtained (10.79 g, 37.5 mmol, yield 95.1%).

Method IV
A solution of sulphaturamide (10 g, 19.7 mmol) in ethanol (100 ml) is added over forty-five minutes to a solution of sodium 2-ethylhexanoate (3.80 g, 22.9 mmol) in ethanol (95 ml) and water (5 ml; 3.1% of the total weight of the solvent), stirred at room temperature and seeded with a few crystals of polymorphic Form II. The suspension is stirred overnight. The suspension is cooled down to 0-5° C. for 1 to 2 hours, filtered and then washed with ethanol at 5° C. (3×30 ml). The crystals are dried under reduced pressure of 20 mbar at 20° C. The polymorphic Form I is obtained (4.277 g, 14.9 mmol, yield 75.4%).

Figure 2:
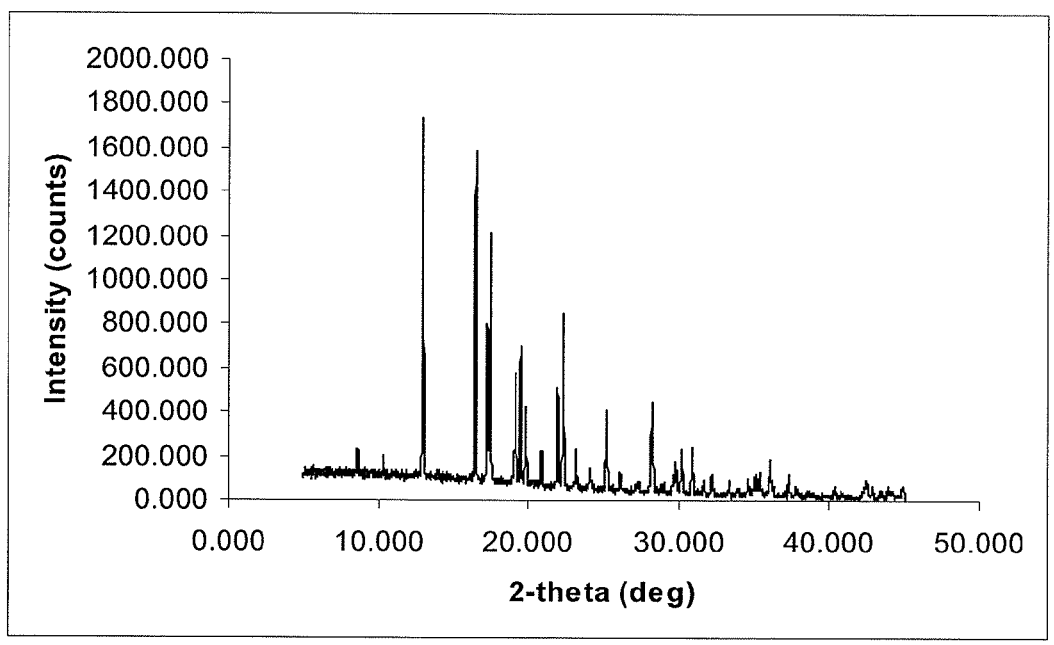
FIG. 2 shows the powder X-Ray diffraction pattern of Form I of trans-7-oxo-6-(sulphooxy)-1,6-diazabicyclo[3,2,1]octane-2-carboxamide sodium salt (NXL-104).

The XRD pattern was obtained as described in Example 1. FIG. 2 shows the XRD pattern for Form I.

Example 3

Preparation and characterization of Form II of trans-7-oxo-6-(sulphooxy)-1,6-diazabicyclo[3,2,1]octane-2-carboxamide sodium salt Method I
A solution of the 10.134 g (20 mmoles) of the tetrabutylammonium salt of trans-7-oxo-6-(sulfooxy)-1,6-diazabicyclo[3,2,1]octane-2-carboxamide in 48.1 ml of isobutanol and 2.53 ml water was filtered through a 1.6 μm filter and added to a 500 ml jacketed-reactor equipped with overhead stirrer and internal temperature probe. The solution was warmed to an internal temperature of 35° C. A solution of 6.65 g (40 mmoles) of sodium 2-ethylhexanoate in 49.5 ml isobutanol and 0.5 ml water was filtered through a 1.6 μm filter and added dropwise to the reactor. Crystallization occurred during the addition. The mixture was stirred for an additional 1 h at 35° C. followed by 16 h at 25° C. The mixture was cooled to 0° C. for 2 h. The crystals were isolated by filtration and washed with an ice-cold mixture of 19.5 ml isobutanol and 0.5 ml water. The crystals were dried under vacuum at 35° C. for 20 h. 5.48 g of the sodium salt of trans-7-oxo-6-(sulfooxy)-1,6-diazabicyclo[3,2,1]octane-2-carboxamide monohydrate (Form II) was obtained, corresponding to a yield of 90%.

Method II

A solution of sodium 2-ethylhexanoate (6.56 g, 39.4 mmol) in ethanol (70 mL) is added over forty-five minutes to a solution of sulphaturamide (10 g, 19.7 mmol) in a mixture of ethanol (63 mL) and water (7 mL, 6.23% of the total weight of the solvent), stirred at 20° C. and seeded with the Form II. The suspension is stirred overnight. The suspension is cooled down to 0-5° C. for 1 to 2 hours, filtered and then washed with aqueous ethanol (5%) cooled down to 5° C. (3×20 mL). The crystals are dried under reduced pressure of 20 mbar at 20° C. The expected Form II is obtained (5.35 g, 17.5 mmol, yield 88.8%).

Method III

A solution of sulphaturamide (1 g, 1.97 mmol) in ethanol (9.5 ml) and water (0.5 ml) is added over thirty minutes to a solution of sodium 2-ethylhexanoate (0.506 g, 3.04 mmol) in ethanol (9.5 ml) and water (0.5 ml). It is stirred at room temperature. The solution (6.23% of the total weight of water) is seeded with a few crystals of Form II to produce a suspension, which is stirred overnight. The suspension is cooled down to 0-5° C. for 1 to 2 hours, filtered and then washed with ethanol at 5° C. (3×6 ml). The crystals are dried under reduced pressure of 20 mbar at 20° C. The expected Form II is obtained (0.378 g, 1.24 mmol, yield 62.7%).

Figure 3:
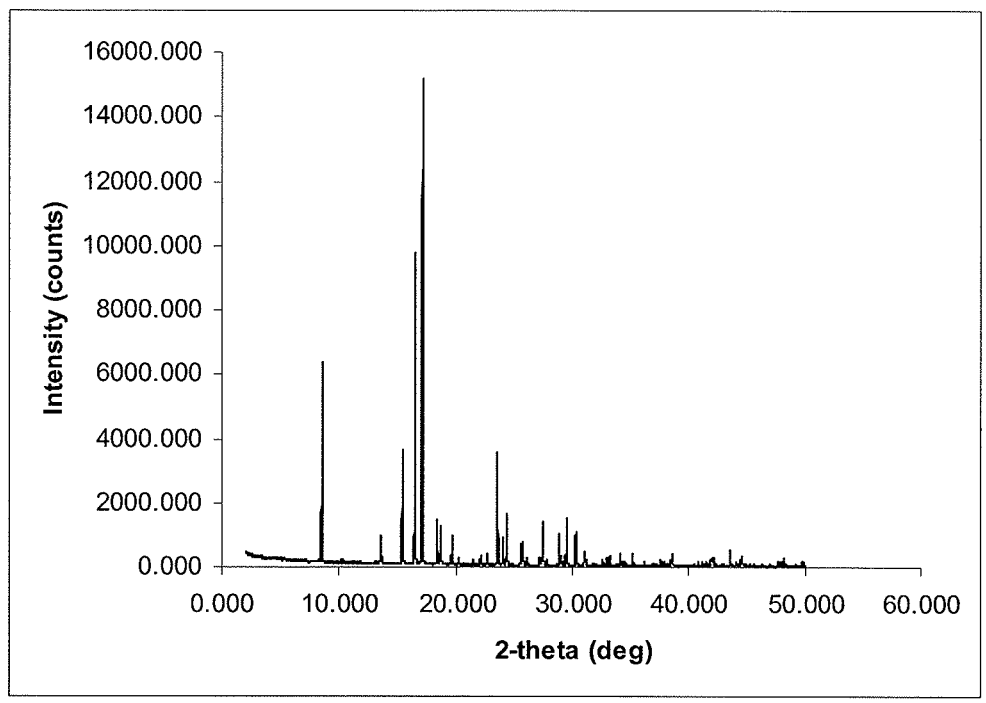
FIG. 3 shows the powder X-Ray diffraction pattern of Form II of trans-7-oxo-6-(sulphooxy)-1,6-diazabicyclo[3,2,1]octane-2-carboxamide sodium salt (NXL-104).

The XRD pattern was obtained as described in Example 1. FIG. 3 shows the XRD pattern for Form II.

Example 4

Preparation and characterization of Form III of trans-7-oxo-6-(sulphooxy)-1,6-diazabicyclo[3,2,1]octane-2-carboxamide sodium salt Form III can be made on mg scale by vortexing Form I (100 mg) in 0.9% aqueous sodium chloride solution (40 µl).

Figure 4:
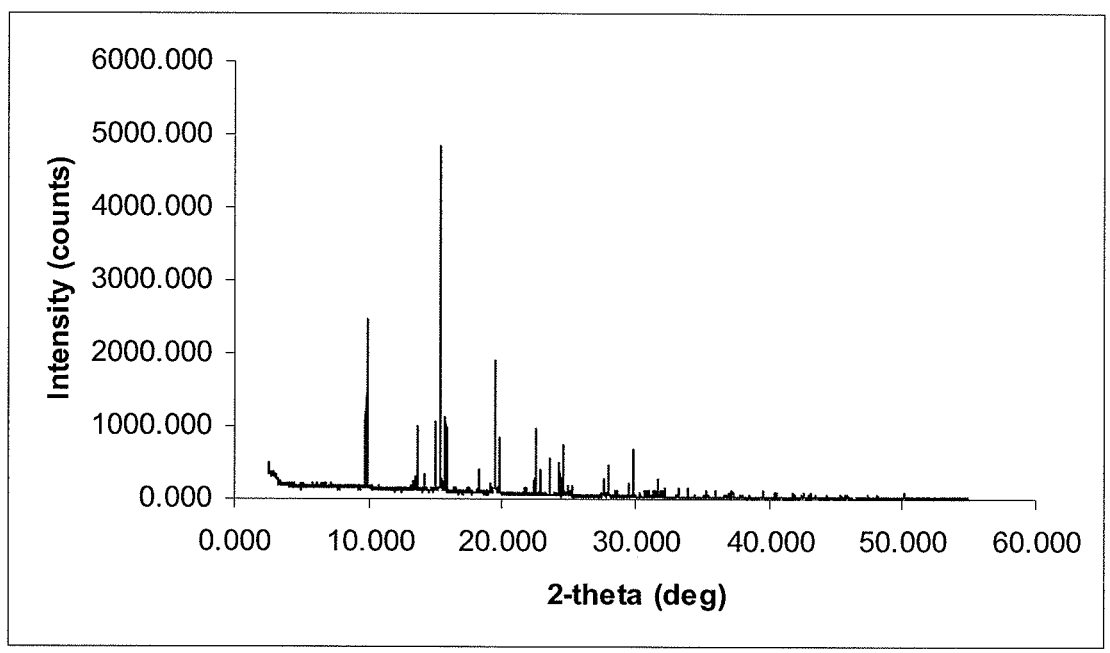
FIG. 4 shows the powder X-Ray diffraction pattern of Form III of trans-7-oxo-6-(sulphooxy)-1,6-diazabicyclo[3,2,1]octane-2-carboxamide sodium salt (NXL-104).

A sample of sodium salt of the (1R,2S,5R)-7-oxo-6-(sulphoxy)-1,6-diazabicyclo[3.2.1]octane-2-carboxamide enantiomer, monohydrate—Form II (1 g) is suspended in water (2 ml). The suspension, unstirred, is left to evaporate slowly at ambient temperature, pressure and humidity. The crystallized solid is recovered after complete evaporation. The expected Form III is obtained (1.056 g). The XRD pattern was obtained as described in Example 1. FIG. 4 shows the XRD pattern for Form III.

Example 5

Preparation and characterization of Form IV of trans-7-oxo-6-(sulphooxy)-1,6-diazabicyclo[3,2,1]octane-2-carboxamide sodium salt Method I Sulfaturamide (SU) is dissolved in ethanol (EtOH). Sodium 2-ethylhexanoate (SEH), dissolved in ethanol, is added rapidly to SU solution. SU, SEH and the byproduct (tetrabutylammonium ethylhexanoate) are all soluble in EtOH, but the sodium salt of NXL-104 has a poor solubility and so crystallizes out of solution. Form IV is obtained under anhydrous conditions (anhydrous SU and SEH) and rapid addition of SEH. Yield was 85% using this process.

Method II

A solution of sodium 2-ethylhexanoate (3.28 g, 19.7 mmol) in ethanol (25 ml) is added over thirty minutes to a solution of sulphaturamide (4 g, 9.87 mmol) in ethanol (25 ml), stirred at 20° C. and seeded with the polymorphic form II. The suspension is stirred overnight. The suspension is filtered and then washed with ethanol at 5° C. (3×10 ml). The solid is dried under reduced pressure of 20 mbar at 20° C. The expected polymorphic form IV is obtained (2.50 g, 8.70 mmol, yield 88.2%).

Figure 5:
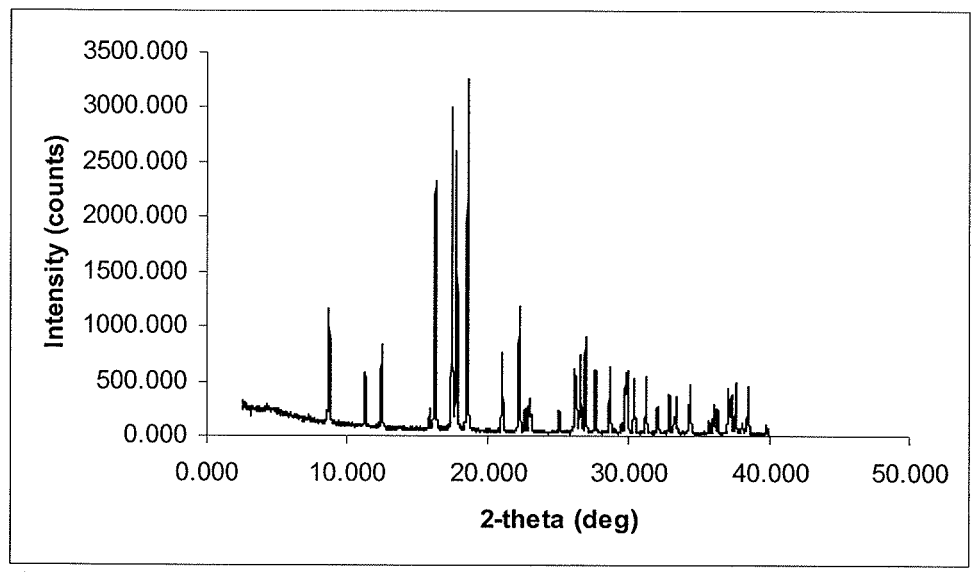
FIG. 5 shows the powder X-Ray diffraction pattern of Form IV of trans-7-oxo-6-(sulphooxy)-1,6-diazabicyclo[3,2,1]octane-2-carboxamide sodium salt (NXL-104).
Figure 6:
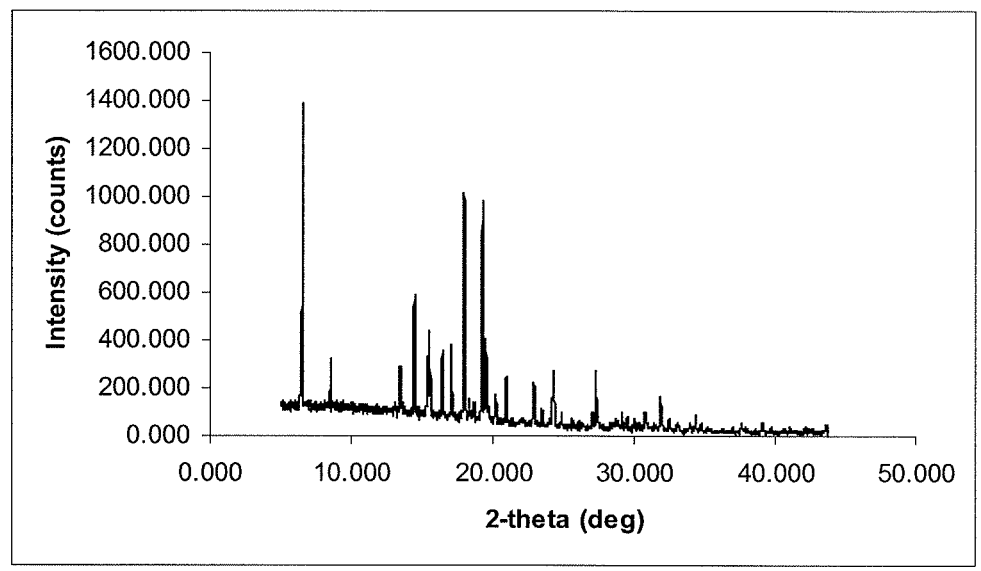
FIG. 6 shows the powder X-Ray diffraction pattern of Form V of trans-7-oxo-6-(sulphooxy)-1,6-diazabicyclo[3,2,1]octane-2-carboxamide sodium salt (NXL-104).

The XRD pattern was obtained as described in Example 1. FIG. 5 shows the XRD pattern for Form IV.

Example 6

Stability of amorphous trans-7-oxo-6-(sulphooxy)-1,6-diazabicyclo[3,2,1]octane-2-carboxamide sodium salt (NXL-104)

A solution containing 400 mg/ml (on free acid basis) trans-7-oxo-6-(sulphooxy)-1,6-diazabicyclo[3,2,1]octane-2-carboxamide sodium salt was prepared by dissolving the compound in water. The solution was then filled into 10 cc Type I glass vials and lyophilized by freezing at −50° C. for 1-4 hours, primary drying at temperatures ranging from −25 to −10° C. for 30-50 hours and pressures from 100 to 400 mTorr and secondary drying at 25° C. for 10-20 hours.

Assay for NXL-104 and Related Substances

NXL-104 and related substances in compositions comprising trans-7-oxo-6-(sulphooxy)-1,6-diazabicyclo[3,2,1]octane-2-carboxamide sodium salt were determined by a reverse phase gradient HPLC method with UV detection at 195 nm.

The Following Parameters were Used for Analysis:
Column: Inertsil ODS-3, 250 mm×4.6 mm, 5 µm
Mobile Phase A: 100 mM $KH_2PO_4$ Solution
Mobile Phase B: Acetonitrile: Water, [50:50 (v:v)]
Flow Rate: 1.0 ml/min
Column Temperature: 25° C.
Autosampler Temperature: 5° C.
Detector/Setting: UV/195 nm
Injection Volume: 10 µL
Run Time: about 25 minutes
Injector Washing Solution: Acetonitrile:Water, [10:90 (v:v)]

Approximate relative retention times (RRT) values for trans-7-oxo-6-(sulphooxy)-1,6-diazabicyclo[3,2,1]octane-2-carboxamide sodium salt and disulfate were 1.00 and 0.37.

The decarbonyl degradation product of trans-7-oxo-6-(sulphooxy)-1,6-diazabicyclo[3,2,1]octane-2-carboxamide sodium salt was determined by a reverse phase gradient HPLC method with UV detection at 195 nm.

The Following Parameters were Used for Analysis:
Column: Inertsil ODS-3, 250 mm×4.6 mm, 5 µm
Mobile Phase A: Deionized Water
Mobile Phase B: 50 mM $KH_2PO_4$ solution: Acetonitrile, [50:50 (v:v)]
Flow Rate: 1.0 ml/min
Column Temperature: 25° C.
Detector/Setting: UV/195 nm
Injection Volume: 10 µL
Run Time (Approximate): 35 minutes
Injector Washing Solution: Acetonitrile:Water, [50:50 (v:v)] (Recommended)

Approximate relative retention time (RRT) for decarbonyl was 0.17.

The stability of amorphous trans-7-oxo-6-(sulphooxy)-1,6-diazabicyclo[3,2,1]octane-2-carboxamide sodium salt stored in a vial stored at 25° C. with a relative humidity of 60% (25° C./60% RH) was evaluated using the NXL-104 assay described above.

Table 1 provides the stability data for amorphous NXL-104 in vial stored at 25° C./60% RH.

TABLE 1

Stability of amorphous NXL-104 in vial stored at 25° C./60% RH

|  | pH | NXL-104 % | Impurities - NXL-104 Related (%) | | |
|---|---|---|---|---|---|
|  |  |  | Decarbonyl | Disulfate | Total Impurities |
| Initial | 7.0 | 106.4 | 0.63 | 0.19 | 0.90 |
| 1 month | 7.3 | 111.3 | 0.46 | 0.19 | 0.89 |
| 3 months | 7.2 | 108.0 | 0.48 | 0.17 | 0.92 |
| 6 months | 7.3 | 106.1 | 0.33 | 0.17 | 0.87 |

Example 7

Stability of amorphous trans-7-oxo-6-(sulphooxy)-1,6-diazabicyclo[3,2,1]octane-2-carboxamide sodium salt (NXL-104) and amorphous ceftaroline fosamil A solution was prepared by dissolving ceftaroline fosamil monohydrate acetic acid solvate (668.4 mg/vial), trans-7-oxo-6-(sulphooxy)-1,6-diazabicyclo[3,2,1]octane-2-carboxamide sodium salt (649.8 mg/vial) and L-Arginine (434.3 mg/vial) in Water for Injection, USP. The concentration of both ceftaroline fosamil (anhydrous and non-solvate) and trans-7-oxo-6-(sulphooxy)-1,6-diazabicyclo[3,2,1]octane-2-carboxamide free acid was 120 mg/ml.

Lyophilization cycle was designed based on the glass transition temperatures of frozen solutions of ceftaroline fosamil monohydrate acetic acid solvate, trans-7-oxo-6-(sulphooxy)-1,6-diazabicyclo[3,2,1]octane-2-carboxamide sodium salt and L-Arginine determined using Differential Scanning calorimetry. 5 ml of the solution was filled into each 20 cc Type I glass vial and lyophilized (Telstar LyoBeta25) by freezing at −50° C. for 1-5 hours, primary drying at temperatures ranging from −40 to −10° C. for 30-50 hours and pressures from 100 to 400 mTorr and secondary drying at 25° C. for 10-20 hours. Intact lyophilized cakes were obtained at the end of the process and the vials were stored at different conditions to monitor stability.

NXL-104 and related substances were measured according to the assay described in Example 6.

Assay for Ceftaroline Fosamil and Related Substances

Ceftaroline fosamil assay and related substances in compositions comprising trans-7-oxo-6-(sulphooxy)-1,6-diazabicyclo[3,2,1]octane-2-carboxamide sodium salt and ceftaroline fosamil were quantified by a gradient method using ultra high performance liquid chromatography (HPLC). The analytical wavelength setting was 245 nm.

The Following Parameters were Used for Analysis:

Analytical Column: Waters Acquity HPLC BEH C18 Column, 2.1×100 mm, 1.7 μm particle size Guard Column: Waters Acquity HPLC BEH C18 VanGuard Pre-Column, 2.1×5 mm, 1.7 μm particle size Mobile Phase A: 100 mM Ammonium Acetate:Acetonitrile (95:5, v:v)

Mobile Phase B: 100 mM Ammonium Acetate:Acetonitrile (60:40, v:v)

Flow Rate: 0.5 ml/min

Column Temperature: 40° C.

Detector: UV/245 nm

Injection Volume: 4 μL,

Injection Type: Partial Loop with Needle Overfill

Weak Needle Wash Solution: Water:Acetonitrile (90:10, v:v)

Strong Needle Wash Solution: Methanol:Acetonitrile:Isopropanol:Water (25:25:25:25, v:v:v:v) with 0.1% Formic Acid Seal Wash Solution: Water:Acetonitrile (95:5, v:v)

Run Time: about 12 minutes

Approximate relative retention times (RRT) for the ceftaroline related substances were as follows:

U1—0.31
U2—0.94
U3—1.57
U4—1.74
U6—0.80
U9—1.78
Adduct—0.66

Tables 2-4 show the stability data for composition comprising amorphous trans-7-oxo-6-(sulphooxy)-1,6-diazabicyclo[3,2,1]octane-2-carboxamide sodium salt (NXL-104) and amorphous ceftaroline fosamil.

TABLE 2

NXL-104 and ceftaroline fosamil assay

|  | pH | NXL-104% | Ceftaroline fosamil % |
|---|---|---|---|
| t-zero | 5.68 | 104.2 | 94.3 |
| 1 month at 40° C./75% RH | 5.67 | 99.5 | 80.3 |
| 3 months at 25° C./60% RH | 5.71 | 101.9 | 87.0 |

TABLE 3

NXL-104 related impurities (%)

|  | Decarbonyl | Total Impurities |
|---|---|---|
| t-zero | ND | 0.17 |
| 1 month at 40° C./75% RH | 0.23 | 1.32 |
| 3 months at 25° C./60% RH | 0.23 | 0.91 |

TABLE 4

Ceftaroline related impurities (%)

|  | U1 | Adduct | U6 | U4 | U7 | U3 | U9 | Total Impurities |
|---|---|---|---|---|---|---|---|---|
| t-zero | 1.01 | 0.57 | 0.10 | 0.03 | 0.02 | 2.59 | 0.03 | 4.52 |
| 1 month at 40° C./75% RH | 6.14 | 2.58 | 0.32 | 0.05 | ND | 3.62 | 0.09 | 14.88 |
| 3 months at 25° C./60% RH | 4.02 | 1.98 | 0.22 | <0.05 | 0.02 | 3.00 | <0.05 | 12.96 |

Amorphous NXL-104 and Amorphous Ceftaroline Fosamil with Stabilizer

A solution was prepared by dissolving ceftaroline fosamil monohydrate acetic acid solvate (668.4 mg/vial), trans-7-oxo-6-(sulphooxy)-1,6-diazabicyclo[3,2,1]octane-2-carboxamide sodium salt (649.8 mg/vial), L-Arginine and/or suitable buffer or other stabilizer in Water for Injection, USP. The concentration of both ceftaroline fosamil (anhydrous and non-solvate) and trans-7-oxo-6-(sulphooxy)-1,6-diazabicyclo[3,2,1]octane-2-carboxamide free acid was 120 mg/ml. Lyophilization cycle was designed based on the glass transition temperatures of frozen solutions of ceftaroline fosamil monohydrate acetic acid solvate, trans-7-oxo-6-(sulphooxy)-1,6-diazabicyclo[3,2,1]octane-2-carboxamide sodium salt and L-Arginine determined using Differential Scanning calorimetry as well as the glass transition temperatures of frozen solutions of the buffer/other stabilizer. 5 ml of the solution was filled into 20 cc Type I glass vial and lyophilized (Telstar LyoBeta25) by freezing at −50° C. for 1-5 hours, primary drying at temperatures ranging from −40 to −10° C. for 40-80 hours and pressures from 100 to 400 mTorr and secondary drying at 25° C. for 10-20 hours. Depending on the formulation, an annealing step was also included before primary drying in order to allow complete ice crystallization or crystallization of excipients. Annealing temperature was between −20° C. and 0° C. and annealing time was 4-12 hours. Intact lyophilized cakes were obtained at the end of the process and the vials were stored at different conditions to monitor stability. Packaging components used were 20 ml Type I glass vial, Gray chlorobutyl-isoprene stopper and Blue Aluminum tear-off seal.

Tables 5-7 show the stability data for a formulation comprising lyophilized ceftaroline fosamil (668.4 mg), arginine (434.3 mg), NXL-104 (649.8 mg) and Kollidon17 (93 mg).

TABLE 5

NXL-104 and ceftaroline fosamil assay

| | pH | NXL-104% | Ceftaroline fosamil % |
|---|---|---|---|
| t-zero | 5.61 | 101.08 | 96.60 |
| 3 months at 40° C./75% RH | 5.43 | 93.2 | 72.4 |

TABLE 6

NXL-104 related impurities (%)

| | Decarbonyl | Total Impurities |
|---|---|---|
| t-zero | 0.61 | 0.76 |
| 3 months at 40° C./75% RH | 0.20 | 3.91 |

TABLE 7

Ceftaroline fosamil related impurities (%)

| | U1 | Adduct | U6 | U2 | U3 | U9 | Total Impurities |
|---|---|---|---|---|---|---|---|
| t-zero | 1.37 | 0.76 | 0.19 | 0.11 | 3.28 | 0.25 | 6.72 |
| 3 months 40° C./ 75% RH | 10.20 | 4.57 | 0.90 | 0.21 | 5.04 | 0.22 | 22.76 |

Four formulations (1-4) comprising amorphous trans-7-oxo-6-(sulphooxy)-1,6-diazabicyclo[3,2,1]octane-2-carboxamide sodium salt and amorphous ceftaroline fosamil were prepared. Table 8 shows the stability data for lyophilized Formulations 1-4.

Formulation 1 (Per Vial)
Ceftaroline fosamil acetate=668.4 mg
NXL-104=649.8 mg
L-Arginine=434.3 mg
Citric acid monohydrate=1.1 mg
Trisodium citrate dihydrate=27.9 mg
Formulation 2 (Per Vial)
Ceftaroline fosamil acetate=668.4 mg
NXL-104=649.8 mg
L-Arginine=243.6 mg
Citric acid monohydrate=1.1 mg
Trisodium citrate dihydrate=27.9 mg
Formulation 3 (Per Vial)
Ceftaroline fosamil acetate=668.4 mg
NXL-104=649.8 mg
L-Arginine=243.6 mg
Citric acid monohydrate=2.2 mg
Trisodium citrate dihydrate=55.8 mg
Formulation 4 (Per Vial)
Ceftaroline fosamil acetate=668.4 mg
NXL-104=649.8 mg
L-Arginine=434.3 mg
Tartaric acid=37.5 mg
Sodium hydroxide=4 mg

TABLE 8

Assay and degradation profile of lyophilized Formulations 1-4

| Formulation | pH | NXL-104 % | Ceftaroline fosamil %* | NXL-104 related impurities (%) | | Ceftaroline related impurities (%) | |
|---|---|---|---|---|---|---|---|
| | | | | Decarbonyl | Total impurities | U1 | U3 |
| 1 | 5.79 | 101.80 | 92.36 | 0.19 | 0.44 | 1.11 | 2.89 |
| 2 | 4.73 | 99.96 | 91.83 | 0.32 | 0.76 | 0.76 | 4.60 |
| 3 | 4.77 | 101.19 | 93.93 | 0.28 | 0.85 | 0.73 | 4.00 |
| 4 | 5.28 | 101.84 | 94.14 | 0.12 | 0.19 | 0.74 | 3.03 |

*Assay values adjusted based on 95.5% assay of "as is" ceftaroline fosamil acetate. Actual assay values were 88.20, 87.70, 89.70 and 89.90 for Formulations 1, 2, 3 and 4 respectively.

Tables 9-12 show the assay and degradation profile of lyophilized Formulation 1 stored at 40° C./75% RH for 2 weeks.

TABLE 9

NXL-104 and ceftaroline fosamil assay

| | Ceftaroline fosamil | | | NXL-104 | |
|---|---|---|---|---|---|
| pH | Assay (%)* | U3 | Total impurities (w/o U3) (%) | Assay (%) | Total impurities (%) |
| 5.82 | 84.0 | 3.5 | 7.22 | 102.4 | 0.63 |

*Corrected value based on ceftaroline fosamil acetate potency of 95.5%.

TABLE 10

Ceftaroline related substances (%)

| U1 | U2 | U4 | U5 | U6 | U7 | U8 | U9 | MPTT | Adduct |
|---|---|---|---|---|---|---|---|---|---|
| 2.47 | 0.11 | 0.05 | ND | 0.13 | ND | ND | 0.10 | 0.37 | 2.63 |

ND = Not detectable

TABLE 11

Ceftaroline related substances (%)

| UNK* # 0.81 | UNK # 0.86 | UNK # 1.04 | UNK # 1.09 | UNK # 1.17 | UNK # 1.27 | UNK # 1.36 | UNK # 1.41 |
|---|---|---|---|---|---|---|---|
| 0.14 | ND | 0.59 | 0.14 | 0.12 | ND | ND | ND |

UNK = unknown impurities

TABLE 12

NXL-104 related substances (%)

| Decarbonyl | UNK # 0.30 | UNK # 0.33 | UNK # 0.36 | UNK # 0.37 |
|---|---|---|---|---|
| 0.21 | 0.14 | 0.12 | 0.16 | ND |

Tables 13-16 show the assay and degradation profile of lyophilized Formulation 2 stored at 40° C./75% RH for 2 weeks.

TABLE 13

NXL-104 and ceftaroline fosamil assay

| | Ceftaroline fosamil | | | NXL-104 | |
|---|---|---|---|---|---|
| pH | Assay (%)* | U3 | Total impurities (w/o U3) (%) | Assay (%) | Total impurities (%) |
| 4.70 | 86.1 | 6.1 | 4.07 | 102.1 | 0.48 |

*Corrected value based on ceftaroline fosamil acetate potency of 95.5%.

TABLE 14

Ceftaroline related substances (%)

| U1 | U2 | U4 | U5 | U6 | U7 | U8 | U9 | MPTT | Adduct |
|---|---|---|---|---|---|---|---|---|---|
| 1.76 | 0.46 | 0.09 | ND | 0.11 | ND | ND | 0.11 | 0.32 | 0.77 |

TABLE 15

Ceftaroline related substances (%)

| UNK # 0.81 | UNK # 0.86 | UNK # 1.04 | UNK # 1.09 | UNK # 1.17 | UNK # 1.27 | UNK # 1.36 | UNK # 1.41 |
|---|---|---|---|---|---|---|---|
| ND | ND | 0.13 | ND | 0.06 | ND | ND | ND |

TABLE 16

NXL-104 related substances (%)

| Decarbonyl | UNK # 0.30 | UNK # 0.33 | UNK # 0.36 | UNK # 0.37 |
|---|---|---|---|---|
| 0.21 | 0.21 | 0.27 | 0.09 | 0.12 |

Tables 17-20 show the assay and degradation profile of lyophilized Formulation 3 stored at 40° C./75% RH for 2 weeks.

TABLE 17

NXL-104 and ceftaroline fosamil assay

| | Ceftaroline fosamil | | | NXL-104 | |
|---|---|---|---|---|---|
| pH | Assay (%)* | U3 | Total impurities (w/o U3) (%) | Assay (%) | Total impurities (%) |
| 4.82 | 87.4 | 5.6 | 3.85 | 103.4 | 0.44 |

*Corrected value based on ceftaroline fosamil acetate potency of 95.5%.

TABLE 18

Ceftaroline related substances (%)

| U1 | U2 | U4 | U5 | U6 | U7 | U8 | U9 | MPTT | Adduct |
|---|---|---|---|---|---|---|---|---|---|
| 1.53 | 0.45 | 0.08 | ND | 0.10 | ND | ND | 0.11 | 0.31 | 0.84 |

TABLE 19

Ceftaroline related substances (%)

| UNK # 0.81 | UNK # 0.86 | UNK # 1.04 | UNK # 1.09 | UNK # 1.17 | UNK # 1.27 | UNK # 1.36 | UNK # 1.41 |
|---|---|---|---|---|---|---|---|
| ND | ND | 0.14 | ND | 0.06 | ND | ND | ND |

TABLE 20

NXL-104 related substances (%)

| Decarbonyl | UNK # 0.30 | UNK # 0.33 | UNK # 0.36 | UNK # 0.37 |
|---|---|---|---|---|
| 0.20 | 0.22 | 0.10 | 0.12 | ND |

Table 21-24 show the assay and degradation profile of lyophilized Formulation 4 stored at 40° C./75% RH for 2 weeks.

TABLE 21

NXL-104 and ceftaroline fosamil assay

| | Ceftaroline fosamil | | | NXL-104 | |
|---|---|---|---|---|---|
| pH | Assay (%)* | U3 | Total impurities (w/o U3) (%) | Assay (%) | Total impurities (%) |
| 5.26 | 87.1 | 3.8 | 5.44 | 103.6 | 0.59 |

*Corrected value based on ceftaroline fosamil acetate potency of 95.5%.

TABLE 22

Ceftaroline related substances (%)

| U1 | U2 | U4 | U5 | U6 | U7 | U8 | U9 | MPTT | Adduct |
|---|---|---|---|---|---|---|---|---|---|
| 1.83 | 0.13 | 0.06 | ND | 0.13 | ND | ND | 0.10 | 0.33 | 1.97 |

TABLE 23

Ceftaroline related substances (%)

| UNK # 0.81 | UNK # 0.86 | UNK # 1.04 | UNK # 1.09 | UNK # 1.17 | UNK # 1.27 | UNK # 1.36 | UNK # 1.41 |
|---|---|---|---|---|---|---|---|
| 0.06 | ND | 0.36 | 0.09 | 0.09 | ND | ND | ND |

TABLE 24

NXL-104 related substances (%)

| Decarbonyl | UNK # 0.30 | UNK # 0.33 | UNK # 0.36 | UNK # 0.37 |
|---|---|---|---|---|
| 0.18 | 0.16 | 0.11 | 0.14 | ND |

Formulation 5 was Prepared with the Following Composition:

Ceftaroline fosamil=600 mg

NXL-104 (free acid)=600 mg

L-Arginine=434.3 mg

Citric acid monohydrate=1.08 mg

Trisodium citrate dihydrate=27.90 mg

Pluronic F127=18.00 mg (equivalent to approximately 5% w/w of final lyophile)

Tables 25-27 show the assay and degradation profile of lyophilized Formulation 5 stored at 40° C./75% RH for 0 and 2 weeks.

TABLE 25

NXL-104 and ceftaroline fosamil assay

| | | Ceftaroline fosamil | | NXL-104 | |
|---|---|---|---|---|---|
| pH | Assay (%)* | U3 | Total impurities (w/o U3) (%) | Assay (%) | Total impurities (%) |
| t-zero | 6.01 | 92.8 | 3.0 | 1.62 | 103.9 | 0.33 |
| 2 weeks | 5.76 | 83.5 | 3.6 | 8.75 | 104.2 | 1.45 |

*Corrected value based on ceftaroline fosamil acetate potency of 95.5%.

TABLE 26

Ceftaroline related substances (%)

| | U1 | U2 | U4 | U5 | U6 | U7 | U8 | U9 | MPTT | Adduct |
|---|---|---|---|---|---|---|---|---|---|---|
| t-zero | 0.45 | 0.05 | 0.08 | ND | 0.05 | 0.05 | ND | 0.12 | <0.05 | 0.61 |
| 2 weeks | 3.90 | 0.12 | 0.18 | <0.05 | 0.24 | 0.04 | ND | 0.11 | 0.38 | 3.05 |

TABLE 27

NXL-104 related substances (%)

| | Decarbonyl | UNK # | UNK # | UNK # | UNK # | UNK # |
|---|---|---|---|---|---|---|
| | | 0.36 | 0.47 | 0.55 | 0.95 | 0.97 |
| t-zero | 0.11 | 0.22 | ND | ND | ND | ND |
| 2 weeks | 0.10 | 0.21 | 0.49 | 0.17 | 0.36 | 0.12 |

Formulation 6 was Prepared with the Following Composition:

Ceftaroline fosamil=600 mg

NXL-104 (free acid)=600 mg

L-Arginine=434.3 mg

Hydroxy propyl β cyclodextrin (HPβCD)=1300 mg

Table 28-30 show the assay and degradation profile of lyophilized Formulation 6 stored at 40° C./75% RH for 0 and 2 weeks.

TABLE 28

NXL-104 and ceftaroline fosamil assay

| | | Ceftaroline fosamil | | NXL-104 | |
|---|---|---|---|---|---|
| pH | Assay (%)* | U3 | Total impurities (w/o U3) (%) | Assay (%) | Total impurities (%) |
| t-zero | 6.00 | 91.5 | 2.9 | 1.82 | 103.3 | 0.66 |
| 2 weeks | 5.73 | 79.1 | 3.8 | 10.36 | 104.3 | 1.20 |

*Corrected value based on ceftaroline fosamil acetate potency of 95.5%.

TABLE 29

| | Ceftaroline related substances (%) | | | | | | | | | |
|---|---|---|---|---|---|---|---|---|---|---|
| | U1 | U2 | U4 | U5 | U6 | U7 | U8 | U9 | MPTT | Adduct |
| t-zero | 0.41 | <0.05 | 0.06 | ND | 0.05 | 0.06 | ND | 0.11 | 0.21 | 0.92 |
| 2 weeks | 3.19 | 0.08 | 0.34 | 0.07 | 0.22 | 0.07 | ND | 0.09 | 0.41 | 4.71 |

TABLE 30

| | NXL-104 related substances (%) | | | | | |
|---|---|---|---|---|---|---|
| | Decarbonyl | UNK # 0.36 | UNK # 0.47 | UNK # 0.84 | UNK # 0.95 | UNK # 0.97 |
| t-zero | 0.05 | 0.21 | ND | 0.40 | ND | ND |
| 2 weeks | <0.05 | 0.18 | 0.32 | ND | 0.60 | 0.10 |

Formulation 7 was Prepared with the Following Composition:
Ceftaroline fosamil=600 mg
NXL-104 (free acid)=600 mg
Citric acid monohydrate=10.8 mg
Trisodium citrate dihydrate=279.0 mg Table 31 shows the assay for lyophilized Formulation 7 stored at 40° C./75% RH for 0 and 2 weeks.

TABLE 31

| | NXL-104 and ceftaroline fosamil assay | | | | |
|---|---|---|---|---|---|
| | | Ceftaroline fosamil | | NXL-104 | |
| | pH | Assay (%)* | U3 | Assay (%) | Total impurities (%) |
| t-zero | 4.58 | 96.6 | 3.9 | 105.4 | 2.51 |
| 2 weeks | 4.58 | 87.3 | 7.6 | 104.4 | 2.85 |

*Corrected value based on ceftaroline fosamil acetate potency of 95.5%.

TABLE 32

| | NXL-104 and ceftaroline fosamil assay | | | | |
|---|---|---|---|---|---|
| | | Ceftaroline fosamil | | NXL-104 | |
| | pH | Assay (%)* | U3 | Assay (%) | Total impurities (%) |
| t-zero | 5.40 | 94.7 | 3.2 | 106.1 | 2.29 |
| 2 weeks | 5.38 | 87.7 | 5.0 | 105.0 | 2.34 |

*Corrected value based on ceftaroline fosamil acetate potency of 95.5%.

Formulation 9 was Prepared with the Following Composition:
Ceftaroline fosamil acetate=668.4 mg
NXL-104=649.8 mg
Citric acid monohydrate=87.8 mg
Trisodium citrate dihydrate=171.3 mg
(Citrate concentration=0.2M corresponding to pH 4.8)

Tables 33-35 show the assay and degradation profile of lyophilized CXL Formulation 9 stored at 40° C./75% RH for 0 and 1 month.

TABLE 33

| | NXL-104 and ceftaroline fosamil assay | | | | | |
|---|---|---|---|---|---|---|
| | | Ceftaroline fosamil | | | NXL-104 | |
| | pH | Assay (%)* | U3 | Total impurities (w/o U3) (%) | Assay (%) | Total impurities (%) |
| t-zero | 3.54 | 95.5 | 3.8 | 0.92 | 103.6 | 1.18 |
| 1 month | 3.62 | 82.4 | 10.39 | 3.96 | 101.9 | 2.06 |

*Corrected value based on ceftaroline fosamil acetate potency of 95.5%.

TABLE 34

| | Ceftaroline related substances (%) | | | | | | | | | |
|---|---|---|---|---|---|---|---|---|---|---|
| | U1 | U2 | U4 | U5 | U6 | U7 | U8 | U9 | MPTT | Adduct |
| t-zero | 0.37 | 0.09 | <0.05 | <0.05 | 0.12 | ND | ND | 0.06 | 0.28 | ND |
| 1 month | 1.20 | 1.42 | 0.05 | 0.10 | 0.25 | ND | ND | 0.08 | 0.45 | ND |

Formulation 8 was Prepared with the Following Composition:
Ceftaroline fosamil=450 mg
NXL-104 (free acid)=450 mg
L-Arginine=182.7 mg
Citric acid monohydrate=8.1 mg
Trisodium citrate dihydrate=209.3 mg Table 32 shows the assay for lyophilized CXL Formulation 8 stored at 40° C./75% RH for 0 and 2 weeks.

TABLE 35

| | NXL-104 related substances (%) |
|---|---|
| | Decarbonyl |
| t-zero | 0.94 |
| 1 month | 1.77 |

Formulation 10 was Prepared with the Following Composition:
Ceftaroline fosamil acetate=668.4 mg NXL-104=649.8 mg
Tartaric acid=150.0 mg (equivalent to 60 ml of 0.2M tartrate solution)
Sodium hydroxide=16.0 mg
L-Arginine=171.7 mg Tables 36-38 show the assay and degradation profile of lyophilized Formulation 10 stored at 40° C./75% RH for 0 and 1 month.

TABLE 36

NXL-104 and ceftaroline fosamil assay

| | | Ceftaroline fosamil | | | NXL-104 | |
|---|---|---|---|---|---|---|
| | pH | Assay (%)* | U3 | Total impurities (w/o U3) (%) | Assay (%) | Total impurities (%) |
| t-zero | 3.42 | 94.9 | 3.7 | 1.10 | 104.2 | 1.05 |
| 1 month | 3.49 | 85.2 | 8.80 | 3.67 | 102.6 | 2.28 |

*Corrected value based on ceftaroline fosamil acetate potency of 95.5%.

TABLE 37

Ceftaroline related substances (%)

| | U1 | U2 | U4 | U5 | U6 | U7 | U8 | U9 | MPTT | Adduct |
|---|---|---|---|---|---|---|---|---|---|---|
| t-zero | 0.43 | 0.06 | <0.05 | <0.05 | 0.12 | ND | ND | 0.06 | 0.30 | 0.13 |
| 1 month | 1.38 | 0.89 | <0.05 | 0.07 | 0.24 | 0.01 | ND | 0.07 | 0.46 | 0.19 |

TABLE 38

NXL-104 related substances (%)

| | Decarbonyl |
|---|---|
| t-zero | 0.81 |
| 1 month | 1.54 |

Example 8

Stability of Amorphous NXL-104 and Crystalline Ceftaroline Fosamil

A formulation containing amorphous NXL-104 and crystalline ceftaroline fosamil was prepared with the following composition per vial:

| | |
|---|---|
| Ceftaroline fosamil (monohydrate, acetic acid solvate) | 668.4 mg (equivalent to 600 mg of ceftaroline fosamil) |
| L-Arginine | 434.3 mg |
| NXL-104 | 649.8 mg (equivalent to 600 mg of NXL-104 free acid) |

Amorphous NXL-104 was weighed into vials pre-filled with ceftaroline fosamil-Arginine blend. The vials were flushed with nitrogen, stoppered, sealed and stored at different conditions to monitor stability. Packaging components used were 20 ml Type I glass vial, Gray chlorobutyl-isoprene stopper and Blue Aluminum tear-off seal.

Tables 39-41 show the stability data for the formulation at t-zero.

TABLE 39

NXL-104 and ceftaroline fosamil assay

| | | Ceftaroline fosamil | | | NXL-104 | |
|---|---|---|---|---|---|---|
| | pH | Assay (%) | U3 | Total impurities (w/o U3) (%) | Assay (%) | Total impurities (%) |
| Initial | 5.49 | 100.45 | 2.74 | 0.92 | 101.21 | 0.72 |
| 3 hours | 5.44 | 99.93 | 2.97 | 0.10 | 101.35 | 0.74 |
| 6 hours | 5.46 | 99.74 | 3.19 | 0.98 | 101.30 | 0.75 |

TABLE 40

Decarbonyl and unknown impurities

| | Decarbonyl | UNK # 0.43 |
|---|---|---|
| Initial | 0.56 | 0.16 |
| 3 hours | 0.58 | 0.16 |
| 6 hours | 0.59 | 0.16 |

TABLE 41

Ceftaroline related impurities

| | U1 | U2 | U4 | U5 | U6 | U7 | U8 | U9 | MPTT | Adduct | UNK #1.55 |
|---|---|---|---|---|---|---|---|---|---|---|---|
| Initial | 0.47 | 0.04 | ND | ND | 0.10 | 0.06 | ND | 0.08 | 0.04 | 0.13 | 0.00 |
| 3 hours | 0.53 | 0.05 | ND | ND | 0.09 | 0.05 | ND | 0.08 | 0.04 | 0.12 | 0.04 |
| 6 hours | 0.51 | 0.05 | ND | ND | 0.09 | 0.05 | ND | 0.07 | 0.04 | 0.12 | 0.05 |

Tables 42-44 show the stability data for the formulation stored for 3 months at 40° C./75% RH.

TABLE 42

NXL-104 and ceftaroline fosamil assay

| | | Ceftaroline fosamil | | | NXL-104 | |
|---|---|---|---|---|---|---|
| | pH | Assay (%) | U3 | Total impurities (w/o U3) (%) | Assay (%) | Total impurities (%) |
| Initial | 5.71 | 96.13 | 3.66 | 1.58 | 93.30 | 1.04 |
| 3 hours | 5.62 | 95.38 | 3.87 | 1.55 | 92.98 | 1.16 |
| 6 hours | 5.67 | 95.03 | 4.11 | 1.75 | 93.12 | 1.09 |

TABLE 43

Decarbonyl and unknown impurities

| | Decarbonyl | UNK #0.35 | UNK #0.38 | UNK #0.39 | UNK #0.53 |
|---|---|---|---|---|---|
| Initial | 0.73 | 0.03 | 0.05 | 0.03 | 0.21 |
| 3 hours | 0.76 | 0.02 | 0.19 | 0.03 | 0.18 |
| 6 hours | 0.77 | 0.03 | 0.19 | 0.03 | 0.15 |

TABLE 44

Ceftaroline related impurities

| | U1 | U2 | U4 | U5 | U6 | U7 | U8 | U9 | MPTT | Adduct | UNK #1.56 |
|---|---|---|---|---|---|---|---|---|---|---|---|
| Initial | 0.50 | 0.13 | ND | ND | 0.30 | ND | ND | 0.08 | 0.22 | 0.27 | 0.08 |
| 3 hours | 0.56 | 0.14 | ND | ND | 0.27 | ND | ND | 0.08 | 0.23 | 0.27 | ND |
| 6 hours | 0.62 | 0.14 | ND | ND | 0.24 | 0.05 | ND | 0.08 | 0.24 | 0.26 | 0.12 |

Tables 45-48 show the stability data for the formulation stored for 6 months at 40° C./75% RH.

TABLE 45

NXL-104 and ceftaroline fosamil assay

| | | Ceftaroline fosamil | | | NXL-104 | |
|---|---|---|---|---|---|---|
| | pH | Assay (%) | U3 | Total impurities (w/o U3) (%) | Assay (%) | Total impurities (%) |
| Initial | 5.69 | 96.80 | 3.83 | 1.77 | 90.34 | 1.49 |
| 3 hours | 5.85 | 97.20 | 4.05 | 1.77 | 90.53 | 1.45 |
| 6 hours | 5.77 | 95.80 | 4.31 | 1.74 | 90.40 | 1.43 |

TABLE 46

NXL-104 related impurities

| | Decarbonyl | UNK #0.38 | UNK #0.55 |
|---|---|---|---|
| Initial | 0.99 | 0.24 | 0.26 |
| 3 hours | 0.98 | 0.24 | 0.23 |
| 6 hours | 0.98 | 0.25 | 0.20 |

TABLE 47

Ceftaroline related impurities

| | U1 | U2 | U4 | U5 | U6 | U7 | U8 | U9 | MPTT | Adduct |
|---|---|---|---|---|---|---|---|---|---|---|
| Initial | 0.38 | 0.10 | <0.05 | <0.05 | 0.34 | 0.06 | ND | 0.10 | 0.30 | 0.38 |
| 3 hours | 0.39 | 0.11 | <0.05 | <0.05 | 0.31 | 0.05 | ND | 0.09 | 0.30 | 0.37 |
| 6 hours | 0.42 | 0.11 | <0.05 | <0.05 | 0.29 | 0.05 | ND | 0.09 | 0.31 | 0.36 |

TABLE 48

Unknown impurities

| | UNK # 0.18 | UNK # 0.24 | UNK # 0.42 | UNK # 0.48 | UNK # 1.55 | UNK # 1.72 | UNK # 1.82 |
|---|---|---|---|---|---|---|---|
| Initial | <0.05 | <0.05 | <0.05 | 0.05 | 0.06 | <0.05 | <0.05 |
| 3 hours | 0.05 | <0.05 | <0.05 | 0.05 | 0.05 | <0.05 | <0.05 |
| 6 hours | 0.05 | <0.05 | <0.05 | 0.06 | <0.05 | <0.05 | <0.05 |

Table 49-52 show the stability data for the formulation containing amorphous NXL-104 and crystalline ceftaroline fosamil stored for 9 months at 40° C./75% RH.

TABLE 49

NXL-104 and ceftaroline fosamil assay

| | | Ceftaroline fosamil | | | NXL-104 | |
|---|---|---|---|---|---|---|
| | pH | Assay (%) | U3 | Total impurities (w/o U3) (%) | Assay (%) | Total impurities (%) |
| Initial | 5.59 | 96.4 | 4.22 | 1.49 | 90.3 | 1.68 |
| 3 hours | 5.61 | 97.0 | 4.28 | 1.47 | 90.0 | 1.66 |
| 6 hours | 5.66 | 94.9 | 4.56 | 1.45 | 89.1 | 1.61 |

TABLE 50

Decarbonyl and unknown impurities

| | Decarbonyl | UNK # 0.38 | UNK # 0.40 | UNK # 0.60 |
|---|---|---|---|---|
| Initial | 1.09 | 0.11 | 0.27 | 0.21 |
| 3 hours | 1.08 | 0.11 | 0.27 | 0.20 |
| 6 hours | 1.07 | 0.11 | 0.27 | 0.16 |

TABLE 51

Ceftaroline related impurities

| | U1 | U2 | U4 | U5 | U6 | U7 | U8 | U9 | MPTT | Adduct |
|---|---|---|---|---|---|---|---|---|---|---|
| Initial | 0.33 | 0.11 | <0.05 | <0.05 | 0.22 | 0.04 | ND | 0.11 | 0.35 | 0.09 |
| 3 hours | 0.32 | 0.11 | ND | ND | 0.21 | 0.04 | ND | 0.11 | 0.35 | 0.09 |
| 6 hours | 0.33 | 0.11 | <0.05 | <0.05 | 0.18 | 0.04 | ND | 0.10 | 0.36 | 0.09 |

TABLE 52

Unknown impurities

| | UNK # 0.12 | UNK # 0.19 | UNK # 0.47 | UNK # 1.52 |
|---|---|---|---|---|
| Initial | 0.12 | ND | 0.06 | 0.06 |
| 3 hours | 0.12 | ND | 0.06 | 0.06 |
| 6 hours | 0.13 | 0.05 | 0.06 | <0.05 |

Table 53-56 show the stability data for the formulation containing amorphous NXL-104 and crystalline ceftaroline fosamil stored for 9 months at 25° C./60% RH

TABLE 53

NXL-104 and ceftaroline fosamil assay

| | | Ceftaroline fosamil | | | NXL-104 | |
|---|---|---|---|---|---|---|
| | pH | Assay (%) | U3 | Total impurities (w/o U3) (%) | Assay (%) | Total impurities (%) |
| Initial | 5.65 | 97.9 | 3.40 | 1.19 | 93.1 | 1.44 |
| 3 hours | 5.57 | 97.1 | 3.47 | 1.11 | 92.5 | 1.40 |
| 6 hours | 5.64 | 96.4 | 3.74 | 1.09 | 92.7 | 1.39 |

TABLE 54

Decarbonyl and unknown impurities

| | Decarbonyl | UNK # 0.38 | UNK # 0.40 | UNK # 0.60 |
|---|---|---|---|---|
| Initial | 1.08 | <0.05 | 0.25 | 0.11 |
| 3 hours | 1.05 | <0.05 | 0.25 | 0.10 |
| 6 hours | 1.05 | <0.05 | 0.25 | 0.09 |

TABLE 55

| | Ceftaroline related impurities | | | | | | | | | |
|---|---|---|---|---|---|---|---|---|---|---|
| | U1 | U2 | U4 | U5 | U6 | U7 | U8 | U9 | MPTT | Adduct |
| Initial | 0.50 | 0.13 | <0.05 | <0.05 | 0.17 | 0.05 | ND | 0.14 | 0.11 | 0.09 |
| 3 hours | 0.43 | 0.13 | <0.05 | <0.05 | 0.16 | 0.04 | ND | 0.14 | 0.12 | 0.09 |
| 6 hours | 0.44 | 0.14 | <0.05 | <0.05 | 0.14 | 0.04 | ND | 0.13 | 0.12 | 0.08 |

TABLE 56

| | Unknown impurities | | | |
|---|---|---|---|---|
| | UNK # 0.12 | UNK # 0.19 | UNK # 0.47 | UNK # 1.52 |
| Initial | <0.05 | <0.05 | <0.05 | <0.05 |
| 3 hours | <0.05 | <0.05 | <0.05 | <0.05 |
| 6 hours | <0.05 | <0.05 | <0.05 | <0.05 |

Table 57-60 show the stability data for the formulation containing amorphous NXL-104 and crystalline ceftaroline fosamil stored for 9 months at 2-8° C.

TABLE 57

| | NXL-104 and ceftaroline fosamil assay | | | | | |
|---|---|---|---|---|---|---|
| | | Ceftaroline fosamil | | | NXL-104 | |
| | pH | Assay (%) | U3 | Total impurities (w/o U3) (%) | Assay (%) | Total impurities (%) |
| Initial | 5.43 | 100.5 | 3.02 | 0.89 | 96.8 | 1.11 |
| 3 hours | 5.50 | 100.6 | 3.07 | 0.87 | 97.0 | 1.11 |
| 6 hours | 5.65 | 100.1 | 3.35 | 0.91 | 96.9 | 1.08 |

TABLE 58

| | Decarbonyl and unknown impurities | | | |
|---|---|---|---|---|
| | Decarbonyl | UNK # 0.38 | UNK # 0.40 | UNK # 0.60 |
| Initial | 0.87 | <0.05 | 0.24 | ND |
| 3 hours | 0.84 | <0.05 | 0.27 | ND |
| 6 hours | 0.84 | <0.05 | 0.24 | ND |

TABLE 59

| | Ceftaroline related impurities | | | | | | | | | |
|---|---|---|---|---|---|---|---|---|---|---|
| | U1 | U2 | U4 | U5 | U6 | U7 | U8 | U9 | MPTT | Adduct |
| Initial | 0.45 | 0.11 | <0.05 | <0.05 | 0.09 | 0.05 | ND | 0.11 | <0.05 | 0.08 |
| 3 hours | 0.43 | 0.11 | <0.05 | <0.05 | 0.09 | 0.05 | ND | 0.11 | <0.05 | 0.08 |
| 6 hours | 0.42 | 0.12 | <0.05 | <0.05 | 0.08 | 0.05 | ND | 0.11 | 0.05 | 0.08 |

TABLE 60

| | Unknown impurities | | | |
|---|---|---|---|---|
| | UNK # 0.12 | UNK # 0.19 | UNK # 0.47 | UNK # 1.52 |
| Initial | <0.05 | <0.05 | <0.05 | <0.05 |
| 3 hours | <0.05 | ND | ND | ND |
| 6 hours | <0.05 | <0.05 | <0.05 | ND |

Example 9

Stability of crystalline Form I of trans-7-oxo-6-(sulphooxy)-1,6-diazabicyclo[3,2,1]octane-2-carboxamide sodium salt and crystalline ceftaroline fosamil A formulation containing Form I NXL-104 and crystalline ceftaroline fosamil was prepared with the following composition per vial:

| | |
|---|---|
| Ceftaroline fosamil (monohydrate, acetic acid solvate) | 668.4 mg (equivalent to 600 mg of ceftaroline fosamil) |
| L-Arginine | 434.3 mg |
| NXL-104 | 649.8 mg (equivalent to 600 mg of NXL-104 free acid) |

Ceftaroline fosamil, trans-7-oxo-6-(sulphooxy)-1,6-diazabicyclo[3,2,1]octane-2-carboxamide sodium salt (Form I) and L-Arginine were blended in a twin shell blender (Patterson-Kelly) for times ranging from 15 to 60 minutes. The blend was subsequently weighed into vials and the vials were stoppered (with or without nitrogen), sealed and stored at different conditions to monitor stability. Packaging components used were 20 ml Type I glass vial, Gray chlorobutyl-isoprene stopper and Blue Aluminum tear-off seal.

Ceftaroline fosamil median particle diameter=10 μm
trans-7-oxo-6-(sulphooxy)-1,6-diazabicyclo[3,2,1]octane-2-carboxamide sodium salt (Form I) median particle diameter=145 μm
L-Arginine median particle diameter=Variable Surprisingly and unexpectedly, the formulation comprising crystalline NXL-104 and ceftaroline fosamil was found to be more stable than formulations comprising amorphous NXL-104 and ceftaroline fosamil.

Table 61-62 provide the stability data for the formulation comprising Form I containing nitrogen in vial headspace. The median diameter of L-Arginine was 290 μm.

TABLE 61

NXL-104 and ceftaroline fosamil assay

|  | pH | NXL-104 Assay (%) | Decarbonyl (%) | NXL-104 Total Impurities (%) | Ceftaroline Assay (%)* | U3 (%) | Ceftaroline Total Impurities (w/o U3) (%) | Water Content (%) |
|---|---|---|---|---|---|---|---|---|
| t-zero | 5.72 | 104.8 | 0.21 | 0.45 | 97.4 | 2.5 | 0.74 | — |
| 2 weeks 2-8° C. | 5.67 | 108.4 | ND | 0.33 | 100.7 | 2.6 | 0.70 | — |
| 2 weeks 25° C./60% RH | 5.56 | 108.5 | ND | 0.38 | 99.9 | 2.8 | 0.90 | — |
| 2 weeks 40° C./75% RH | 5.59 | 108.7 | ND | 0.45 | 97.5 | 3.4 | 1.01 | — |
| 1 month 2-8° C. | 5.79 | 106.4 | <0.05 | <0.05 | 97.4 | 2.6 | 0.64 | — |
| 1 month 25° C./60% RH | 5.63 | 104.3 | <0.05 | 0.21 | 94.7 | 3.1 | 0.74 | — |
| 1 month 40° C./75% RH | 5.71 | 104.6 | <0.05 | 0.22 | 93.2 | 3.7 | 1.10 | — |
| 3 months 25° C./60% RH | 5.76 | 104.7 | 0.02 | 0.02 | 95.9 | 3.31 | 1.14 | 1.11 |
| 3 months 40° C./75% RH | 5.87 | 104.6 | 0.02 | 0.02 | 94.6 | 3.97 | 1.52 | 1.10 |

TABLE 62

Ceftaroline related substances (%)

|  | U1 | U2 | U6 | U7 | U9 | MPTT | Adduct |
|---|---|---|---|---|---|---|---|
| t-zero | 0.32 | ND | 0.04 | ND | 0.10 | 0.23 | ND |
| 2 weeks 2-8° C. | 0.32 | ND | 0.06 | 0.01 | 0.05 | 0.19 | 0.07 |
| 2 weeks 25° C./60% RH | 0.41 | 0.05 | 0.10 | 0.01 | 0.05 | 0.21 | 0.08 |
| 2 weeks 40° C./75% RH | 0.31 | 0.06 | 0.13 | 0.01 | 0.05 | 0.32 | 0.13 |
| 1 month 2-8° C. | 0.24 | <0.05 | 0.09 | 0.01 | 0.05 | 0.20 | 0.05 |
| 1 month 25° C./60% RH | 0.30 | <0.05 | 0.17 | ND | <0.05 | 0.27 | <0.05 |
| 1 month 40° C./75% RH | 0.22 | <0.05 | 0.20 | ND | 0.05 | 0.53 | <0.05 |
| 3 months 25° C./60% RH | 0.52 | <0.05 | 0.19 | <0.05 | <0.05 | 0.37 | 0.06 |
| 3 months 40° C./75% RH | 0.38 | <0.05 | 0.18 | <0.05 | <0.05 | 0.70 | 0.05 |

Table 63-64 provide the stability data for the formulation comprising Form I without nitrogen in vial headspace. The median diameter of L-Arginine was 290 μm.

TABLE 63

NXL-104 and ceftaroline fosamil assay

|  | pH | NXL-104 Assay (%) | Decarbonyl (%) | NXL-104 Total Impurities (%) | Ceftaroline fosamil Assay (%)* | U3 (%) | Ceftaroline Total Impurities (w/o U3) (%) | Water Content (%) |
|---|---|---|---|---|---|---|---|---|
| t-zero | 5.76 | 104.8 | 0.21 | 0.45 | 98.0 | 2.50 | 0.71 | — |
| 3 months 40° C./75% RH | 5.81 | 104.7 | 0.03 | 0.03 | 94.4 | 4.04 | 1.67 | 0.98 |
| 3 months 25° C./60% RH | 5.72 | 105.2 | 0.02 | 0.02 | 97.6 | 3.36 | 1.18 | 1.37 |

TABLE 64

| | Ceftaroline related substances (%) | | | | | | |
|---|---|---|---|---|---|---|---|
| | U1 | U2 | U6 | U7 | U9 | MPTT | Adduct |
| t-zero | 0.29 | ND | 0.04 | ND | 0.01 | 0.23 | ND |
| 3 months 40° C./75% RH | 0.41 | <0.05 | 0.18 | <0.05 | <0.05 | 0.71 | 0.10 |
| 3 months 25° C./60% RH | 0.53 | <0.05 | 0.19 | <0.05 | 0.05 | 0.36 | 0.10 |

Table 65-66 provide the stability data for the formulation comprising Form I containing nitrogen in vial headspace. The median diameter of L-Arginine was 20 μm.

TABLE 65

| | NXL-104 and ceftaroline fosamil assay | | | | | | | |
|---|---|---|---|---|---|---|---|---|
| | pH | NXL-104 Assay (%) | Decarbonyl (%) | NXL-104 Total Impurities (%) | Ceftaroline Assay (%)* | U3 (%) | Ceftaroline Total Impurities (w/o U3) (%) | Water Content (%) |
| t-zero | 5.76 | 104.9 | 0.22 | 0.41 | 97.0 | 2.7 | 0.78 | — |
| 1 month 2-8° C. | 5.72 | 102.8 | <0.05 | 0.26 | 97.3 | 3.0 | 0.43 | — |
| 1 month 25° C./60% RH | 6.53 | 101.1 | <0.05 | 0.25 | 93.0 | 3.3 | 0.43 | — |
| 1 month 40° C./75% RH | 5.56 | 105.1 | <0.05 | 1.19 | 94.5 | 4.1 | 0.82 | — |
| 3 months 25° C./60% RH | 5.81 | 107.3 | ND | ND | 94.5 | 3.55 | 1.39 | 1.54 |
| 3 months 40° C./75% RH | 6.79 | 109.3 | 0.06 | 0.06 | 84.5 | 4.15 | 2.48 | 1.41 |

TABLE 66

| | Ceftaroline related substances (%) | | | | | | |
|---|---|---|---|---|---|---|---|
| | U1 | U2 | U6 | U7 | U9 | MPTT | Adduct |
| t-zero | 0.27 | <0.05 | 0.10 | ND | 0.10 | 0.15 | 0.10 |
| 1 month 2-8° C. | 0.05 | 0.05 | 0.04 | 0.03 | 0.09 | <0.05 | 0.10 |
| 1 month 25° C./60% RH | 0.08 | 0.06 | 0.10 | 0.02 | 0.07 | <0.05 | 0.05 |
| 1 month 40° C./75% RH | 0.07 | 0.07 | 0.25 | 0.01 | 0.07 | <0.05 | 0.05 |
| 3 months 25° C./60% RH | 0.64 | <0.05 | 0.24 | <0.05 | <0.05 | 0.28 | 0.15 |
| 3 months 40° C./75% RH | 0.51 | <0.05 | 0.39 | 0.05 | <0.05 | 0.85 | 0.23 |

Table 67-68 provide the stability data for the formulation comprising Form I containing nitrogen in vial headspace. The median diameter of L-Arginine was 290 μm.

TABLE 67

NXL-104 and ceftaroline fosamil assay

|  | pH | NXL-104 Assay (%) | Decarbonyl (%) | NXL-104 Total Impurities (%) | Ceftaroline Assay (%)* | U3 (%) | Ceftaroline Total Impurities (w/o U3) (%) | Water Content (%) |
|---|---|---|---|---|---|---|---|---|
| t-zero | 6.33 | 102.9 | <0.05 | <0.05 | 97.0 | 2.50 | 0.85 | — |
| 3 months 25° C./60% RH | 6.46 | 96.3 | <0.05 | <0.05 | 95.9 | 3.24 | 0.97 | 1.45 |
| 3 months 40° C./75% RH | 5.40 | 105.1 | <0.05 | <0.05 | 93.8 | 4.02 | 1.53 | 1.38 |

TABLE 68

Ceftaroline related substances (%)

|  | U1 | U2 | U6 | U7 | U9 | MPTT | Adduct |
|---|---|---|---|---|---|---|---|
| t-zero | 0.28 | <0.05 | 0.08 | 0.03 | 0.05 | 0.24 | 0.17 |
| 3 months 25° C./60% RH | 0.29 | <0.05 | 0.17 | ND | 0.05 | 0.35 | 0.06 |
| 3 months 40° C./75% RH | 0.20 | <0.05 | 0.23 | ND | <0.05 | 0.84 | 0.07 |

Table 69-70 provide the stability data for the formulation comprising Form I containing nitrogen in vial headspace. The median diameter of L-Arginine was 181 μm.

TABLE 69

NXL-104 and ceftaroline fosamil assay

|  | pH | NXL-104 Assay (%) | Decarbonyl (%) | NXL-104 Total Impurities (%) | Ceftaroline Assay (%)* | U3 (%) | Ceftaroline Total Impurities (w/o U3) (%) | Water Content (%) |
|---|---|---|---|---|---|---|---|---|
| t-zero | 5.65 | 105.4 | <0.05 | 0.25 | 98.8 | 2.44 | 0.71 | 1.62 |
| 1 month 25° C./60% RH | 5.85 | 105.7 | <0.05 | <0.05 | 93.8 | 3.56 | 1.47 | — |
| 1 month 40° C./75% RH | 5.65 | 107.9 | <0.05 | <0.05 | 97.0 | 3.02 | 1.18 | — |

TABLE 70

Ceftaroline related substances (%)

|  | U1 | U2 | U6 | U7 | U9 | MPTT | Adduct |
|---|---|---|---|---|---|---|---|
| t-zero | 0.27 | <0.05 | 0.09 | ND | 0.06 | 0.29 | <0.05 |
| 1 month 25° C./60% RH | 0.42 | <0.05 | 0.18 | 0.02 | 0.05 | 0.64 | 0.10 |
| 1 month 40° C./75% RH | 0.47 | <0.05 | 0.13 | 0.02 | 0.05 | 0.42 | 0.08 |

Thus, the present example demonstrates that surprisingly and unexpectedly, formulations comprising Form I and ceftaroline fosamil are more stable than formulations comprising amorphous NXL-104 and ceftaroline fosamil.

Tables 71-72 provide the stability data for formulation comprising Form I that was irradiated by γ-radiation (45 KGy) containing nitrogen in vial.

TABLE 71

NXL-104 and ceftaroline fosamil assay

|  | pH | NXL-104 Assay (%) | Decarbonyl (%) | NXL-104 Total Impurities (%) | Ceftaroline Assay (%)* | U3 (%) | Ceftaroline Total Impurities (%) w/o U3 |
|---|---|---|---|---|---|---|---|
| t-zero | 5.88 | 108.2 | <0.05 | <0.05 | 99.3 | 2.44 | 0.84 |
| After irradiation | 5.55 | 101.1 | <0.05 | 0.35 | 95.6 | 2.61 | 1.17 |

*Adjusted by ceftaroline fosamil acetate potency

TABLE 72

| | Ceftaroline related substances (%) | | | | | | | |
|---|---|---|---|---|---|---|---|---|
| | U1 | U2 | U4 | U6 | U7 | U9 | MPTT | Adduct |
| t-zero | 0.26 | ND | <0.05 | 0.08 | ND | 0.05 | 0.33 | 0.12 |
| After irradiation | 0.28 | 0.05 | <0.05 | 0.20 | 0.05 | 0.06 | 0.37 | 0.14 |

Tables 73-74 provide the stability data for formulation comprising Form I that was irradiated by γ-radiation (45 KGy) without nitrogen in vial.

TABLE 73

| | NXL-104 and ceftaroline fosamil assay | | | | | | |
|---|---|---|---|---|---|---|---|
| | pH | NXL-104 Assay (%) | Decarbonyl (%) | NXL-104 Total Impurities (%) | Ceftaroline Assay (%)* | U3 (%) | Ceftaroline Total Impurities (%) w/o U3 |
| t-zero | 5.97 | 106.5 | <0.05 | <0.05 | 97.6 | 2.41 | 0.77 |
| After irradiation | 5.47 | 100.6 | <0.05 | 0.35 | 94.8 | 2.60 | 1.35 |

*Adjusted by ceftaroline fosamil acetate potency

TABLE 74

| | Ceftaroline related substances (%) | | | | | | | |
|---|---|---|---|---|---|---|---|---|
| | U1 | U2 | U4 | U6 | U7 | U9 | MPTT | Adduct |
| t-zero | 0.25 | ND | <0.05 | 0.08 | ND | 0.05 | 0.33 | 0.06 |
| After irradiation | 0.24 | 0.05 | <0.05 | 0.19 | 0.05 | 0.06 | 0.50 | 0.12 |

Tables 75-76 provide the stability data for formulation comprising Form I that was irradiated by e-beam (45 KGy) containing nitrogen in vial.

TABLE 75

| | NXL-104 and ceftaroline fosamil assay | | | | | | |
|---|---|---|---|---|---|---|---|
| | pH | NXL-104 Assay (%) | Decarbonyl (%) | NXL-104 Total Impurities (%) | Ceftaroline Assay (%)* | U3 (%) | Ceftaroline Total Impurities (%) w/o U3 |
| t-zero | 5.88 | 108.2 | <0.05 | <0.05 | 99.3 | 2.44 | 0.84 |
| After irradiation | 6.40 | 96.6 | <0.05 | 0.32 | 94.3 | 2.45 | 1.12 |

*Adjusted by ceftaroline fosamil acetate potency

TABLE 76

| | Ceftaroline related substances (%) | | | | | | | |
|---|---|---|---|---|---|---|---|---|
| | U1 | U2 | U4 | U6 | U7 | U9 | MPTT | Adduct |
| t-zero | 0.26 | ND | <0.05 | 0.08 | ND | 0.05 | 0.33 | 0.12 |
| After irradiation | 0.23 | <0.05 | <0.05 | 0.20 | 0.06 | 0.06 | 0.42 | 0.13 |

Tables 77-78 provide the stability data for formulation comprising Form I that was irradiated by e-beam (45 KGy) without nitrogen in vial.

TABLE 77

| | | NXL-104 and ceftaroline fosamil assay | | | | |
|---|---|---|---|---|---|---|
| | pH | NXL-104 Assay (%) | Decarbonyl (%) | NXL-104 Total Impurities (%) | Ceftaroline Assay (%)* | U3 (%) | Ceftaroline Total Impurities (%) w/o U3 |
| t-zero | 5.97 | 106.5 | <0.05 | <0.05 | 97.6 | 2.41 | 0.77 |
| After irradiation | 5.80 | 97.9 | <0.05 | 0.31 | 94.9 | 2.50 | 1.17 |

*Adjusted by ceftaroline fosamil acetate potency

TABLE 78

| | Ceftaroline related substances (%) | | | | | | |
|---|---|---|---|---|---|---|---|
| | U1 | U2 | U4 | U6 | U7 | U9 | MPTT | Adduct |
| t-zero | 0.25 | ND | <0.05 | 0.08 | ND | 0.05 | 0.33 | 0.06 |
| After irradiation | 0.22 | <0.05 | <0.05 | 0.19 | 0.06 | 0.06 | 0.39 | 0.23 |

Example 10

Stability of Form II of trans-7-oxo-6-(sulphooxy)-1,6-diazabicyclo[3,2,1]octane-2-carboxamide sodium salt and crystalline ceftaroline fosamil Formulation comprising Form II of NXL-104 and ceftaroline fosamil was prepared with the following composition per vial:

Ceftaroline fosamil (monohydrate, acetic acid solvate) 668.4 mg (equivalent to 600 mg of ceftaroline fosamil)
L-Arginine 434.3 mg
NXL-104 690.4 mg (equivalent to 600 mg of NXL-104 free acid)

Ceftaroline fosamil monohydrate, acetic acid solvate, NXL-104 (Form II) and L-Arginine were blended in a twin shell blender (Patterson-Kelly) for times ranging from 15 to 60 minutes. The blend was subsequently weighed into vials and the vials were stoppered (with or without nitrogen), sealed and stored at different conditions to monitor stability. Packaging components used were 20 ml Type I glass vial, Gray bromobutyl Omni stopper and Blue Aluminum tear-off seal.

Tables 79-80 show the stability data for the formulation in a vial without nitrogen.
The median diameter of L-Arginine was 20 μm.

TABLE 79

| | | NXL-104 and ceftaroline fosamil assay | | | | | |
|---|---|---|---|---|---|---|---|
| | pH | NXL-104 Assay (%) | Decarbonyl (%) | NXL-104 Total Impurities (%) | Ceftaroline fosamil Assay (%)* | U3 (%) | Ceftaroline Total Impurities (%) w/o U3 |
| t-zero | 4.80 | 113.8 | 0.10 | 0.10 | 102.2 | 2.89 | 1.15 |
| 3 months 40° C./75% RH | 5.90 | 99.9 | 0.17 | 0.33 | 91.2 | 4.32 | 1.97 |

*Corrected by ceftaroline fosamil acetate potency

TABLE 80

| Ceftaroline related substances (%) | | | | | | | |
|---|---|---|---|---|---|---|---|
| U1 | U2 | U6 | U7 | U9 | MPTT | Adduct | Total unknown |
| t-zero | | | | | | | |
| 0.39 | <0.05 | 0.08 | <0.05 | 0.06 | 0.41 | 0.17 | <0.05 |
| 3 months 40° C./75% RH | | | | | | | |
| <0.05 | <0.05 | 0.17 | 0.05 | <0.05 | 1.14 | 0.05 | 0.30 |

Tables 81-82 show the stability data for the formulation comprising Form II and ceftaroline fosamil in a vial containing nitrogen. The median diameter of L-Arginine was 20 µm.

TABLE 81

NXL-104 and ceftaroline fosamil assay

|  | pH | NXL-104 Assay (%) | Decarbonyl (%) | NXL-104 Total Impurities (%) | Ceftaroline fosamil Assay (%)* | U3 (%) | Ceftaroline Total Impurities (%) w/o U3 |
|---|---|---|---|---|---|---|---|
| t-zero | 6.77 | 102.3 | 0.08 | 0.08 | 92.3 | 2.30 | 1.49 |
| 3 months 40° C./75% RH | 5.80 | 98.3 | 0.25 | 0.49 | 87.2 | 4.17 | 2.11 |

*Corrected by ceftaroline fosamil acetate potency

TABLE 82

| Ceftaroline related substances (%) | | | | | | | |
|---|---|---|---|---|---|---|---|
| U1 | U2 | U6 | U7 | U9 | MPTT | Adduct | Total unknown |
| t-zero | | | | | | | |
| 0.50 | <0.05 | 0.08 | 0.11 | 0.05 | 0.47 | 0.24 | <0.05 |
| 3 months 40° C./75% RH | | | | | | | |
| 0.09 | <0.05 | 0.17 | 0.06 | <0.05 | 1.25 | <0.05 | 0.33 |

Example 11

Pharmacokinetic Data

A single center, two-part randomized Phase I Study was conducted to evaluate the safety, tolerability, and pharmacokinetics of single and multiple intravenous doses of ceftaroline fosamil and NXL-104 in healthy male and female subjects, aged 18 through 45 years.

Study Drugs

Ceftaroline fosamil for injection was supplied as a sterile powder containing a dry mixture of ceftaroline fosamil and L-arginine in single-dose, clear vials containing 600 mg of ceftaroline fosamil (on a corrected basis, anhydrous acetate free).

NXL-104 for Injection (trans-7-oxo-6-(sulphooxy)-1,6-diazabicyclo[3,2,1]octane-2-carboxamide sodium salt) was supplied as a sterile powder in single-dose, clear vials containing 600 mg of NXL-104 (on a free-acid basis).

Inclusion Criteria

To be eligible to participate in the study, subjects were required to meet the following criteria:

1. Sign a written informed consent before any study procedures were performed
2. Be healthy males or females, 18 through 45 years of age, inclusive
3. If female, have a negative serum pregnancy test (β-human chorionic gonadotropin [HCG]) at screening and a negative serum or urine pregnancy test on Day −1
4. If female of child-bearing potential or female <2 years postmenopausal, agree to and comply with using highly effective double-barrier methods of birth control (eg, condom plus diaphragm) while participating in this study
5. Have normal, or abnormal but not clinically significant, results on the hematology evaluation, serum chemistry evaluation, UA, vital sign evaluation, ECG, or physical examination
6. Have negative test results for hepatitis B surface antigen, anti-hepatitis B core antibody immunoglobulin M, anti-hepatitis C virus antibody, rapid plasma reagin/VDRL values, and anti-human immunodeficiency virus types 1
7. Be a nonsmoker (never smoked or have not smoked within the previous 2 years)
8. Have a body mass index (BMI)≧18 kg/m$^2$ and ≦30 kg/m$^2$
9. Have a supine pulse rate of not more than 100 bpm and not less than 50 bpm during the vital sign assessment at screening Exclusion Criteria Subjects who met any of the following criteria were not eligible to participate in the study:

1. Any hypersensitivity or allergic reaction to any β-lactam antibiotic or β-lactamase inhibitor 2. Clinically significant disease state in any body system that, in the opinion of the examining physician, would place the subject at risk or compromise the quality of the data
3. CrCl levels less than 80 mL/min (Cockcroft-Gault formula estimate)
4. Supine systolic blood pressure (BP)≧140 mm Hg or ≦90 mm Hg at screening
5. Supine diastolic BP≧90 mm Hg or ≦50 mm Hg at screening
6. Clinically significant ECG abnormalities based on PI interpretation, such as a PR interval ≧220 msec or ≦100 msec; QTc interval ≧450 msec for male and female subjects; sinus bradycardia (<50 bpm); sick sinus syndrome; first-, second-, or third-degree atrioventricular block; any type of tachycardia; more than 1 PVC on a 12-lead ECG; incomplete or complete left bundle-branch block; nonsinus rhythm; or evidence of myocardial ischemia/infarction (either changes suggesting acute ischemia/infarction or changes from previous tracings compatible with the infarction during the preceding 6 months)
7. History of alcohol or substance abuse within the previous 5 years
8. Positive urine test results for any drug of abuse, including cotinine or alcohol
9. Participation in any other clinical investigation using an experimental drug requiring repeated blood draws within 30 days of Day 1 of this study or participation in a blood donation program within the preceding 60 days
10. Consumption of caffeine, cruciferous vegetables, or orange or grapefruit-containing products within 48 hours before Day 1 or consumption of alcohol within 72 hours before Day 1
11. Any clinical condition that might affect the absorption, distribution, biotransformation, or excretion of ceftaroline or NXL-104
12. Employee or family member of an employee of the clinical research organization at which the study was conducted
13. Any concomitant medications, including over-the-counter medications and vitamin or herbal supplements (eg, St. Johns wort), taken within 14 days or 5 half-lives (whichever is longer) before Day 1 of study drug administration. (Hormonal drug products are prohibited from 30 days before Day 1, including oral contraceptives)
14. Previous use of ceftaroline or NXL-104 or previous participation in an investigational study of ceftaroline or NXL-104
15. Female subjects who were pregnant and/or breast-feeding
16. Inability or unwillingness to adhere to the study-specific procedures and restrictions
17. Any hypersensitivity or allergic reaction to heparin
18. History of recent vaccination within 14 days of first dose of study medication
19. History of a recent viral illness within 14 days of first dose of study medication Part A Part A was an open-label, 3-way crossover, single-dose study to evaluate the safety, tolerability, and pharmacokinetics of ceftaroline and NXL-104 following co-administration of a single intravenous (IV) dose of ceftaroline fosamil and NXL-104 in 12 healthy subjects.

The subjects were randomized (1:1:1) to receive three treatment sequences A, B and C as shown in Table 83.

Treatment A: single dose of 600 mg ceftaroline fosamil via IV infusion over one hour.
Treatment B: single dose of 600 mg NXL-104 via IV infusion over one hour.
Treatment C: single dose of 600 mg ceftaroline fosamil and 600 mg NXL-104 via concomitant IV infusion over one hour.

TABLE 83

Part A - Treatment Sequence

| Treatment Sequence (No. of Subjects) | Period I Treatment | Period II Treatment | Period III Treatment |
| --- | --- | --- | --- |
| I (4 subjects) | A | B | C |
| II (4 subjects) | C | A | B |
| III (4 subjects) | B | C | A |

There was a 5-day washout period after the study drug administration.

Selection and Timing of Dose for Each Subject

Subjects in part A were randomized to receive study drug between 0800 and 1000 hours following a standard breakfast given at 0700 hours on Days 1, 6, and 11. Following each dose administration, were to remain semirecumbent (excluding time when study procedures require otherwise) and awake for 1 hours.

No concomitant medications were permitted during the study unless needed to treat an AE. Subjects were instructed not to take any drugs for at least 14 days or 5 half-lives (whichever was longer) before the first day of dosing and during the course of the study. Subjects were to be specifically reminded that this includes over-the-counter medications such as aspirin, acetaminophen, ibuprofen, vitamin preparations, herbal and dietary supplements, and cough syrup, as well as medicines requiring a prescription. No hormonal drug products (including oral contraceptives) were to be allowed 30 days before Day 1 and throughout the study.

Screening

Part A (Day −21 to Day −2)

Screening was to be performed within 21 days before the first dose. At screening, a review of inclusion and exclusion criteria was conducted to determine the subject's eligibility for enrollment. Study procedures were reviewed with the subject, and documentation of informed consent was obtained before any study procedures are performed.

The following procedures were performed and recorded at screening:

Collect blood samples for serology testing, hematology evaluation (including CBC, prothrombin time and international normalized ratio [PT/INR], partial thromboplastin time [PTT], free hemoglobin, haptoglobin, and reticulocyte count), and comprehensive metabolic panel Collect urine for UA (including urine microscopy) and for drugs-of-abuse screen Perform β-HCG serum pregnancy test (female subjects only)

Calculate CrCl and BMI

Assess vital signs

Perform 12-lead ECG

Perform complete physical examination

Assess prior medications

Record medical and surgical history

Record any spontaneously reported AE or SAE between signing of informed consent and Day −1 for subjects who comply with all screening processes Study Days Subjects were admitted into a nonsmoking environment on Day −1 and were to remain in the clinic until 48 hours following Day 11 dose administration (Day 13), for a total of 13 overnight stays per subject (overnight stays Days −1 to 12).

The following protocol was used during the study days:

Day −1 (Period I)
Admit subjects to a nonsmoking environment
Collect any updated medical and surgical history not reported at screening
Collect urine for UA (including urine microscopy)
Collect urine for drugs-of-abuse screen
Conduct serum or urine pregnancy test (female subjects only)
Perform a complete physical examination
Record weight
Calculate CrCl
Collect blood sample for Coombs test (direct and indirect antiglobulin)
Collect blood samples for hematology evaluation (including CBC, PT/INR, PTT, free hemoglobin, haptoglobin, and reticulocyte count) and comprehensive metabolic panel
Assess AEs, SAEs, and prior medications
Provide dinner and snack at approximately 1800 and 2100 hours, respectively Day 1 (Period I)
Randomize each subject before the start of infusion
Administer study drug at 0800 hour via IV infusion over 1 hour (±5 minutes) according to the treatment sequence assigned (per Table 9.4.1-1)
Assess vital signs at 0.0 hour (within 4 hours before the start of infusion) and 0.5, 1, 2, 4, and 8 hours (±15 minutes) after the start of dose infusion
Collect PK blood samples at 0.0 hour (within 15 minutes before the start of infusion) predose and after the start of infusion at 20, 40, 60 (immediately before the end of study-drug infusion), 65, and 75 minutes and 1.5, 2, 3, 4, 6, 8, 12, and 18 hours
Collect PK urine samples from −2 to 0 hours predose and over the following continuous time intervals: 0 to 2, 2 to 4, 4 to 8, 8 to 12, and 12 to 24 hours after the start of infusion
Perform ECGs at 0.0 hour (within 20 minutes before the start of infusion) predose and at 1, 2, and 4 hours (±20 minutes) after the start of infusion
Assess AEs, SAEs, and concomitant medication use
Provide breakfast, lunch, dinner, and snack at approximately 0700, 1200, 1800, and 2100 hours, respectively Day 2 (Period I), Day 7 (Period II), and Day 12 (Period III)
Assess vital signs at 24 hours (±15 minutes) after the start of infusion in each period
Perform a 12-lead ECG 24 hours (±20 minutes) after the start of study drug infusion in each period
Collect PK blood samples from 24 through 36 hours after the start of study drug infusion in each period
Collect PK urine sample for 24-48 hours after the start of infusion in each period
Assess AEs, SAEs, and concomitant medication use
Begin the washout period (applicable to period I and II only)
Provide breakfast, lunch, dinner, and snack at approximately 0700, 1200, 1800, and 2100 hours, respectively Day 3 (Period I) and Day 8 (Period II)
Continue the washout period
Assess AEs, SAEs, and concomitant medication use
Complete the collection of PK urine sample from 24 to 48 hours after the start of infusion in each period
Collect PK blood sample at 48 hours after the start of infusion in each period
Provide breakfast, lunch, dinner, and snack at approximately 0700, 1200, 1800, and 2100 hours, respectively Day 4 (Period I) and Day 9 (Period II)
Continue the washout period
Assess AEs, SAEs, and concomitant medication use
Provide breakfast, lunch, dinner, and snack at approximately 0700, 1200, 1800, and 2100 hours, respectively Day 5 (Period II) and Day 10 (Period III)
Continue the washout period
Collect blood samples for hematology evaluation (including CBC, PT/INR, PTT, free hemoglobin, haptoglobin, and reticulocyte count) and comprehensive metabolic panel
Collect urine for UA (including urine microscopy)
Assess AEs, SAEs, and concomitant medication use
Provide breakfast, lunch, dinner, and snack at approximately 0700, 1200, 1800, and 2100 hours, respectively Day 6 (Period II) and Day 11 (Period III)
Administer study drug at 0800 hour via IV infusion over 1 hour (±5 minutes) according to the treatment sequence assigned (per Table 9.4.1-1)
Assess vital signs at 0.0 hour (within 4 hours before the start of infusion) and 0.5, 1, 2, 4, and 8 hours (±15 minutes) after the start of dose infusion
Collect PK blood samples at 0.0 hour (within 15 minutes before the start of infusion) predose and after the start of infusion at 20, 40, 60 (immediately before the end of study-drug infusion), 65, and 75 minutes and 1.5, 2, 3, 4, 6, 8, 12, and 18 hours
Collect PK urine samples at −2 to 0 hours predose and after the start of infusion over the following continuous time intervals: 0 to 2, 2 to 4, 4 to 8, 8 to 12, and 12 to 24 hours
Perform ECGs at 0.0 hour (within 20 minutes before the start of infusion) predose and at 1, 2, and 4 hours (±20 minutes) after the start of infusion
Assess AEs, SAEs, and concomitant medication use
Provide breakfast, lunch, dinner, and snack at approximately 0700, 1200, 1800, and 2100 hours, respectively Day 13 (Period III)
Assess AEs, SAEs, and concomitant medication use
Complete the collection of PK urine sample from 24 to 48 hours after the start of infusion
Collect PK blood sample at 48 hours after the start of infusion
Provide breakfast at approximately 0700 hours
Perform a complete physical examination
Discharge subjects
End of Study (EOS)
EOS evaluations were completed within 7 to 10 days from Day 11 or at the time of early discontinuation Drug Concentration Measurements Blood Sampling Blood samples were collected at the following times to determine ceftaroline, ceftaroline fosamil, ceftaroline M-1 (metabolite of ceftaroline fosamil), and NXL-104 free-acid plasma concentrations.

Days 1 (Period I), 6 (Period II), and 11 (Period III): in each study period immediately before (within 15 minutes) the start of infusion and after the start of study drug infusion at 20, 40, 60 (immediately before the end of study-drug infusion), 65, and 75 minutes and at 1.5, 2, 3, 4, 6, 8, 12, 18, 24, 36, and 48 hours Urine Sampling Urine was collected during the following time intervals in each part of study.

Part A

Urine was collected from −2 to 0 hours predose and from 0 to 2, 2 to 4, 4 to 8, 8 to 12, 12 to 24, and 24 to 48 hours after the start of infusion in each period.

Pharmacokinetic Analyses

The principal parameters describing the pharmacokinetics of ceftaroline, ceftaroline fosamil, ceftaroline M-1 (metabolite of ceftaroline fosamil), and NXL-104 were derived from plasma concentrations using noncompartmental analysis with the software program WinNonlin. Plasma concentrations below the limit of quantification were treated as zero for all PK calculations. The actual sampling times were used in the calculations of PK parameters.

Plasma Data

The following PK parameters were determined for ceftaroline, ceftaroline ceftaroline M-1, and NXL-104 free acid: $AUC_{0-t}$ and area under the plasma concentration versus time curve from time zero to infinity ($AUC_{0-\infty}$), $C_{max}$, time of maximum plasma concentration ($T_{max}$), $T_{1/2}$, CL, volume of distribution ($V_z$), and steady-state volume of distribution ($V_{ss}$). Minimum plasma concentration ($C_{min}$), accumulation ratio ($R_{ac}$), and area under the plasma concentration versus time curve during the dosing interval, τ, ($AUC_{0-\tau}$) will be determined following multiple-dose administration.

Because all doses of ceftaroline are expressed in terms of anhydrous, acetate-free ceftaroline fosamil (ceftaroline prodrug, molecular weight=684.68), the following corrections were made to the dose when calculating PK parameters that include doses for ceftaroline (molecular weight=604.70) and ceftaroline M-1 (molecular weight=622.72):

Ceftaroline dose=0.883×ceftaroline fosamil dose

Ceftaroline M-1 dose=0.909×ceftaroline fosamil dose

The $C_{max}$ of ceftaroline, ceftaroline fosamil, ceftaroline M-1, and NXL-104 free acid was determined observationally as the peak concentration for each subject. $T_{max}$ was determined as the time corresponding to $C_{max}$.

Area under the plasma concentration versus time curve up to the time corresponding to the last measurable concentration ($AUC_{0-t}$) was calculated by numeric integration using the linear trapezoidal rule as follows:

$$AUC_{0-t} = \sum_{i=2}^{n} 0.5 \times (C_i + C_{i-1}) \times (t_i - t_{i-1})$$

in which $C_i$ is the plasma ceftaroline, ceftaroline fosamil, ceftaroline M-1, and NXL-104 free-acid concentrations at the corresponding sampling time point $t_i$ and n is the number of time points up to and including the last quantifiable concentration.

Estimates of $T_{1/2}$ were calculated using the following equation:

$$T_{1/2}=0.693/\lambda_z$$

in which $\lambda_z$ is the terminal elimination rate constant and was determined by noncompartmental analysis using WinNonlin. Briefly described, a regression analysis was performed on the terminal linear phase of semilogarithmic plots of individual ceftaroline, ceftaroline fosamil, ceftaroline M-1, and NXL-104 free acid concentration-time data.

The $AUC_{0-\infty}$ was calculated according to the following equation:

$$AUC_{0-\infty}=AUC_{0-t}+C_{last}/\lambda_z$$

in which $C_{last}$ is the last measurable concentration.

CL was calculated with the following equation:

$$CL=Dose_{iv}/AUC_{0-\infty}$$

$V_z$ based on the terminal phase was determined as:

$$V_z=Dose_{iv}/\lambda_z \times AUC_{0-\infty}$$

$C_{min}$ was determined observationally as the drug concentration at the end of the dosing interval at steady-state.

$V_{ss}$ following multiple-dose administration was determined using the following equations:

$$V_{ss} = CL \times \frac{AUMC}{AUC} - \frac{Tdur}{2}$$

in which with Tdur is the infusion duration $$AUMC_{0-\infty} = AUMC_{0-t} + \frac{C_{last}t_{last}}{\lambda_z} + \frac{C_{last}}{\lambda_z \lambda_z}$$

in which $AUMC_{0-\infty}$ is the area under the first moment of the plasma concentration-versus-time curve from time zero to infinity with extrapolation of the terminal phase.

Area under the first moment of the plasma concentration-versus-time curve up to the time corresponding to the last measurable concentration ($AUMC_{0-t}$) was calculated by numeric integration using the linear trapezoidal rule as follows:

$$AUMC_{0-t} = \sum_{i=2}^{n} 0.5 \times (C_i t_i + C_{i-1} t_{i-1}) \times (t_i - t_{i-1})$$

$R_{ac}$ was calculated using the following equation:

$$R_{ac} = \frac{AUC_{0-t\,(Day\,7)}}{AUC_{0-t\,(Day\,1)}}$$

Urine Data

The PK parameters to be determined from the urine excretion data included the cumulative amount of ceftaroline, ceftaroline fosamil, ceftaroline M-1, and NXL-104 free acid excreted during the entire urine collection period from time 0 to time t ($Ae_{0-t}$), renal clearance ($CL_r$) and the percent of dose excreted (% Dose). These parameters were determined using noncompartmental analysis.

The cumulative amount of ceftaroline, ceftaroline fosamil, ceftaroline M-1, and NXL-104 excreted over all collection intervals, $Ae_{0-t}$, was calculated as $$Ae_{0-t} = \sum_{i=1}^{n} Ae_i$$

in which $Ae_i$ is the amount of drug excreted per collection interval calculated as $$Ae_i = \text{Concentration} \times \text{Volume}$$

$CL_r$ of ceftaroline, ceftaroline fosamil, ceftaroline M-1, and NXL-104 was determined according to the following equation:

$$CL_r = \frac{Ae_{0-t}}{AUC_{0-t}}$$

Percent Dose Excreted in Urine was Determined According to the Following Equation:

Statistical Analyses of Pharmacokinetic Parameters

In part A, PK parameters were compared by analysis of variance using SAS version 9.1.3 on a UNIX operating system. A general linear model with sequence, subject within sequence, treatment, and period as factors was used as the basis for the analysis. The PK parameters for ceftaroline, ceftaroline fosamil, and ceftaroline M-1 following administration of ceftaroline fosamil concomitantly with NXL-104 (test) were compared with the PK parameters for these analytes following administration of ceftaroline fosamil alone (reference). In addition, the PK parameters for NXL-104 following administration of NXL-104 concomitantly with ceftaroline fosamil (test) were compared with the PK parameters for NXL-104 following administration of NXL-104 alone (reference). Statistical inference was based on log-transformed values for the $C_{max}$ and AUC parameters. The 2-sided 90% CI for the ratio of geometric means of $C_{max}$ and AUC between the test and reference treatments was constructed. $T_{max}$ for test and reference was compared using the Wilcoxon signed rank test.

There were no safety concerns and no pharmacokinetic interactions were found between ceftaroline fosamil and NXL-104.

Table 84 provides the pharmacokinetic data for Part A of the study.

Part B

Part B is a randomized, double-blind, placebo-controlled, 10-day multiple dose study to evaluate the safety, tolerability, and pharmacokinetics of ceftaroline and NXL-104 following co-administration of multiple IV doses of ceftaroline fosamil and NXL-104 over 10 days to 48 healthy subjects. The treatment groups for Part B are as follows:

Treatment group I: multiple doses of 600 mg ceftaroline fosamil and 600 mg NXL04 co-administered every 12 hours (q12h) via IV infusion over 1 hour Treatment group II: multiple doses of 400 mg ceftaroline fosamil and 400 mg NXL-104 co-administered every 8 hours (q8h) via IV infusion over 1 hour Treatment group III: multiple doses of 900 mg ceftaroline fosamil and 900 mg NXL-104 co-administered q12h via IV infusion over 1 hour Treatment group IV: multiple doses of 600 mg ceftaroline fosamil and 600 mg NXL-104 co-administered q8h via IV infusion over 1 hour Treatment group V: multiple doses of placebo (normal saline) administered q12h via IV infusion over 1 hour Treatment group VI: multiple doses of placebo (normal saline) administered q8h via IV infusion over 1 hour Subject participation will require a commitment of up to 21 days, not including the Screening Visit, which may occur up to 21 days before study drug administration. Treatment duration in each cohort for part B is 10 days. Subjects will be confined to the clinical research unit from Day −1 through Day 12.

The following PK parameters for ceftaroline, ceftaroline fosamil, ceftaroline M-1 (metabolite of ceftaroline fosamil), and NXL-104 free acid will be calculated following multiple-dose administration: minimum plasma concentration (Cmin), accumulation ration (Rac), area under the plasma concentration versus time curve during the dosing interval, τ, (AUC0τ), Cmax, Tmax, CL, T½, Ae0-t, CLr, and % Dose.

TABLE 84

Pharmacokinetic data for Part A

| | Treatment | | Cmax (µg/mL) | $T_{max}$ (hr) | $AUC_{0-inf}$ (µg*hr/mL) | $T_{1/2}$ (hr) |
|---|---|---|---|---|---|---|
| Ceftaroline | 600 mg Ceftaroline fosamil | Geo mean CV (%) | 24.77 27.55 | 1.00 (1.00-4.00)* | 60.97 13.70 | 2.51 13.88 |
| | 600 mg NXL-104 + Ceftaroline fosamil 600 mg | Geo mean CV (%) | 26.71 12.06 | 1.00 (1.00-1.08)* | 60.02 10.83 | 2.47 16.17 |
| Ceftaroline fosamil | 600 mg Ceftaroline fosamil | Geo mean CV (%) | 2.11 30.73 | 0.67 (0.33-1.50)* | 2.17 15.59 | 0.084 222.8 |
| | 600 mg NXL-104 + Ceftaroline fosamil 600 mg | Geo mean CV (%) | 2.37 21.98 | 0.67 (0.33-1.00)* | 2.16 11.97 | 0.055 12.34 |
| Ceftaroline M-1 | 600 mg Ceftaroline fosamil | Geo mean CV (%) | 3.29 43.02 | 1.08 (1.00-.6.00)* | 16.42 18.72 | 3.75 11.26 |
| | 600 mg NXL-104 + Ceftaroline fosamil 600 mg | Geo mean CV (%) | 3.21 42.64 | 1.04 (0.67-2.00)* | 15.78 21.67 | 3.78 14.01 |
| NXL-104 | 600 mg NXL-104 | Geo mean CV (%) | 29.48 12.97 | 1.00 (1.00-1.08)* | 51.90 11.60 | 1.64 26.32 |
| | 600 mg NXL-104 + Ceftaroline fosamil 600 mg | Geo mean CV (%) | 29.06 11.65 | 1.00 (1.00-1.08)* | 51.21 13.52 | 1.63 19.97 |

*Median (Min-Max)

Table 85 gives the expected mean pharmacokinetic parameters for a single dose of 400 mg dose of ceftaroline fosamil, NXL-104 or a combination of 400 mg ceftaroline fosamil and 400 mg NXL-104

TABLE 85

Expected pharmacokinetic parameters for a single 400 mg dose of ceftaroline fosamil, NXL-104 or 400 mg NXL-104 + ceftaroline fosamil 400 mg

| | Treatment | $C_{max}$ (µg/mL) | $T_{max}$ (hr) | $AUC_{0-inf}$ (µg * hr/mL) | $T_{1/2}$ (hr) |
|---|---|---|---|---|---|
| Ceftaroline | 400 mg Ceftaroline fosamil | 16.51 | 0.67 | 40.65 | 1.67 |
| | 400 mg NXL-104 + Ceftaroline fosamil 400 mg | 17.81 | 0.67 | 40.01 | 1.65 |
| Ceftaroline fosamil | 400 mg Ceftaroline fosamil | 1.41 | 0.45 | 1.45 | 0.06 |
| | 400 mg NXL-104 + Ceftaroline fosamil 400 mg | 1.58 | 0.45 | 1.44 | 0.04 |
| Ceftaroline M-1 | 400 mg Ceftaroline fosamil | 2.19 | 0.72 | 10.95 | 2.5 |
| | 400 mg NXL-104 + Ceftaroline fosamil 400 mg | 2.14 | 0.69 | 10.52 | 2.52 |
| NXL-104 | 400 mg NXL-104 | 19.65 | 0.67 | 34.6 | 1.09 |
| | 400 mg NXL-104 + Ceftaroline fosamil 400 mg | 19.37 | 0.67 | 34.14 | 1.09 |

Table 86 gives the expected mean pharmacokinetic parameters for a single dose of 900 mg dose of ceftaroline fosamil, NXL-104 or a combination of 900 mg ceftaroline fosamil and 900 mg NXL-104

TABLE 86

Expected pharmacokinetic parameters for a single 900 mg dose of ceftaroline fosamil, NXL-104 or 900 mg NXL-104 + ceftaroline fosamil 900 mg

| | Treatment | $C_{max}$ (µg/mL) | $T_{max}$ (hr) | $AUC_{0-inf}$ (µg * hr/mL) | $T_{1/2}$ (hr) |
|---|---|---|---|---|---|
| Ceftaroline | 900 mg Ceftaroline fosamil | 37.16 | 1.5 | 91.46 | 3.77 |
| | 900 mg NXL-104 + Ceftaroline fosamil 900 mg | 40.07 | 1.5 | 90.03 | 3.71 |
| Ceftaroline fosamil | 900 mg Ceftaroline fosamil | 3.17 | 1.01 | 3.26 | 0.13 |
| | 900 mg NXL-104 + Ceftaroline fosamil 900 mg | 3.56 | 1.01 | 3.24 | 0.08 |
| Ceftaroline M-1 | 900 mg Ceftaroline fosamil | 4.94 | 1.62 | 24.63 | 5.63 |
| | 900 mg NXL-104 + Ceftaroline fosamil 900 mg | 4.82 | 1.56 | 23.67 | 5.67 |
| NXL-104 | 900 mg NXL-104 | 44.22 | 1.5 | 77.85 | 2.46 |
| | 900 mg NXL-104 + Ceftaroline fosamil 900 mg | 43.59 | 1.5 | 76.82 | 2.45 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

All patents, patent applications, publications, product descriptions, and protocols are cited throughout this application, the disclosures of which are incorporated herein by reference in their entireties for all purposes.

What is claimed is:

1. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a characteristic peak at about 13.0 and about 17.3+/−0.5 degrees 2θ.

2. The crystalline form according to claim 1, wherein the salt is a sodium salt of (1R,2S,5R)-7-oxo-6-sulphooxy-1,6-diazabicyclo[3.2.1]octane-2-carboxamide.

3. The crystalline form according to claim 2, wherein the crystalline form has an X-Ray powder diffraction pattern comprising a characteristic peak at about 19.9, about 22.0 or about 28.2+/−0.5 degrees 2θ.

4. The crystalline form according to claim 2, wherein the crystalline form has an X-Ray powder diffraction pattern comprising a characteristic peak at about 16.5+/−0.5 degrees 2θ.

5. The crystalline form according to claim 2, wherein the crystalline form has an X-Ray powder diffraction pattern comprising a characteristic peak at about 17.5+/−0.5 degrees 2θ.

6. The crystalline form according to claim 2, wherein the crystalline form has an X-Ray powder diffraction pattern comprising a characteristic peak at; about 22.3+/−0.5 degrees 2θ.

7. The crystalline form according to claim 2, wherein the crystalline form has an X-Ray powder diffraction pattern comprising a characteristic peak at about 19.2; about 19.5+/−0.5 degrees 2θ or a combination thereof.

8. The crystalline form according to claim 2, wherein the crystalline form has an X-Ray powder diffraction pattern comprising a characteristic peak at about 19.9; about 22.0; about 25.2; about 28.2+/−0.5 degrees 2θ or a combination thereof.

9. The crystalline form according to claim 2, wherein the crystalline form has an X-Ray powder diffraction pattern comprising a characteristic peak at about 23.2; about 30.2; about 30.9; about 36.1+/−0.5 degrees 2θ or a combination thereof.

10. The crystalline form according to claim 1, wherein the crystalline form has an X-Ray powder diffraction pattern comprising a characteristic peak at about 13.0; about 17.3; about 19.9; about 22.0; and about 28.2+/−0.5 degrees 2θ.

11. A crystalline form of trans-7-oxo-6-(sulphooxv)-1,6-diazabicyclo[3,2,1]octane-2-carboxamide or a pharmaceutically acceptable salt thereof, wherein the crystalline form has an X-Ray powder diffraction pattern comprising a characteristic peak at about 13.0; about 16.5; about 17.3; about 17.5; about 19.2; about 19.5; about 19.9; about 22.0; about 22.3; about 23.2; about 25.2; about 28.2; about 30.2; about 30.9 and about 36.1+/−0.5 degrees 2θ.

12. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 5.1 and about 6.8+/−0.2 nm.

13. The crystalline form according to claim 12, wherein the crystalline form has an X-Ray powder diffraction pattern comprising a d-spacing value at about 5.4+/−0.2 nm.

14. The crystalline form according to claim 12, wherein the crystalline form has an X-Ray powder diffraction pattern comprising a d-spacing value at about 3.2; about 4.0; about 4.5; +/−0.2 nm or a combination thereof.

15. The crystalline form according to claim 12, wherein the crystalline form has an X-Ray powder diffraction pattern comprising a d-spacing value at about 2.5; about 2.9; about 3.0; about 3.2; about 3.5; about 3.8; about 4.0; about 4.5; about 4.6; about 5.4; +/−0.2 nm or a combination thereof.

16. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 2.5; about 2.9; about 3.0; about 3.2; about 3.5; about 3.8; about 4.0; about 4.5; about 4.6; about 5.1; about 5.4; and about 6.8+/−0.2 nm.

17. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a characteristic peak at about 8.7; about 11.3; about 12.5; about 16.3; about 17.5; about 17.8; about 18.6; about 21.0; about 22.3; about 26.2; about 26.6; about 26.9; about 27.6; about 28.7; about 29.8; about 30.4; about 31.2; about 32.9; about 33.4; about 34.4; about 37.1; about 37.3; about 37.6 and about 38.5+/−0.5 degrees 2θ.

18. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 2.3; about 2.4; about 2.6; about 2.7; about 2.9; about 3.0; about 3.1; about 3.2; about 3.3; about 3.4; about 4.0; about 4.2; about 4.8; about 5.0; about 5.1; about 5.4; about 7.1; about 7.8 and about 10.1+/−0.2 nm.

19. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a characteristic peak at about 8.5 and about 24.3+/−0.5 degrees 2θ.

20. The crystalline form according to claim 19, wherein the crystalline form has an X-Ray powder diffraction pattern comprising a characteristic peak at about 18.4; about 18.7; about 24.0; about 25.7; about 27.4; about 28.8; +/−0.5 degrees 2θ or a combination thereof.

21. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a characteristic peak at about 17.8 and about 18.6+/−0.5 degrees 2θ.

22. The crystalline form according to claim 21, wherein the crystalline form has an X-Ray powder diffraction pattern comprising a characteristic peak at about 8.7; about 11.3; about 12.5; about 16.3; about 21.1; about 27.0; about 26.6; about 28.7 or a combination thereof.

23. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a characteristic peak at about 17.8 and about 18.6+/−0.5 degrees 2θ.

24. The crystalline form according to claim 23, wherein the crystalline form has an X-Ray powder diffraction pattern comprising a characteristic peak at about 14.2; about 15.0; about 22.5;

about 22.8; about 24.6; about 28.0+/−0.5 degrees 2θ or a combination thereof.

25. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a characteristic peak at about 17.8 and about 18.6+/−0.5 degrees 2θ.

26. The crystalline form according to claim 25, wherein the crystalline form has an X-Ray powder diffraction pattern comprising a characteristic peak at about 14.4; about 15.5; about 19.3; +/−0.5 degrees 2θ or a combination thereof.

27. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 3.7 and about 10.4+/−0.2 nm.

28. The crystalline form according to claim 27, wherein the crystalline form has an X-Ray powder diffraction pattern comprising a d-spacing value at about 3.1; about 3.3; about 3.5; about 3.7; about 4.7; about 4.8; +/−0.2 nm or a combination thereof.

29. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 4.8 and about 5.0+/−0.2 nm.

30. The crystalline form according to claim 29, wherein the crystalline form has an X-Ray powder diffraction pattern comprising a d-spacing value at about 3.1; about 3.3; about 3.4; about 4.2; about 5.4; about 7.1; about 7.8; about 10.1+/−0.2 nm or a combination thereof.

31. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 5.6 and about 9.0+/−0.2 nm.

32. The crystalline form according to claim 31, wherein the crystalline form has an X-Ray powder diffraction pattern comprising a d-spacing value at about 3.2; about 3.6; about 3.9; about 4.0; about 5.9; about 6.2+/−0.2 nm or a combination thereof.

33. A crystalline form of trans-7-oxo-6-(sulphooxy)-1,6-diazabicyclo[3,2,1]octane-2-carboxamide or a pharmaceutically acceptable salt thereof, wherein the crystalline form has an X-Ray powder diffraction pattern comprising a d-spacing value at about 4.9 and about 13.6+/−0.2 nm.

34. The crystalline form according to claim 33, wherein the crystalline form has an X-Ray powder diffraction pattern comprising a d-spacing value at about 4.6; about 5.7; about 6.1+/−0.2 nm or a combination thereof.

* * * * *